(12) United States Patent
Weetall et al.

(10) Patent No.: US 12,023,335 B2
(45) Date of Patent: Jul. 2, 2024

(54) METHOD FOR TREATING PANCREATIC CANCER

(71) Applicants: PTC THERAPEUTICS, INC., South Plainfield, NJ (US); THE TRUSTEES OF COLUMBIA UNIVERSITY IN THE CITY OF NEW YORK, New York, NY (US)

(72) Inventors: Marla L. Weetall, Morristown, NJ (US); Liangxian Cao, East Brunswick, NJ (US); Thomas W. Davis, South Orange, NJ (US); Melissa L. Dumble, Watchung, NJ (US); Jaime A. Eberle-Singh, Philadelphia, PA (US); Kenneth P. Olive, New York, NY (US)

(73) Assignee: PTC THERAPEUTICS, INC., Warren, NJ (US)

( * ) Notice: Subject to any disclaimer, the term of this patent is extended or adjusted under 35 U.S.C. 154(b) by 0 days.

(21) Appl. No.: 17/267,988

(22) PCT Filed: Aug. 17, 2019

(86) PCT No.: PCT/US2019/046972
§ 371 (c)(1),
(2) Date: Feb. 11, 2021

(87) PCT Pub. No.: WO2020/055544
PCT Pub. Date: Mar. 19, 2020

(65) Prior Publication Data
US 2021/0236492 A1 Aug. 5, 2021

Related U.S. Application Data

(60) Provisional application No. 62/719,526, filed on Aug. 17, 2018.

(51) Int. Cl.
*A61K 31/506* (2006.01)
*A61K 31/337* (2006.01)
*A61K 31/7068* (2006.01)
*A61P 35/00* (2006.01)

(52) U.S. Cl.
CPC .......... *A61K 31/506* (2013.01); *A61K 31/337* (2013.01); *A61K 31/7068* (2013.01); *A61P 35/00* (2018.01)

(58) Field of Classification Search
CPC . A61K 31/506; A61K 31/337; A61K 31/7068
See application file for complete search history.

(56) References Cited

U.S. PATENT DOCUMENTS

| | | |
|---|---|---|
| 3,978,055 A | 8/1976 | Fauran et al. |
| 5,750,531 A | 5/1998 | Lee et al. |
| 6,498,165 B1 | 12/2002 | Armstrong et al. |
| 6,855,719 B1 | 2/2005 | Thomas et al. |
| 7,074,789 B2 | 7/2006 | Armistead et al. |
| 7,226,927 B2 | 6/2007 | Cai et al. |
| 7,282,504 B2 | 10/2007 | Armistead et al. |
| 7,494,997 B2 | 2/2009 | Asaki et al. |
| 7,582,630 B2 | 9/2009 | Dickerson et al. |
| 7,601,840 B2 | 10/2009 | Moon et al. |
| 7,767,689 B2 | 8/2010 | Moon et al. |
| 7,803,801 B2 | 9/2010 | Kodama et al. |
| 7,855,205 B2 | 12/2010 | Huang et al. |
| 7,968,556 B2 | 6/2011 | Mortensen et al. |
| 8,076,352 B2 | 12/2011 | Cao et al. |
| 8,076,353 B2 | 12/2011 | Cao et al. |
| 8,222,262 B2 | 7/2012 | Eriksen et al. |
| 8,329,737 B2 | 12/2012 | Styles et al. |
| 8,367,694 B2 | 2/2013 | Olasz et al. |
| 8,383,634 B2 | 2/2013 | Mortensen et al. |
| 8,415,358 B2 | 4/2013 | Eriksen et al. |
| 8,835,648 B2 | 9/2014 | Thomas et al. |
| 9,434,719 B2 | 9/2016 | Caferro et al. |
| 2002/0052386 A1 | 5/2002 | Armistead et al. |
| 2003/0004174 A9 | 1/2003 | Armistead et al. |
| 2003/0055044 A1 | 3/2003 | Davies et al. |
| 2003/0060629 A1 | 3/2003 | Kuo et al. |
| 2003/0069239 A1 | 4/2003 | Cai et al. |
| 2003/0199534 A1 | 10/2003 | Armistead et al. |
| 2004/0043388 A1 | 3/2004 | Come et al. |
| 2004/0097503 A1 | 5/2004 | Cai et al. |

(Continued)

FOREIGN PATENT DOCUMENTS

| | | |
|---|---|---|
| CA | 102819373 A1 | 6/2012 |
| CN | 1155281 A | 7/1997 |

(Continued)

OTHER PUBLICATIONS

Eberle (Mol Cancer Res; 2016, 14 (11_Supplement): A22).*
Hoff (The New England Journal of Medicine; 2013, 369, 1691-1703).*
International Search Report for PCT/US2020/013645, mailed May 15, 2020.
International Search Report in PCT/US2013/071153, mailed May 20, 2014.
International Search Report in PCT/US2013/071216, mailed May 20, 2014.
International Search Report for PCT/US2013/071132, mailed May 20, 2014.
International Search Report for PCT/US2020/019884, mailed May 22, 2020.
International Search Report for PCT/US2020/021648, mailed Jun. 16, 2020.
International Search Report for PCT/US2020/025532, mailed Jun. 18, 2020.

(Continued)

*Primary Examiner* — Pancham Bakshi
(74) *Attorney, Agent, or Firm* — Hoffmann & Baron, LLP

(57) ABSTRACT

A method for treating pancreatic cancer in a subject in need thereof comprising, administering to the subject an effective amount of a tubulin polymerization inhibitor compound is described herein. More particularly, a method for treating pancreatic ductal adenocarcinoma in a subject in need thereof comprising, administering to the subject an effective amount of a substituted reverse pyrimidine tubulin polymerization inhibitor compound alone or in combination with other chemo-therapeutic agents is described herein.

7 Claims, 21 Drawing Sheets

(56) References Cited

U.S. PATENT DOCUMENTS

| | | |
|---|---|---|
| 2004/0110821 A1 | 6/2004 | Konkel et al. |
| 2005/0113342 A1 | 5/2005 | Honold et al. |
| 2005/0203114 A1 | 9/2005 | Armistead et al. |
| 2008/0039450 A1 | 2/2008 | Jensen et al. |
| 2008/0182852 A1 | 7/2008 | Johnson et al. |
| 2009/0042890 A1 | 2/2009 | Mortensen et al. |
| 2009/0325989 A1 | 12/2009 | Eriksen et al. |
| 2010/0158858 A1 | 6/2010 | Cao et al. |
| 2010/0204230 A1 | 8/2010 | Blurton et al. |
| 2010/0286161 A1 | 11/2010 | Eriksen et al. |
| 2010/0292262 A1 | 11/2010 | Dorsch et al. |
| 2011/0039873 A1 | 2/2011 | Gaeta et al. |
| 2011/0098301 A1 | 4/2011 | Dixon et al. |
| 2011/0190239 A1 | 8/2011 | Moon et al. |
| 2011/0224217 A1 | 9/2011 | Mortensen et al. |
| 2012/0083457 A1 | 4/2012 | Usayapant et al. |
| 2012/0171245 A1 | 7/2012 | Charifson et al. |
| 2013/0035331 A1 | 2/2013 | Moussy et al. |
| 2013/0150364 A1 | 6/2013 | Takahashi et al. |
| 2015/0315182 A1* | 11/2015 | Lee ............... A61K 31/506 514/249 |
| 2016/0340354 A1 | 11/2016 | Davis et al. |
| 2020/0024260 A1 | 1/2020 | Lee et al. |

FOREIGN PATENT DOCUMENTS

| | | |
|---|---|---|
| CN | 1429222 A | 7/2003 |
| CN | 101516873 A | 8/2009 |
| CN | 101679432 A | 3/2010 |
| EA | 028033 B1 | 9/2017 |
| EP | 2454257 B1 | 8/2013 |
| IN | 201641014592 A | 11/2017 |
| JP | 2006/045119 A1 | 2/2006 |
| JP | 2007/520558 A | 7/2007 |
| JP | 2011136925 A | 7/2011 |
| JP | 2018-510221 A | 4/2018 |
| RU | 2533825 C2 | 11/2014 |
| WO | 96/05177 A1 | 2/1996 |
| WO | 98/43968 A1 | 10/1998 |
| WO | 00/29403 A1 | 5/2000 |
| WO | 2001/014375 A1 | 3/2001 |
| WO | 01/30778 A1 | 5/2001 |
| WO | 2001/060816 A1 | 8/2001 |
| WO | 2001/072745 A1 | 10/2001 |
| WO | 02/22608 A1 | 3/2002 |
| WO | 02/48148 A2 | 6/2002 |
| WO | 2002/047690 A1 | 6/2002 |
| WO | 02/066481 A1 | 8/2002 |
| WO | 2002/066480 A2 | 8/2002 |
| WO | 03/004492 A1 | 1/2003 |
| WO | 2003/000682 A1 | 1/2003 |
| WO | 03/011837 A1 | 2/2003 |
| WO | 03/075828 A2 | 9/2003 |
| WO | 03/099811 A1 | 12/2003 |
| WO | 2004/005282 A1 | 1/2004 |
| WO | 2004/007407 A2 | 1/2004 |
| WO | 2004/021989 A1 | 3/2004 |
| WO | 2005/076854 A2 | 8/2005 |
| WO | 2005/089764 A1 | 9/2005 |
| WO | 2005/076854 A1 | 10/2005 |
| WO | 2006/113703 A2 | 10/2006 |
| WO | 2007/002051 A1 | 1/2007 |
| WO | 2008/040753 A1 | 4/2008 |
| WO | 2008/075330 A1 | 6/2008 |
| WO | 2008/079933 A1 | 7/2008 |
| WO | 2008/127714 A1 | 10/2008 |
| WO | 2008/127715 A1 | 10/2008 |
| WO | 2008/132502 A1 | 11/2008 |
| WO | 2009/013614 A1 | 1/2009 |
| WO | 2009/064835 A1 | 5/2009 |
| WO | 2009/071701 A1 | 6/2009 |
| WO | 2009/092431 A1 | 7/2009 |
| WO | 2009/093049 A1 | 7/2009 |
| WO | 2010/002985 A1 | 1/2010 |
| WO | 2010/016005 A1 | 2/2010 |
| WO | 2010/026087 A1 | 3/2010 |
| WO | 2010/061903 A1 | 6/2010 |
| WO | 2010/138575 A1 | 12/2010 |
| WO | 2010/138758 A1 | 12/2010 |
| WO | 2011/008830 A1 | 1/2011 |
| WO | 2011/008915 A1 | 1/2011 |
| WO | 2011/086085 A1 | 7/2011 |
| WO | 2011/101161 A1 | 8/2011 |
| WO | 2011/121418 A1 | 10/2011 |
| WO | 2012/035023 A1 | 3/2012 |
| WO | 2012/050884 A2 | 4/2012 |
| WO | 2012/078777 A1 | 6/2012 |
| WO | 2012/115478 A1 | 8/2012 |
| WO | 2012/115480 A1 | 8/2012 |
| WO | 2013/004332 A1 | 1/2013 |
| WO | 2014/081906 A2 | 5/2014 |
| WO | 2014/081944 A2 | 5/2014 |
| WO | 2014/081955 A1 | 5/2014 |
| WO | 2015/030847 A1 | 3/2015 |
| WO | 2015/076800 A1 | 5/2015 |
| WO | 2015/076801 A1 | 5/2015 |
| WO | 2017/132049 A1 | 8/2017 |
| WO | 2017/149550 A1 | 9/2017 |
| WO | 2020/055544 A2 | 3/2020 |
| WO | 2020/185648 A1 | 9/2020 |

OTHER PUBLICATIONS

International Search Report in PCT/US2013/071142, mailed May 20, 2014.
Written Opinion of the International Searching Authority for PCT/US2020/025532, mailed Jun. 18, 2020.
Written Opinion of the International Searching Authority in PCT/US2013/071153, mailed May 20, 2014, USPTO.
Written Opinion of the International Searching Authority in PCT/US2013/071216, mailed May 20, 2014.
Written Opinion for PCT/US2013/071132, mailed May 20, 2014.
Written Opinion of the International Searching Authority for PCT/US2020/013645, mailed May 15, 2020.
Written Opinion of the International Searching Authority for PCT/US2020/019884, mailed May 22, 2020.
Written Opinion of the International Searching Authority for PCT/US2020/021648, mailed Jun. 16, 2020.
Written Opinion for PCT/US2013/071142, mailed May 20, 2014.
Ma et al., "Combinatorial Synthesis of Substituted Biaryls and Heterocyclic Arylamines", Journal of Combinatorial Chemistry, 2004, vol. 6(3):426-430.
Abdouh et al., "BMI1 sustains human glioblastoma multiforme stem cell renewal." J Neurosci Res 2009;29(28):8884-8896.
Adams, "The development of proteasome inhibitors as anticancer drugs", Cancer Cell, vol. 5, pp. 417-421, May 2004.
Agaram et al.,"Targeted Exome Sequencing Profiles Genetic Alterations in Leiomyosarcoma. Genes Chromosomes." Cancer 2016:55(2):124-130.
Bakhsinyan et al., "BMI1 is a therapeutic target in recurrent medulloblastoma," Oncogene, published online Oct. 22, 2018.
Barbosa et al., "Acute myeloid leukemia driven by the CALM-AF10 fusion gene is dependent on BMI1," Experimental Hematology, 2019, vol. 74, pp. 42-51.
Bolomsky et al., "The anti-mitotic agents PTC-028 and PTC596 display potent activity in pre-clinical models of multiple myeloma but challenge the role of BMI-1 as an essential tumour gene," British Society for Haematology (2020), 190, 877-890.
Bregman et al., "Identification of a Potent, State-Dependent Inhibitor of Nav 1.7 With Oral Efficacy in the Formalin Model of Persistent Pain", Journal of Medicinal Chemistry, 2011, vol. 54(13):4427-4445.
Byth et al., "Imidazo [1,2-a] pyridines. Part 2: SAR and optimisation of a potent and selective class of cyclin-dependent kinase inhibitors", Bioorganic & Medicinal Chemistry Letters, 2004, vol. 14 (9), pp. 2245-2248.
CAS Reg. No. 1348721-67-4, 2011.
CAS Reg. No. 1380971-24-3, 2012.

(56) References Cited

OTHER PUBLICATIONS

CAS Reg. No. 396135-22-1, Feb. 27, 2002.
CAS Reg. No. 79871-84-4, Nov. 16, 1984.
CAS Reg. No. 79871-85-5, Nov. 16, 1984.
CAS Reg. No. 1203795-19-0, Jan. 27, 2010.
CAS Reg. No. 1203795-20-3, Jan. 27, 2010.
Chaki et al., "MC4 receptor antagonist and serotonin reuptake inhibitor with anxiolytic- and antidepressant-like activity." Pharmacol Biochem Behav. 2005;82(4):6216.
Chen et al., "Development of pyrimidine-based inhibitors of Janus tyrosine kinase 3", Bioorganic & Medicinal Chemistry Letters 16 (2006) 5633-5638.
Choung et al., "4-(Isoxazol-3-yl)pyrimidines from Pryimidinyl Nitrile Oxides", Synlett, Jan. 1, 2008, vol. 19, pp. 3036-3040.
Chudasama et al., "Integrative genomic and transcriptomic analysis of leiomyosarcoma." Nat Commun 2018;9(1):144.
Daniel Moser et al., "Dual-Target Virtual Screening by Pharmacophore Elucidation and Molecular Shape Filtering", ACS Medicinal Chemistry Letters, 2012, vol. 3 (2), p. 155-158.
Dey et al., "Evaluating the Mechanism and Therapeutic Potential of PTC-028, a Novel Inhibitor of BMI-1 Function in Ovarian Cancer," Molecular Cancer Therapeutics (Jan. 2018), 17(1):39-49.
Eberle-Singh, "Effective Delivery of a Microtubule Polymerization Inhibitor Synergizes with Standard Regimens in Models of Pancreatic Ductal Adenocarcinoma," Clin Cancer. Res (Sep. 15, 2019), 25(18), Supplementary Data: Supplementary Methods and Figures 1-7.
Examiner's Search Strategy and Results in U.S. Appl. No. 15/038,039, dated May 5, 2017, 139 results, 805 pages.
Excerpts from "Examiner's Search Strategy and Results in U.S. Appl. No. 15/038,039, dated May 5, 2017, 139 results, 805 pages", dated Nov. 13, 2017, 6 pages.
Fujii et al., "Sphere-forming stem-like cell populations with drug resistance in human sarcoma cell lines." Int J Oncol 2009;34(5):1381-1386.
Galmozzi et al.,"Cancer stem cells and therapeutic perspectives." Curr Med Chem 2006;13(6):603-607.
Gua et al. "Mel-18, a Polycomb Group Protein, Regulates Cell Proliferation and senescence via Transcriptional Repression of Bmi-1 and c-Myc Oncoproteins." Molecular Biology of the Cell 18, (2007): 536-546.
Higgins et al., "Release and actions of adenosine in the central nervous system." Pharm World Sci 1994;16(2):62-68.
Huang et al., "Fundamental aspects of solid dispersion technology for poorly soluble drugs." ACTA Pharmaceutical Sinica, vol. 4, No. 1, pp. 18-25, Jan. 1, 2014.
Jin et al., "Targeting glioma stem cells through combined BMI1 and EZH inhibition," Nature Medicine (Nov. 2017), 23(11):1352-1361.
Johns et al., "Pyrazolopyridine antiherpetics: SAR of C2' and C7 amine substituents." Bioorg. Med. Chem., 2005, vol. 13, pp. 2397-2411.
Johns et al., "Pyrazolo[5-a]pyridines: synthetic approaches to a novel class of Antiherpetics", Tetrahedron, Nov. 3, 2003, vol. 59(45):9001-9011.
Junji Miyata et al., "Orally available pyridinylpyrimidine derivatives as novel RANKL-induced osteoclastogenesis inhibitors", Bioorganic & Medicinal Chemistry Letters, 2012, vol. 22 (17), p. 5681-5684.
Kaplan et al., "Proteasome inhibitors in cancer therapy: Treatment regimen and peripheral neuropathy as a side effect", Free Radical Biology and Medicine, vol. 103, pp. 1-13, available online Dec. 8, 2016.
Kaplan et al., "Adenosine A1 antagonism attenuates atropine-resistant hypoxic bradycardia in rats." Acad Emerg Med 2003;10(9):923-930.
Kassis et al., "Synthesis and biological evaluation of new 3-(6-hydroxyindol-2-yl)-5-(Phenyl) pyridine or pyrazine V-Shaped molecules as kinase inhibitors and cytotoxic agents", European Journal of Medicinal Chemistry, 2011, vol. 46, pp. 5416-5434.

Kawai et al., "Systemic Therapy for Soft Tissue Sarcoma: Proposals for the Optimal Use of Pazopanib, Trabectedin, and Eribulin." Adv Ther 2017;34(7):1556-1571.
Kirk E. Hevener et al., "Discovery of a Novel and Potent Class of F. tularensis Enoyl-Reductase (Fabl) Inhibitors by Molecular Shape and Electrostatic Matching", Journal of Medicinal Chemistry, Jan. 12, 2012, vol. 55 (1), p. 268-279.
Lee PJ et al., "Spectrum of mutations in leiomyosarcomas identified by clinical targeted next-generation sequencing." Exp Mol Pathol 2017;102(1):156-161.
Leysen et al., "Risperidone: a novel antipsychotic with balanced serotonin-dopamine antagonism, receptor occupancy profile, and pharmacologic activity." J Clin Psychiatry 1994;55 Suppl:5-12.
Li et al. A practical strategy for the synthesis of 2-dialkylamino-4-arylamino-6-aminopyrimidines. Tetrahedron Lett. 50, pp. 5888-5893 (2009).
Liangxian Cao et al., "Targeting of Hematologic Malignancies with PTC299, A Novel Potent Inhibitor of Dihydroorotate Dehydrogenase with Favorable Pharmaceutical Properties", Molecular Cancer Therapeutics, vol. 18, No. 1, pp. 3-16, Oct. 23, 2018.
Maeda et al., "Targeting of BMI-1 expression by the novel small molecule PTC596 in mangle cell lymphoma." Oncotarget (2018), 9(47):28547-28560.
Makinen et al., "Exome Sequencing of Uterine Leiomyosarcomas Identifies Frequent Mutations in TP53, ATRX, and MED12." PloS Genet 2016;12(2):e1005850.
Molofsky et al., "Bmi-1 dependence distinguishes neural stem cell self-renewal from progenitor proliferation." Nature 2003;425(6961):962-967.
Morissette et al., "High-throughput crystallization: polymorphs, salts, co-crystals and solvates of pharmaceutical solids", Adv. Drug Delivery Rev., 2004, vol. 56, pp. 275-300.
Sirisoma et al., "Discovery of substituted 4-anilino-2-arylpyrimidines as a new series of apoptosis inducers using a cell-and caspase-based high throughput screening assay. 2. Structure-activity relationships of the 2-aryl group", Bioorg. Med. Chem. Lett. 19, 2009, 2305-2309.
Nishida et al., "The novel BMI-1 inihibitor PTC596 downregulates MCL-1 and induces p53-independent mitochondrial apoptosis in acute myeloid leukemia progenitor cells," Blood Cancer Journal (2017), 7(e527):1-9.
Ohtaka et al., "Bmi1 Inhibitors Suppress Cell Growth and Notch Signalling Of Acute Leukemia Cells", Experimental Hematology, 2017, vol. 53, p. S63, Abstract 3032.
Patani et al., "Bioisosterism: A Rational Approach in Drug Design", Chem Rev, 1996, vol. 96, pp. 3147-3176.
Paul et al., "Preparation of Substituted N-Phenyl-4-aryl-2-pyrimidinamines as Mediator Release Inhibitors", Journal of Medicinal Chemistry, Sep. 17, 1993, vol. 36(19):216-2725.
Phuong et al., "Design and synthesis of a novel pyrrolidinyl pyrido pyrimidinone derivative as a potent inhibitor of PI3Kαand mTOR", Bioorganic & Medicinal Chemistry Letters, 2012, vol. 22 (15), p. 5098-5103.
Reid et al., "Metabolic activation of dacarbazine by human cytochromes P450: the role of CYP1A1, CYP1A2, and CYP2E1." Clin Cancer Res 1999;5(8):2192-2197.
Rouhi, Chem. & Eng. News, dated Feb. 24, 2003, vol. 81 (8), pp. 32-35.
Sabat et al., "The Development of 2-Benzimidazole Substituted Pyrimidine Based Inhibitors of Lymphocyte Specific Kinase (Lck)", Bioorganic & Medicinal Chemistry Letters, Sep. 25, 2006, vol. 16(23):5973-5977.
Sagi et al., "Synthesis and biological evaluation of novel pyrimidine derivatives as sub-micromolar affinity ligands of GaIR2", Bioorganic & Medicinal Chemistry Letters, Sep. 12, 2011, vol. 1(23):7210-7215.
Shapiro et al., "Guanamines. IV. Pyridylguanamines", J. Org. Chem., 1960, vol. 25(3):384-387.
Sirisoma et al., "Discovery of substituted 4-anilino-2-(2-pyridyl)pyrimidines as a new series of apoptosis inducers using a cell- and caspase-based high throughput screening assay. Part 1: Structure-activity relationships of the 4-anilino group", Bioorganic & Medicinal Chemistry, Aug. 21, 2006, vol. 14(23):7761-7773.

(56) References Cited

OTHER PUBLICATIONS

Supporting Information (2 parts, pp. 1-54) for Whitten et al., "Rapid Microscale Synthesis, a New Method for Lead Optimization Using Robotics and Solution Phase Chemistry: Application to the Synthesis and Optimization of Corticotropin-Releasing Factor1 Receptor Antagonists", 1996, vol. 39(22):4354-4357.
Suzuki et al., Structure-Activity Relationships of Pyrazine-Based CK2 Inhibitors: Synthesis and Evaluation of 2,6-Disubstituted Pyrazines and 4,6-DisubstitutedPyramidines. Archiv der Pharmazie 341(9):554-561, 2008. Abstract only.
Thirumurthy Madhavan et al., "3D-QSAR studies of JNK1 inhibitors utilizing various alignment methods", 2011, Chemical Biology & Drug Design, vol. 79 (1), p. 53-67.
V. Chubanov et al., "Natural and synthetic modulators of SK (Kca2) potassium channels inhibit magnesium-dependent activity of the kinase-coupled cation channel TRPM7", 2012, British Journal of Pharmacology, vol. 166, pp. 1357-1376.
Vilchis-Reyes et al., "Synthesis and cytotoxic activity of 2-methylimidazo[1,2-a]pyridine- and quinoline-substituted 2-aminopyrimdine derivatives", European Journal of Medicinal Chemistry, 2010, vol. 45, pp. 379-386.
Weyermann et al., "Orally available selective melanocortin-4 receptor antagonists stimulate food intake and reduce cancer-induced cachexia in mice." PLoS One 2009;4(3):e4774.
Whitten et al., "Rapid Microscale Synthesis, a New Method for Lead Optimization Using Robotics and Solution Phase Chemistry: Application to the Synthesis and Optimization of Corticotropin-Releasing Factor Receptor Antagonists", 1996, J. Med. Chem., vol. 39, pp. 4354-4357.
Williams et al., Foye's Principles of Medicinal Chemistry, Fifth Edition, 2002, pp. 59-63.
Srikanth, 2011 PhD Thesis: "Synthesis of Bisindole Conjugates and 2-Anilinonicotinyl Linked Oxadiazoles/2-Aminobenzothiazoles/Triazolobenzothiadiazines as Potential Anticancer Agents", Acharya Nagarjuna University, Jun. 2011.
Alizadeh et al. "Distinct types of diffuse large B-cell lymphoma identified by gene expression profiling." Nature 403, No. 6769 (2000): 503-511.
Dutton et al. "Bmi-1 is induced by the Epstein-Barr virus oncogene LMP1 and regulates the expression of viral target genes in Hodgkin lymphoma cells." Blood 109, No. 6 (2007): 2597-2603.
Richter et al. "Long-term results of partial pancreaticoduodenectomy for ductal adenocarcinoma of the pancreatic head: 25-year experience." World Journal of Surgery 27 (2003): 324-329.
Quesnel et al. "p16$^{ink4a}$ gene and hematological malignancies." Leukemia & lymphoma 22, No. 1-2 (1996): 11-24.
Scheijen et al., "Characterization of pal-1, a common proviral insertion site in murine leukemia virus-induced lymphomas of c-myc and Pim-1 transgenic mice." Journal of virology 71, No. 1 (1997): 9-16.
Spike et al. "The Rb tumor suppressor in stress responses and hematopoietic homeostasis." Cell cycle 4, No. 1 (2005): 42-45.
Breuer et al. "Expression of the p16INK4a gene product, methylation of the p16INK4a promoter region and expression of the polycomb-group gene BMI-1 in squamous cell lung carcinoma and premalignant endobronchial lesions." Lung cancer 48, No. 3 (2005): 299-306.
Hans et al. "Confirmation of the molecular classification of diffuse large B-cell lymphoma by immunohistochemistry using a tissue microarray." Blood 103, No. 1 (2004): 275-282.
Dukers et al. "Unique polycomb gene expression pattern in Hodgkin's lymphoma and Hodgkin's lymphoma-derived cell lines." The American journal of pathology 164, No. 3 (2004): 873-881.
Dobin et al. "STAR: ultrafast universal RNA-seq aligner." Bioinformatics 29, No. 1 (2013): 15-21.
Hurt et al. "CD44+ CD24− prostate cells are early cancer progenitor/stem cells that provide a model for patients with poor prognosis." British journal of cancer 98, No. 4 (2008): 756-765.
Van Kemenade et al. "Coexpression of BMI-1 and EZH2 polycomb-group proteins is associated with cycling cells and degree of malignancy in B-cell non-Hodgkin lymphoma." Blood, The Journal of the American Society of Hematology 97, No. 12 (2001): 3896-3901.
Raaphorst et al. "Coexpression of BMI-1 and EZH2 polycomb group genes in Reed-Sternberg cells of Hodgkin's disease." The American journal of pathology 157, No. 3 (2000): 709-715.
Raaphorst et al. "Site-specific expression of polycomb-group genes encoding the HPC-HPH/PRC1 complex in clinically defined primary nodal and cutaneous large B-cell lymphomas," The American journal of pathology 164, No. 2 (2004): 533-542.
Raaphorst et al. "Correspondence re: S. Beá et al., BMI-1 Gene Amplification and Overexpression in Hematological Malignancies Occur Mainly in Mantle Cell Lymphomas." Cancer research 62, No. 2 (2002): 618-618.
Zhang et al., "Correlations of BMI-1 expression and telomerase activity in ovarian cancer tissues." *Experimental oncology* (2008).
Van Gosliga et al. "Establishing long-term cultures with self-renewing acute myeloid leukemia stem/progenitor cells." Experimental hematology 35, No. 10 (2007): 1538-1549.
Dimri et al. "The Bmi-1 oncogene induces telomerase activity and immortalizes human mammary epithelial cells." Cancer research 62, No. 16 (2002): 4736-4745.
Glinsky et al. "Microarray analysis identifies a death-from-cancer signature predicting therapy failure in patients with multiple types of cancer." The Journal of clinical investigation 115, No. 6 (2005): 1503-1521.
Burris et al. "Improvements in survival and clinical benefit with gemcitabine as first-line therapy for patients with advanced pancreas cancer: a randomized trial." Journal of clinical oncology 15, No. 6 (1997): 2403-2413.
Cui et al. "Bmi-1 is essential for the tumorigenicity of neuroblastoma cells." The American journal of pathology 170, No. 4 (2007): 1370-1378.
Koga et al. "A human homolog of Drosophila lethal (3) malignant brain tumor (I (3) mbt) protein associates with condensed mitotic chromosomes." *Oncogene* 18, No. 26 (1999): 3799-3809.
Xiong et al., "Cytotoxic chemotherapy for pancreatic cancer: Advances to date and future directions." Drugs 66 (2006): 1059-1072.
Vékony et al. "High expression of Polycomb group protein EZH2 predicts poor survival in salivary gland adenoid cystic carcinoma." Journal of clinical pathology 61, No. 6 (2008): 744-749.
Wang et al. "Increased polycomb-group oncogene Bmi-1 expression correlates with poor prognosis in hepatocellular carcinoma." Journal of cancer research and clinical oncology 134 (2008): 535-541.
Hänzelmann et al. "GSVA: gene set variation analysis for microarray and RNA-seq data." BMC bioinformatics 14 (2013): 1-15.
Hingorani et al. "Preinvasive and invasive ductal pancreatic cancer and its early detection in the mouse." Cancer cell 4, No. 6 (2003): 437-450.
Engelsen et al., "Low BMI-1 expression is associated with an activated BMI-1-driven signature, vascular invasion, and hormone receptor loss in endometrial carcinoma", Br J Cancer; May 20, 2008; 98(10):1662-9.
Arnes et al., "Independent prognostic value of the basal-like phenotype of breast cancer and associations with EGFR and candidate stem cell marker BMI-1", Histopathology, Feb. 2008; 52(3):370-80.
Van Galen et al., "Expression of the polycomb-group gene BMI1 is related to an unfavourable prognosis in primary nodal DLBCL", Journal of Clinical Pathology. 2007;60:167-172.
Kim et al., "Overexpression of Bmi-1 oncoprotein correlates with axillary lymph node metastases in invasive ductal breast cancer", The Breast, Oct. 2004; 13(5):383-388.
Kim et al., "The bmi-1 oncoprotein is overexpressed in humancolorectal cancer and correlates with the reduced p16ink4a/p14arf proteins", Cancer Lett, Jan. 2004; 203(2):217-224.
Liu et al. "Bmi-1 expression predicts prognosis for patients with gastric carcinoma." Journal of surgical oncology 97, No. 3 (2008): 267-272.
Jacobs et al. "Bmi-1 collaborates with c-Myc in tumorigenesis by inhibiting c-Myc-induced apoptosis via INK4a/ARF." Genes & development 13, No. 20 (1999): 2678-2690.

(56) References Cited

OTHER PUBLICATIONS

Jacobs et al. "The oncogene and Polycomb-group gene bmi-1 regulates cell proliferation and senescence through the ink4a locus." Nature 397, No. 6715 (1999): 164-168.
Adams et al. J. M., and S. Cory. "Oncogene co-operation in leukaemogenesis." Cancer Surveys 15 (1992): 119-141.
Wei et al. "Role of Bmi1 in H2A ubiquitylation and Hox gene silencing." Journal of Biological Chemistry 281, No. 32 (2006): 22537-22544.
Yang et al. "Bmi-1 is a target gene for SALL4 in hematopoietic and leukemic cells." Proceedings of the National Academy of Sciences 104, No. 25 (2007): 10494-10499.
Jonkers et al. "Synergistic tumor suppressor activity of BRCA2 and p53 in a conditional mouse model for breast cancer." Nature genetics 29, No. 4 (2001): 418-425.
Huang et al. "Association of Bmi-1 mRNA expression with differentiation, metastasis and prognosis of gastric carcinoma." Nan fang yi ke da xue xue bao, Journal of Southern Medical University 27, No. 7 (2007): 973-979. (English Abstract only).
Mihara et al., "Bmi-1 is useful as a novel molecular marker for predicting progression of myelodysplastic syndrome and patient prognosis." Blood 107, No. 1 (2006): 305-308.
Mihara et al. "Exacerbation of acute leukemia bearing isolated i (17q) along with proliferation of blasts with high BMI-1 expression." [Rinsho Ketsueki] The Japanese Journal of Clinical Hematology 48, No. 8 (2007): 659-663.
Nowak et al. "BMI1 is a target gene of E2F-1 and is strongly expressed in primary neuroblastomas." Nucleic acids research 34, No. 6 (2006): 1745-1754.
Song et al. "Bmi-1 is a novel molecular marker of nasopharyngeal carcinoma progression and immortalizes primary human nasopharyngeal epithelial cells." Cancer research 66, No. 12 (2006): 6225-6232.
Liu et al. "Loss of the human polycomb group protein BMI1 promotes cancer-specific cell death." Oncogene 25, No. 31 (2006): 4370-4375.
Van Lohuizen et al. "Identification of cooperating oncogenes in Eµ-myc transgenic mice by provirus tagging." Cell 65, No. 5 (1991): 737-752.
Van Lohuizen et al. "Sequence similarity between the mammalian bmi-1 proto-oncogene and the Drosophila regulatory genes Psc and Su(z)2." Nature 353, No. 6342 (1991): 353-355.
Lawrence et al. "Software for computing and annotating genomic ranges.", PLoS Computational Biology, (2013): 9:e1003118.
Lessard et al. "Bmi-1 determines the proliferative capacity of normal and leukaemic stem cells." nature 423, No. 6937 (2003): 255-260.
Liberzon et al. "Molecular signatures database (MSigDB) 3.0." Bioinformatics 27, No. 12 (2011): 1739-1740.
Love et al. "Moderated estimation of fold change and dispersion for RNA-seq data with DESeq2." Genome Biol 15 (2014): 550.
Chowdhury et al. "Expression of Polycomb-group (PcG) protein BMI-1 predicts prognosis in patients with acute myeloid leukemia." Leukemia 21, No. 5 (2007): 1116-1122.
Courel et al., "E2f6 and Bmi1 cooperate in axial skeletal development." Developmental dynamics: an official publication of the American Association of Anatomists 237, No. 5 (2008): 1232-1242.
Alkema et al. "Characterization and chromosomal localization of the human proto-oncogene BMI-1." Human molecular genetics 2, No. 10 (1993): 1597-1603.
Kang et al. "Elevated Bmi-1 expression is associated with dysplastic cell transformation during oral carcinogenesis and is required for cancer cell replication and survival." British Journal of Cancer 96, No. 1 (2007): 126-133.
Lindstroem et al. "p14ARF homozygous deletion or MDM2 overexpression in Burkitt lymphoma lines carrying wild type p53." Oncogene 20, No. 17 (2001): 2171-2177.
Sánchez-Beato et al. "Abnormal PcG protein expression in Hodgkin's lymphoma. Relation with E2F6 and NFκB transcription factors." The Journal of Pathology: A Journal of the Pathological Society of Great Britain and Ireland 204, No. 5 (2004): 528-537.
Sawa et al. "BMI-1 is highly expressed in M0-subtype acute myeloid leukemia." International journal of hematology 82 (2005): 42-47.
Kozakowskiet et al. "BMI-1 expression is inversely correlated with the grading of renal clear cell carcinoma." Pathology & Oncology Research 14 (2008): 9-13.
Olive et al., "Mutant p53 gain of function in two mouse models of Li-Fraumeni syndrome." Cell 2004;119:847-60
Gould, "Salt selection for basic drugs." International journal of pharmaceutics 33, No. 1-3 (1986): 201-217.
Park et al. "Bmi-1 is required for maintenance of adult self-renewing haematopoietic stem cells." Nature 423, No. 6937 (2003): 302-305.
Breuer et al.. "Increased expression of the EZH2 polycomb group gene in BMI-1-positive neoplastic cells during bronchial carcinogenesis." Neoplasia 6, No. 6 (2004): 736-743.
Küppers et al. "Cellular origin of human B-cell lymphomas." New England Journal of Medicine 341, No. 20 (1999): 1520-1529.
Reinisch et al. "BMI-1: a protein expressed in stem cells, specialized cells and tumors of the gastrointestinal tract." Histology and histopathology (2006).
Ritchie et al. "limma powers differential expression analyses for RNA-sequencing and microarray studies." Nucleic acids research 43, No. 7 (2015): e47-e47.
Beà et al. "Increased number of chromosomal imbalances and high-level DNA amplifications in mantle cell lymphoma are associated with blastoid variants." Blood, The Journal of the American Society of Hematology 93, No. 12 (1999): 4365-4374.
Beà et al. "BMI-1 gene amplification and overexpression in hematological malignancies occur mainly in mantle cell lymphomas." Cancer research 61, No. 6 (2001): 2409-2412.
Berge et al. "Pharmaceutical salts." Journal of pharmaceutical sciences 66, No. 1 (1977): 1-19.
Faderl et al. "The prognostic significance of p16 INK4a/p14 ARF and p15 INK4b deletions in adult acute lymphoblastic leukemia." Clinical cancer research 5, No. 7 (1999): 1855-1861.
Faderl et al. "The incidence of chromosome 9p21 abnormalities and deletions of tumor suppressor genes p15 (INK4b)/p16 (INK4a)/p14 (ARF) in patients with acute lymphoblastic leukemia." Cytokines, cellular & molecular therapy 5, No. 3 (1999): 159-163.
Kuerbitz et al. "Deletion of p16INK4A/CDKN2 and p15 INK4B in Human Somatic Cell Hybrids and Hybrid-derived Tumors." Cell Growth & Differentiation (1999): 27-33.
S. K. Li et al., FoxM1C counteracts oxidative stress-induced senescence and stimulates Bmi expression. J Bio Chem, 2008 J. Biol. Chem. 283(24) Jun. 13, 2008:16545-53.2008.
Liu et al. "Hedgehog signaling and Bmi-1 regulate self-renewal of normal and malignant human mammary stem cells." Cancer research 66, No. 12 (2006): 6063-6071.
Vonlanthen et al. "The bmi-1 oncoprotein is differentially expressed in non-small cell lung cancer and correlates with INK4A-ARF locus expression." British journal of cancer 84, No. 10 (2001): 1372-1376.
Bruggeman et al. "Bmi1 controls tumor development in an Ink4a/Arf-independent manner in a mouse model for glioma." Cancer cell 12, No. 4 (2007): 328-341.
Subramanian et al. "Gene set enrichment analysis: a knowledge-based 15 approach for interpreting genome-wide expression profiles." Proceedings of the National Academy of Sciences 102, No. 43 (2005): 15545-15550.
Tuveson et al. "Endogenous oncogenic K-rasG12D stimulates proliferation and widespread neoplastic and developmental defects." Cancer cell 5, No. 4 (2004): 375-387.
Fernàndez et al. "Pathogenesis of mantle-cell lymphoma: all oncogenic roads lead to dysregulation of cell cycle and DNA damage response pathways." Journal of Clinical Oncology 23, No. 26 (2005): 6364-6369.
Häyry et al. "Copy number alterations of the polycomb gene BMI1 in gliomas." Acta neuropathologica 116 (2008): 97-102.
Häyry et al. "Stem cell protein BMI-1 is an independent marker for poor prognosis in oligodendroglial tumours." Neuropathology and applied neurobiology 34, No. 5 (2008): 555-563.

(56) References Cited

OTHER PUBLICATIONS

Dik et al. "CALM-AF10+ T-ALL expression profiles are characterized by overexpression of HOXA and BMI1 oncogenes." Leukemia 19, No. 11 (2005): 1948-1957.
Datta et al. "Bmi-1 cooperates with H-Ras to transform human mammary epithelial cells via dysregulation of multiple growth-regulatory pathways." Cancer research 67, No. 21 (2007): 10286-10295.
De Boer et al. "Analysing gene expressions with GRANK." Bioinformatics 19, No. 15 (2003): 2000-2001.
Wiederschain et al. "Contribution of polycomb homologues Bmi-1 and Mel-18 to medulloblastoma pathogenesis." Molecular and cellular biology 27, No. 13 (2007): 4968-4979.
Haupt et al. "Nucleotide sequence of bup, an upstream gene in the bmi-1 proviral insertion locus." Molecular biology reports 17 (1993): 17-20.
Haupt et al. "bmi-1 transgene induces lymphomas and collaborates with myc in tumorigenesis." Oncogene 8, No. 11 (1993): 3161-3164.
Yang et al. "Genetic aberrations in soft tissue leiomyosarcoma." Cancer letters 275, No. 1 (2009): 1-8.
Nagai et al., "The preclinical activities of PTC596, a novel tubulin binding agent that down-regulates BMI1, alone and in combination with bortezomib in multiple myeloma." Blood 134 (2019): 4414.
Nagai et al., "The combination of the tubulin binding small molecule PTC596 and proteasome inhibitors suppresses the growth of myeloma cells." Scientific Reports 11, No. 1 (2021): 2074.
Freeman-Cook et al., "Expanding Control of the Tumor Cell Cycle with a CDK2/4/6 Inhibitor," Cancer Cell, vol. 39, No. 10, Oct. 11, 2021, pp. 1404-1421.
Caudell et al., "The role of CALM-AF10 gene fusion in acute leukemia", Leukemia, vol. 22(4):678-685, Apr. 2008.
Cao et al., "PTC299 is a Novel DHODH Inhibitor That Modulates VEGFA mRNA Translation and Inhibits Proliferation of a Broad Range of Leukemia Cells", Blood, vol. 130, S. 1, p. 1371, 2017.
Ferdinando De Vita et al., "NAB-paclitaxel and gemcitabine in metastatic pancreatic ductal adenocarcinoma (PDAC): from clinical trials to clinical practice," BMC Cancer, 16:709 (2016).
Von Hoff et al., "Increased Survival in Pancreatic Cancer with nab-Paclitaxel Plus Gemcitabine", *The New England Journal of Medicine*, Oct. 31, 2013, vol. 369(18):1691-1703.
Bolomsky A. et al., "The first-in-class BMI-1 Modulators PTC-028 and PTC596 display potent activity in pre-clinical models of multiple myeloma", Clinical Lymphoma, Myeloma and Leukemia—17th International Myeloma Workshop, vol. 19, No. 10, Supplement, Oct. 1, 2019.
Bolomsky A. et al., "Targeting of BMI-1 with PTC-209 Shows Potent Anti-Myeloma Activity and Impairs the Tumor Microenvironment", J. Hematol. Oncol., vol. 9, Issue 17, Mar. 2, 2016.
Third Party Opposition in counterpart Colombian Patent Application No. NC2021/0011836.
Third Party Opposition in counterpart Ecuadorian Patent Application No. SENADI-2021-67104.
Clinicaltrials.gov, "A Study of PTC596 in Combination With Dacarbazine in Participants With Advanced Leiomyosarcoma (LMS)", printed Mar. 27, 2020.
Grenader et al., "Long-term response to pegylated liposomal doxorubicin in patients with metastatic soft tissue sarcomas", *Anti-Cancer Drugs*; vol. 20, No. 1, pp. 15-20; 2009.
Jernigan et al., "Preclinical and Early Clinical Development of PTC596, a Novel Small-Molecule Tubulin-Binding Agent," Molecular Cancer Therapeutics, vol. 20(10), pp. 1846-1857, Oct. 2021.
Van Tine et al., "A phase 1b study of unesbulin (PTC596) plus dacarbazine for the treatment of patients with locally recurrent, unresectable, or metastatic relapsed/refractory leiomyosarcoma," Jun. 1, 2022, American Society of Clinical Oncology; Annual Meeting Abstract; Sarcoma; p. 11507.
Weetall et al., "Abstract 292: PTC596 combination therapy for sarcoma," Cancer Research, vol. 79, No. 13_Supplement, Jul. 1, 2019, p. 292.
Liew et al., "SVM Model for Virtual Screening of Lck Inhibitors," Journal of Chem. Information and Modeling, 2009, 49(4), pp. 877-885.
CAS Reg. No. 1333859-55-4, Sep. 29, 2011.
Sun Jihui, Medicinal Chemistry, People's Medical Publishing House, p. 426 (Nov. 31, 1986).
Zhang Xingsheng, Pharmaceutics, China Light Industry Press, pp. 466-470, Apr. 30, 2004.
Liu Wen, Pharmaceutical Polymer Material Science, China Press of Traditional Medicine, pp. 94-96, Jul. 31, 2017.
Pan Weisan, Industrial Pharmacy, China Medical Science and Tech. Press Pub., p. 364 (Jun. 30, 2010).
International Search Report for PCT/US2019/046972, mailed May 29, 2020.
Written Opinion of the International Searching Authority in PCT/US2019/046972, mailed May 29, 2020.
Eberle et al., "Abstract A22: Preclinical evaluation of Bmi1 inhibition in pancreatic ductal adenocarcinoma", Mol Cancer Res., vol. 14, Issue 11 Supplement: A22, Nov. 1, 2016.
Eberle-Singh et al., "Delineating the function, efficacy, and mechanism of a novel preclinical agent for the treatment of pancreatic ductal adenocarcinoma," Columbia Academic Commons, Doctoral Thesis; 2018.
Chiaravalli et. al., "Pancreatic ductal adenocarcinoma: State-of-the-art 2017 and new therapeutic strategies," Cancer Treatment Reviews, vol. 60, 2017, pp. 32-43.
Eberle-Singh et. al., "Effective Delivery of a Microtubule Polymerization Inhibitor Synergizes with Standard Regimens in Models of Pancreatic Ductal Adenocarcinoma," Clin Cancer. Res (Sep. 15, 2019), 25(18): S548-S560.
Hiroshi Ueda, "Importance of Evaluation of Physical Properties of Solid Preparations in Development of Amorphous Drugs," Farumashia, vol. 52, No. 5, pp. 392-396 (2016), released online May 1, 2016.
Lian Yu, "Amorphous pharmaceutical solids: preparation, characterization and stabilization," Advance Drug Delivery Reviews, vol. 48 issue 1 (2001) available online Apr. 20, 2001, pp. 27-42.
Unesbulin (PTC596) 99.91%(HPLC) Selleck BMI-1 inhibitor. (n.d.). selleckchem.com. (Year: 2020).
PTC299: Inhibitor of dihydroorotate dehydrogenase (DHODH) and VEG FA mRNA translation. (n.d.). https://www.medchemexpress.com/ptc299.html. (Year: 2024).
Etsuo Yonemochi, "Importance of Bulk State Analysis in Active Pharmaceutical Ingredients and Formulations," SCAS News, 2004-II, 3-6.
Isao Sugimoto et al., "Solvates, Amorphous Solids, and Pharmaceutical Formulations*," Journal of the Society of Powder Technology, Japan 1985, vol. 22, No. 2, p. 85-97.
Bruno C. Hancock, et al., "Molecular Mobility of Amorphous Pharmaceutical Solids Below Their Glass Transition Temperatures," Pharmaceutical Research, 1995, vol. 12 no. (6), pp. 799-806.
Bruno C. Hancock et al., "Characteristics and Significance of the Amorphous State in Pharmaceutical Systems," Journal Of Pharmaceutical Sciences, Jan. 1997, vol. 86, No. 1, pp. 1-12.
Federal Law "On the fundamentals of protecting the health of citizens in the Russian Federation" dated Nov. 21, 2011 N 323-FZ (latest edition), subparagraph 8, article 2.
Pubchem, Substance Record for SID 74223469, Jun. 9, 2014, "5-Fluoro-2-(6-fluoro-2-methyl-1Hbenzo[d]imidazol-1-yl)-N4-(4-(trifluoromethyl)phenyl)pyrimidine-4,6-diamine.".

* cited by examiner

METHOD FOR TREATING PANCREATIC CANCER

CROSS-REFERENCE TO RELATED APPLICATIONS

This application is a U.S. National Stage filing under 35 U.S.C. § 371 of International Application No. PCT/US2019/046972, filed Aug. 17, 2019, which in turn claims the benefit of U.S. Provisional Application No. 62/719,526, filed Aug. 17, 2018, the entire contents of which are incorporated by reference herein.

STATEMENT REGARDING FEDERALLY SPONSORED RESEARCH OR DEVELOPMENT

This invention was made with government support under CA188857 awarded by the National Institutes of Health. The government has certain rights in the invention.

INTRODUCTION

A method for treating pancreatic cancer in a subject in need thereof comprising, administering to the subject an effective amount of a tubulin polymerization inhibitor compound is described herein. More particularly, a method for treating pancreatic ductal adenocarcinoma in a subject in need thereof comprising, administering to the subject an effective amount of a substituted reverse pyrimidine tubulin polymerization inhibitor compound alone or in combination with other chemo-therapeutic agents is described herein.

BACKGROUND

An estimated 55,440 Americans will be diagnosed with pancreatic cancer in 2018, the fifth most common cause of cancer-related mortality; these figures are predicted to rise over the next decade. Pancreatic ductal adenocarcinoma (PDA) is a highly chemo-resistant cancer responsible for more than 45,000 deaths annually, accounting for about 93% of pancreatic tumors. Despite some measurable progress in recent years, PDA remains a largely intractable cancer, with a median survival of less than six months and a 5-year survival rate of just 8.7%.

Several factors contribute to this poor prognosis. Most patients (85%) present with advanced disease, precluding them from the one effective intervention: surgical resection. However, even among those with locally confined disease who have had surgery, the 5-year and 10-year survival rates are just 25% and 8% respectively, due to high recurrence rates (A. Richter et al., World J Surg 27, 324, March 2003). For these remaining 85% of patients, as well as those with recurrent disease, there are few treatments available. The national standard-of-care therapy, gemcitabine modestly extends survival by a few weeks, approved primarily for improving quality-of-life indicators (H. A. Burris, 3rd et al., J Clin Oncol 15, 2403, June 1997). The only other FDA approved agent for advanced PDA is Tarceva, which provides an average of just 10 days additional benefit when combined with gemcitabine. Despite over 60 clinical trials of different agents and combinations (H. Q. Xiong, K. Carr, J. L. Abbruzzese, Drugs 66, 1059, 2006), no other effective therapies have been identified.

Among the most remarkable features of PDA is the presence of an expansive desmoplastic stroma that conditions the local microenvironment, generating high interstitial fluid pressure, poor vascularity, and diminished tissue perfusion and diffusion. Consequently, drug delivery to pancreatic tumors is less efficient than in normal tissues, contributing to the broad primary chemo-resistance that characterizes this disease. The broad resistance of PDA to cytotoxic therapy arises in part from this biophysical barrier to drug delivery.

Preclinical testing of chemo-therapeutic agents in the KPC (KrasLSL.G12D/+; p53R172H/+; PdxCretg/+) genetically engineered mouse model suggest that drug development efforts for PDA should focus on agents with a long half-life and a large therapeutic index (the range of concentrations between efficacy and toxicity) as a means of improving drug exposure. As well, drug stability and retention within tumor cells should also be considered in the design of new regimens for PDA.

Unfortunately, most traditional cytotoxic agents are rapidly cleared from circulation, are acutely toxic to normal proliferating tissues, are quickly metabolized, or are actively exported from tumor cells. An informative counterexample is nab-paclitaxel (Abraxane, Celgene), an albumin-bound form of the microtubule stabilizing agent paclitaxel that is FDA approved in combination with gemcitabine for metastatic pancreatic cancer patients. Nab-paclitaxel has a terminal half-life of 27 hours in circulation and is less toxic than unmodified paclitaxel. The success of this regimen helped to validate the importance of pharmacology in pancreatic cancer drug development and demonstrated the benefit of combining gemcitabine (a deoxycytidine analog) with a microtubule targeted agent.

Accordingly, there remains a need for chemo-therapeutic agents that overcome the PDA biophysical barrier to produce effective biodistribution into tumor tissues, have the requisite pharmacodynamic properties and combine synergistically with other chemo-therapeutic agents for the treatment of pancreatic cancer.

SUMMARY

Compound 1 is a small molecule anticancer agent, useful for inhibiting tubulin polymerization and BMI-1 protein function (see WO2014/081906), referred to as 5-fluoro-2-(6-fluoro-2-methyl-1H-benzo[d]imidazol-1-yl)-N4-[4-(trifluoromethyl)phenyl]pyrimidine-4,6-diamine, having the structure of Formula (I):

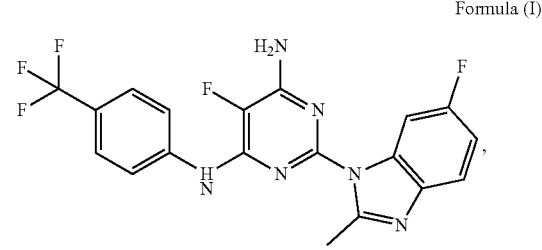 [SMILES: Cc1nc2ccc(F)cc2n1-c1nc(N)c(F)c(Nc2ccc(C(F)(F)F)cc2)n1]

Formula (I)

or a pharmaceutically acceptable salt or pharmaceutical composition thereof.

Compound 1 has demonstrated pharmacological properties, including along circulating half-life and lack of P-glycoprotein (PGP) substrate activity and effective biodistribution into tumor tissues. Further, Compound 1 had been shown to induce mitotic arrest and apoptosis in multiple PDA cell lines.

Through mechanistic studies, without being limited to any one particular theory, Compound 1 has been demonstrated to function as a microtubule polymerization inhibitor. In addition, Compound 1 combines synergistically with standard clinical regimens such as either or both gemcitabine and nab-paclitaxel to improve efficacy in patient derived xenograft models (PDX) yielding potent and durable cancer regression. Further, Compound 1 has demonstrated efficacy in combination with gemcitabine in the highly chemo-resistant genetically engineered KPC PDA mouse model.

These data and a demonstrated safety profile as an anti-cancer agent in clinical development demonstrate clear rationale for the development of Compound 1 in combination with standard-of-care chemotherapy for PDA.

DESCRIPTION

One aspect described herein includes a method for treating pancreatic cancer in a subject in need thereof comprising, administering to the subject an effective amount of Compound 1, 5-fluoro-2-(6-fluoro-2-methyl-1H-benzo[d]imidazol-1-yl)-N4-[4-(trifluoromethyl)phenyl]pyrimidine-4,6-diamine, having the structure of Formula (I):

Formula (I)

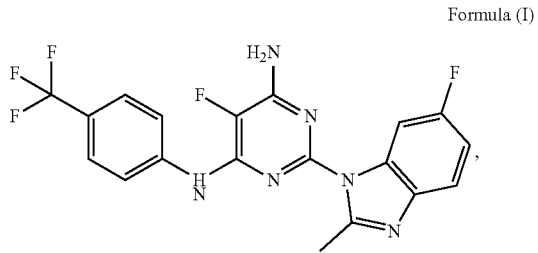 [SMILES: Cc1nc2ccc(F)cc2n1-c1nc(N)c(F)c(Nc2ccc(C(F)(F)F)cc2)n1]

or a pharmaceutically acceptable salt or pharmaceutical composition thereof.

Another aspect includes a method for treating pancreatic ductal adenocarcinoma in a subject in need thereof comprising, administering to the subject an effective amount of Compound 1 or a pharmaceutically acceptable salt or pharmaceutical composition thereof.

One aspect described herein includes a method for treating pancreatic cancer in a subject in need thereof comprising, administering to the subject an effective amount of Compound 1 or a pharmaceutically acceptable salt or pharmaceutical composition thereof in combination with an effective amount of one or more chemo-therapeutic agents.

Another aspect includes a method for treating pancreatic ductal adenocarcinoma in a subject in need thereof comprising, administering to the subject an effective amount of Compound 1 or a pharmaceutically acceptable salt or pharmaceutical composition thereof in combination with an effective amount of one or more chemo-therapeutic agents.

One aspect described herein includes a method for treating pancreatic ductal adenocarcinoma in a subject in need thereof comprising, administering to the subject an effective amount of Compound 1 or a pharmaceutically acceptable salt or pharmaceutical composition thereof in combination with an effective amount of either or both gemcitabine and nab-paclitaxel.

Another aspect includes a method for treating pancreatic ductal adenocarcinoma in a subject in need thereof comprising, administering to the subject an effective amount of Compound 1 or a pharmaceutically acceptable salt or pharmaceutical composition thereof in combination with an effective amount of either or both gemcitabine and nab-paclitaxel.

BRIEF DESCRIPTION OF THE DRAWINGS

FIGS. 1b, 1c and 1d show that Compound 1 demonstrates a dose and time-dependent effect in cell cycle arrest in human PDA cells.

FIGS. 2a and 2b show that Compound 1 demonstrates a dose and time-dependent increase in the amount of human PDA cells affected by polyploidy.

FIGS. 3a and 3b show relative to vehicle that Compound 1 demonstrates a time-dependent increase in cell biomarkers that indicate a corresponding increase in cell apoptosis.

FIG. 4a demonstrates that Compound 1 has a long plasma half-life and penetrates the CNS and distributes into brain tissues.

FIG. 4b shows that, compared to other chemotherapeutic agents that cause cell cycle arrest, Compound 1, Compound 2 and chlorpromazine do not function as a PGP substrate FIG. 5a shows that the improved efficacy of the combination is not due to a pharmacokinetic drug-drug interaction.

FIG. 5a shows that Compound 1 distributes into PDA tissues; and, FIGS. 5b and 5c show that Compound 1 demonstrates consistent reduction in Cyclin B1 relative to Vinculin suggesting a decrease in PDA cell mitotic progression induced by reduction in Cyclin B1 relative to Vinculin induced apoptosis.

FIGS. 6a, 6b, 6c, 6d, and 6e show that Compound 1 in combination with gemcitabine synergistically increases overall survival in the KPC mouse model; wherein, FIG. 6a shows that Compound 1 in combination with gemcitabine maintains relative KPC mouse body weight; FIG. 6b shows relative to vehicle, gemcitabine alone or Compound 1 alone, that Compound 1 in combination with gemcitabine simultaneously decreases tumor volume while synergistically increasing overall survival relative to each agent alone; FIGS. 6c, 6d, and 6e show relative to vehicle, gemcitabine alone or Compound 1 alone, that Compound 1 in combination with gemcitabine demonstrates an overall reduction in growth rate of PDA cells and certain cell biomarkers.

FIG. 7a shows relative to vehicle that Compound 1 demonstrates a time-dependent decrease in KPC mouse model PDA tumor volume; and, FIG. 7b shows, relative to gemcitabine alone or Compound 1 alone, that Compound 1 in combination with gemcitabine demonstrates an additive time-dependent decrease in KPC mouse PDA tumor volume.

FIG. 8a shows relative to vehicle, gemcitabine alone or Compound 1 alone, that Compound 1 in combination with gemcitabine demonstrates a reduction in KPC mouse PDA tumor growth; and, FIG. 8b shows, relative to vehicle and gemcitabine alone, that Compound 1 in combination with gemcitabine demonstrates a reduction in KPC mouse PDA-driven liver metastases.

FIG. 9a is an image of a stained tumor section from KPC mice treated with a combination of Compound 1 and gemcitabine (Cpd 1/GEM). FIG. 9a shows gemcitabine induced apoptotic cell population; and, FIG. 9b shows apoptotic cell population induced by Compound 1 in combination with gemcitabine; wherein Compound 1 in combination with gemcitabine demonstrates a markedly increased apoptotic cell population, suggesting a synergistic increase in apoptotic induction.

FIG. 10a shows relative vehicle and Vinculin expression that Compound 1 demonstrates a consistent reduction in BMI-1 protein expression in various cell types.

FIG. 10b shows relative to vehicle and the presence of J1002 that Compound 1 demonstrates a dose and time-dependent decrease in viability of cells dependent on BMI-1 protein expression.

FIG. 10c shows relative to vehicle treated cells that Compound 1 demonstrates sub-M activity toward reduction in BMI-1 protein expression in the presence of J1002.

FIGS. 10d, 10e, 10f, and 10g show relative to vehicle and the presence of J1002 that Compound 1 demonstrates a dose and time-dependent increase in the amount of BMI-1 dependent cells affected by polyploidy; wherein, the data taken as a whole suggest that Compound 1 induces BMI-1 hyperphosphorylation indirectly as a result of mitotic arrest.

FIGS. 11a and 11b show relative to vehicle, COL (carboplatin) and TAX (tamoxifen) that Compound 1 demonstrates a significant fold-change increase in prevention of tubulin formation.

FIGS. 11c and 11d show relative to vehicle that Compound 1 demonstrates a significant reduction in tubulin formation.

FIGS. 11e and 11f show relative to vehicle, COL (carboplatin) and TAX (tamoxifen) that Compound 1 demonstrates a dose-dependent decrease in tubulin polymerization; wherein, the data taken as a whole suggest that Compound 1 directly inhibits microtubule formation.

FIGS. 12a, 12b, 12c, and 12d show that Compound 1 in either or both dual combination with nab-paclitaxel and triple combination with gemcitabine and nab-paclitaxel synergistically decreases tumor volume and overall tumor growth in a human-derived xenograft model of PDA; wherein, FIG. 12a shows relative to vehicle, gemcitabine alone, Compound 1 alone, nab-paclitaxel alone, gemcitabine in combination with nab-paclitaxel and gemcitabine in combination with Compound 1 that Compound 1 in either or both dual combination with nab-paclitaxel and triple combination with gemcitabine and nab-paclitaxel synergistically decrease tumor volume; FIG. 12b shows relative to vehicle, gemcitabine alone, Compound 1 alone, nab-paclitaxel alone, gemcitabine in combination with nab-paclitaxel and gemcitabine in combination with Compound 1, Compound 1 in combination with nab-paclitaxel and Compound 1 in combination with both gemcitabine and nab-paclitaxel that all combinations synergistically maintain relative KPC mouse body weight; FIG. 12c shows relative to the presence or absence of any of gemcitabine, Compound 1 and nab-paclitaxel that Compound 1 in combination with either or both gemcitabine and nab-paclitaxel significantly decreases the overall rate of tumor growth while increasing the decay rate of tumor volume; and, FIG. 12d shows relative to the presence or absence of any of gemcitabine, Compound 1 and nab-paclitaxel that Compound 1 in combination with either or both gemcitabine and nab-paclitaxel significantly decreases initial tumor volume.

DEFINITIONS

Figure 1A:
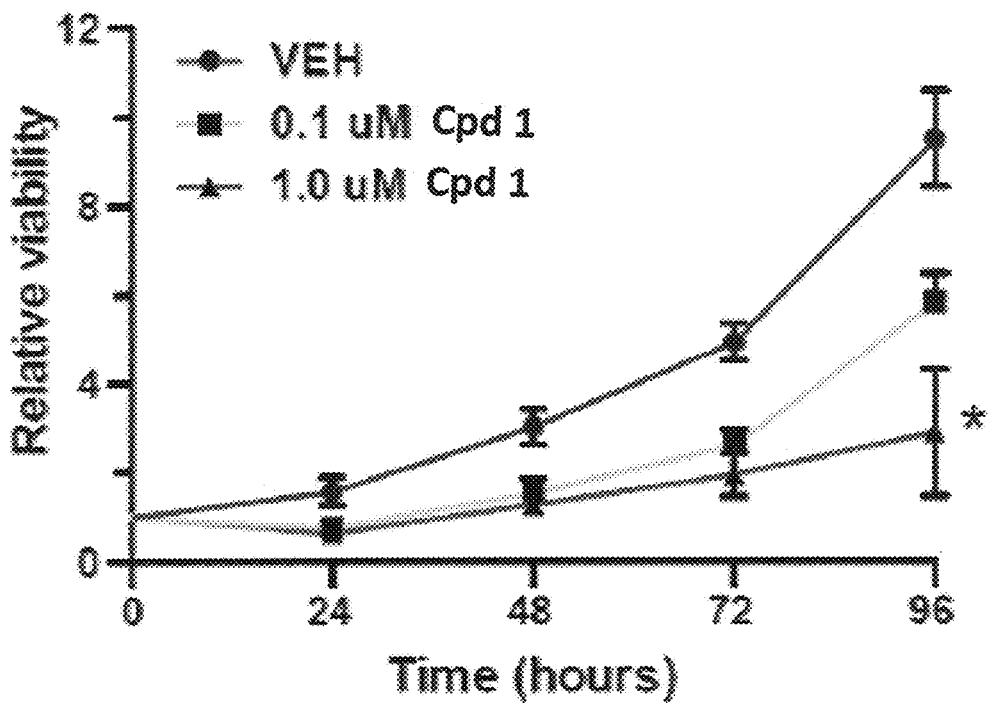
FIG. 1a is a graph of the relative Aspc1 cell viability over time following treatment with vehicle or Compound 1 (0.1 μM or 1.0 μM). The results show relative to vehicle that Compound 1 demonstrates a dose and time-dependent decrease in human PDA cell viability.
Figure 1B:
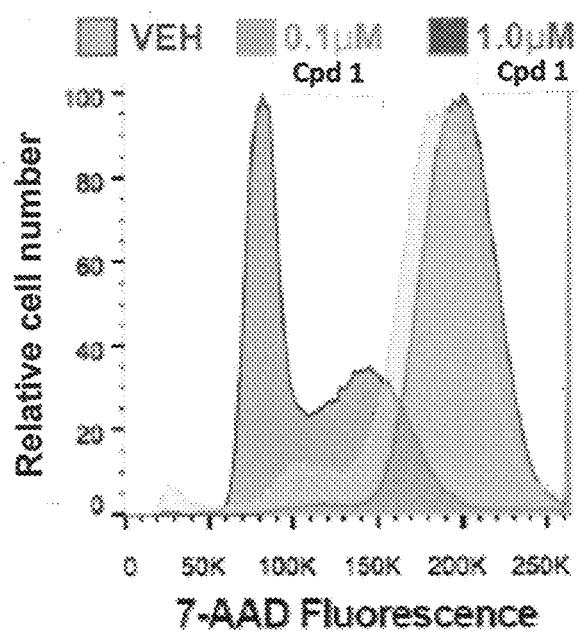
FIG. 1b depicts representative histograms of DNA content, measured by flow cytometry for 7-AAD fluorescence, from Aspc1 cells treated with vehicle or Compound 1 (0.1 μM or 1.0 μM).
Figure 1C:
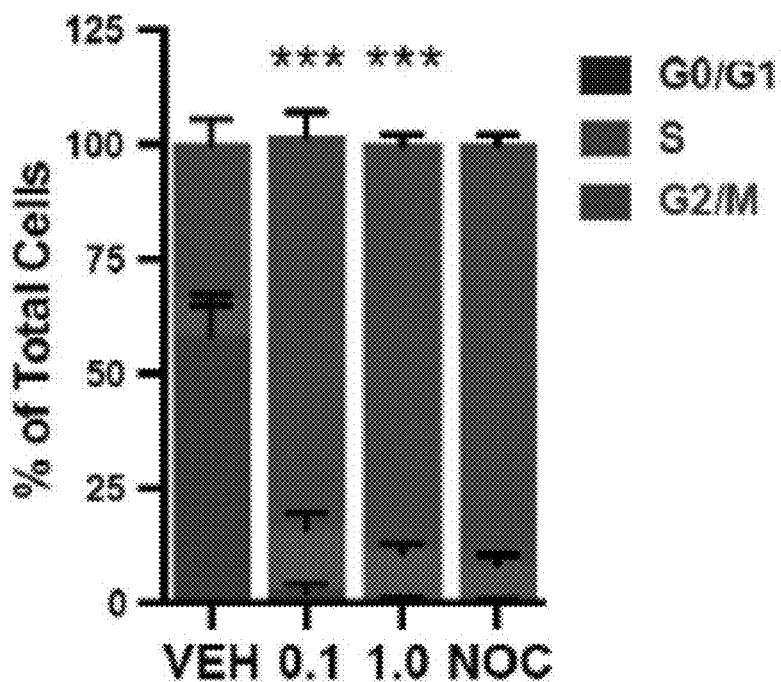
FIG. 1c is a graph of the percent of Aspc1 cells in G0/G1 phase, S phase, and G2/M phase following 24 hours after treatment with vehicle (DMSO), Compound 1 (0.1 μM, 1.0 μM), or 0.1 μM nocodazole (NOC, positive control).

As used herein, the term "about" means a range around a given value wherein the resulting value is substantially the same as the expressly recited value. In one aspect, "about" means within 25% of a given value or range. For example, the phrase "about 70% by weight" comprises at least all values from 52% to 88% by weight. In another aspect, the term "about" means within 10% of a given value or range. For example, the phrase "about 70% by weight" comprises at least all values from 63% to 77% by weight. In another aspect, the term "about" means within 7% of a given value or range. For example, the phrase "about 70% by weight" comprises at least all values from 65% to 75% by weight.

Concentrations, amounts, cell counts, percentages and other numerical values may be presented herein in a range format. It is to be understood that such range format is used merely for convenience and brevity and should be interpreted flexibly to include not only the numerical values explicitly recited as the limits of the range but also to include all the individual numerical values or sub-ranges encompassed within that range as if each numerical value and sub-range was explicitly recited.

As used herein, the terms "therapies" and "therapy" can refer to any protocol(s), method(s), compositions, formulations, and/or agent(s) that can be used in the prevention, treatment, management, or amelioration of a condition or disorder or one or more symptoms thereof (e.g., pancreatic cancer or one or more symptoms or one or more conditions associated therewith).

In certain aspects, the terms "therapies" and "therapy" refer to drug therapy such as chemotherapy, adjuvant therapy, radiation, surgery, biological therapy, supportive therapy, antiviral therapy and/or other therapies useful in treatment, management, prevention, or amelioration of a condition or disorder or one or more symptoms thereof (e.g., pancreatic cancer or one or more symptoms or one or more conditions associated therewith). In certain aspects, the term "therapy" refers to a therapy other than Compound 1 or a pharmaceutically acceptable salt or pharmaceutical composition thereof. In specific aspects, an "additional therapy" and "additional therapies" refer to a therapy other than a treatment using Compound 1 or a pharmaceutically acceptable salt or pharmaceutical composition thereof. In a specific aspect, a therapy includes the use of Compound 1 as an adjuvant therapy. For example, using Compound 1 in conjunction with a drug therapy such as chemotherapy, biological therapy, surgery, supportive therapy, antiviral therapy and/or other therapies useful in treatment, management, prevention, or amelioration of a condition or disorder or one or more symptoms thereof (e.g., pancreatic cancer or one or more symptoms or one or more conditions associated therewith).

As used herein, the term "human infant" refers to a newborn to 1 year old year human.

As used herein, the term "human toddler" refers to a human that is 1 year to 3 years old.

As used herein, the term "human child" refers to a human that is 1 year to 18 years old.

As used herein, the term "human adult" refers to a human that is 18 years or older.

As used herein, the term "middle-aged human" refers to a human between the ages of 30 and 64.

As used herein, the term "elderly human" refers to a human 65 years or older.

As used herein, the term "subject" refers to an individual being administered a therapy as described herein. In a specific aspect, the individual is a human.

As used herein, the term "pancreatic cancer" refers to pancreatic cancer generally as described herein. In a specific aspect, the general term pancreatic cancer may refer to a pancreatic ductal adenocarcinoma (PDA) without specifically using the term.

As used herein, the term "effective amount" in the context of administering Compound 1 to a subject having a pancreatic cancer refers to the dose of Compound 1 that results in a beneficial or therapeutic effect. In specific aspects, an "effective amount" of Compound 1 refers to an amount of Compound 1 which is sufficient to achieve at least one, two, three, four or more of the following beneficial or therapeutic effects: (i) inhibition of a pancreatic cancer; (ii) regression of the pancreatic cancer; (iii) eradication, removal, or complete remission of the pancreatic cancer; (iv) prevention of the development or onset of one or more symptoms associated with the pancreatic cancer; (v) reduction or amelioration of the severity of one or more symptoms associated with the pancreatic cancer; (vi) the reduction in the number of one or more symptoms associated with the pancreatic cancer; (vii) amelioration of the severity of one or more symptoms associated with the pancreatic cancer; (viii) reduction in the duration of one or more symptoms associated with the pancreatic cancer; (ix) prevention in the recurrence of proliferation or one or more symptoms associated with the pancreatic cancer; (x) a reduction in mortality; (xi) an increase in survival rate of subjects; (xii) an increase in relapse free survival; (xiii) an increase in the number of pancreatic cancer subjects in remission; (xiv) reduction in hospitalization of a subject; (xv) reduction in hospitalization length; (xvi) a decrease in hospitalization rate; (xvii) an increase in the survival of a subject; (xviii) an increase in symptom-free survival of a pancreatic cancer subject; (xix) an increase in the length of a period of remission of a pancreatic cancer in a subject; (xx) improvement in quality of life (QOL) as assessed by methods well known in the art, e.g., QOL questionnaires and the like; (xxi) a reduction in proliferation from administration of Compound 1 before treatment with another chemotherapeutic agent; (xxii) a reduction in proliferation from administration of Compound 1 after treatment with another chemotherapeutic agent; (xxiii) a reduction in proliferation in a combination therapy from administration of Compound 1 with another chemotherapeutic agent; (xxiv) an additive antiproliferative effect in a combination therapy from administration of Compound 1 with another chemotherapeutic agent; (xxv) a synergistic antiproliferative effect in a combination therapy from administration of Compound 1 with another chemotherapeutic agent; (xxvi) a reduction in proliferation from administration of Compound 1 before therapy with radiation; (xxvii) a reduction in proliferation from administration of Compound 1 after therapy with radiation; (xxviii) a reduction in proliferation from administration of Compound 1 in a combination therapy with radiation; (xxix) a reduction in proliferation from administration of Compound 1 before treatment with surgery; (xxx) a reduction in proliferation from administration of Compound 1 in a combination treatment with surgery; (xxxi) enhancement of or improvement of the therapeutic effect from administration of Compound 1 with a palliative therapy; (xxxii) a decrease in the plasma concentration of BMI-1 in a subject having a pancreatic cancer; (xxxiii) a decrease in circulating proliferative cells in the plasma of a subject having a pancreatic cancer; (xxxiv) an alteration (e.g., a decrease or increase) in the plasma concentration of a pancreatic cancer biomarker in a subject having a pancreatic cancer (e.g., BMI-1, tubulin polymerization, apoptotic markers or tissue and the like); (xxxv) reduction in the concentration of BMI-1 in a biological specimen (e.g., plasma, serum, urine, or any other biofluids) from a subject having a pancreatic cancer; (xxxvi) proliferative cell count is maintained after administration of a therapy as described herein as measured by conventional methods available to one skilled in the art, such as magnetic resonance imaging (MRI), dynamic contrast-enhanced MRI (DCE-MRI), X-ray, computed tomography (CT) scan, positron emission tomography (PET) scan, 7-AAD fluorescence, or DAPI fluorescence; (xxxvii) proliferative cell count is reduced after administration of a therapy as described herein as measured by conventional methods available to one skilled in the art, such as magnetic resonance imaging (MRI), dynamic contrast-enhanced MRI (DCE-MRI), X-ray, computed tomography (CT) scan, positron emission tomography (PET) scan, 7-AAD fluorescence, or DAPI fluorescence; or, (xxxviii) proliferative cell count does not increase or increases by less than expected after administration of a therapy as described herein as measured by conventional methods available to one skilled in the art, such as magnetic resonance imaging (MRI), dynamic contrast-enhanced MRI (DCE-MRI), X-ray, computed tomography (CT) scan, or a positron emission tomography (PET) scan, 7-AAD fluorescence, or DAPI fluorescence.

As used herein, the term "in a 24 hour period" refers to a period of time over which a condition is maintained; for example, the effective amount of Compound 1 is identified when the mean plasma concentration of Compound 1 is achieved and maintained for a plurality of 24 hour periods. In other words, the mean plasma concentration of Compound 1 may be reached in a suitable time, which may be more or less than 24 hours.

As used herein, the term "a therapy as described herein" refers to a method of use for Compound 1 or a pharmaceutically acceptable salt or pharmaceutical composition thereof as an inhibitor of BMI-1 function by targeting inhibition of tubulin polymerization in treating or ameliorating a pancreatic cancer in a subject in need thereof comprising, administering to the subject an effective amount of Compound 1.

In one aspect, the pancreatic cancer is a pancreatic ductal adenocarcinoma. In another aspect of the therapy described herein, the method of use for Compound 1 or a pharmaceutically acceptable salt or pharmaceutical composition thereof comprises a combination with other chemotherapeutic agents having synergistic antiproliferative activity. In one aspect, the other chemotherapeutic agent inhibits BMI-1 functional activity. In another aspect, the other chemotherapeutic agent inhibits tubulin polymerization.

As used herein, the term "pharmaceutically acceptable salt(s)" refers to a salt prepared from a pharmaceutically acceptable non-toxic acid or base including an inorganic acid and base and an organic acid and base; see, for example, *Remington's Pharmaceutical Sciences*, 18th eds., Mack Publishing, Easton Pa. (1990) or *Remington: The Science and Practice of Pharmacy*, 19th eds., Mack Publishing, Easton Pa. (1995).

As used herein, the term "Compound 1" generally refers to a 5-fluoro-2-(6-fluoro-2-methyl-1H-benzo[d]imidazol-1-yl)-N4-[4-(trifluoromethyl)phenyl]pyrimidine-4,6-diamine compound and pharmaceutically acceptable salts thereof. "Compound 1" may be substantially pure (e.g., about 90%, about 95%, about 98%, about 99%, or about 99.9% pure). In various aspects, the term "Compound 1" refers to Compound 109 disclosed in International Publication No. WO2014/081906, which is incorporated in its entirety by reference herein.

Method of Use

As demonstrated herein, Compound 1 or a pharmaceutically acceptable salt or pharmaceutical composition thereof is an inhibitor of tubulin polymerization and BMI-1 function for use in treating or ameliorating a pancreatic cancer in a subject in need thereof comprising, administering to the subject an effective amount of Compound 1 or a pharmaceutically acceptable salt or pharmaceutical composition thereof.

In one aspect, the pancreatic cancer is a pancreatic ductal adenocarcinoma.

In another aspect, the method of use for Compound 1 or a pharmaceutically acceptable salt or pharmaceutical composition thereof comprises, a combination of Compound 1 or a pharmaceutically acceptable salt or pharmaceutical composition thereof with one or more other chemotherapeutic agents, wherein the combination demonstrates synergistic antiproliferative activity. In one aspect, the other chemotherapeutic agent inhibits BMI-1 functional activity. In another aspect, the other chemotherapeutic agent inhibits tubulin polymerization. However, there are no known or approved inhibitors of either or both BMI-1 functional activity or tubulin polymerization for use in treating pancreatic cancers. Accordingly, potent and selective activity, favorable pharmaceutical properties and extensive clinical experience suggest that Compound 1 is a useful agent for treatment of a pancreatic cancer.

In one aspect, methods for inhibiting or reducing tubulin polymerization and BMI-1 function to induce cell-cycle arrest in a proliferating cell or cell line are described herein.

In another aspect, a method for inhibiting or reducing tubulin polymerization and BMI-1 function to induce cell-cycle arrest in a proliferating cell or cell line comprises, contacting Compound 1 or a pharmaceutically acceptable salt or pharmaceutical composition thereof with a proliferating cell or cell line, which proliferating cell or cell line may be naïve or has been shown to be affected by the inhibition or a reduction of tubulin polymerization and BMI-1 function.

In another aspect, non-limiting examples of such cells or cell lines are selected from HL-60, HeLa, HT1080, HCT116, HEK293, NCI H460, U-87MG, ASPC-1, PL-45, HPAF-2, PC-3, MDA-MB-231, MDA-MB-468, A431, SNU-1, AGS, Kato III, A549, Calu-6, A375, SY5Y, SKOV3, Capan-1, sNF96.2, TIVE-L1, TIVE-L2, LNCaP cells and the like. In a more specific aspect, the cell or cell line may be a pancreatic cancer cell.

In one aspect, a method for inhibiting or reducing tubulin polymerization and BMI-1 function in a subject having a pancreatic cancer in need thereof comprises, administering an effective amount of Compound 1 or a pharmaceutically acceptable salt or pharmaceutical composition thereof to the subject as described herein.

In a specific aspect, the subject is diagnosed with a pancreatic cancer capable of being treated by inhibiting or reducing tubulin polymerization and BMI-1 function.

In a specific aspect, a method for inhibiting or reducing tubulin polymerization and BMI-1 function as described herein inhibits or reduces tubulin polymerization and BMI-1 function by about 5%, 10%, 15%, 20%, 25%, 30%, 35%, 40%, 45%, 50%, 55%, 60%, 65%, 80%, 85%, 90%, 95%, or 100% relative to tubulin polymerization and BMI-1 function prior to administration of Compound 1 to the subject, as assessed by methods well known in the art.

In a specific aspect, a method for inhibiting or reducing tubulin polymerization and BMI-1 function as described herein inhibits or reduces tubulin polymerization and BMI-1 function in a range of from about 5% to about 20%, 10% to 30%, 15% to 40%, 15% to 50%, 20% to 30%, 20% to 40%, 20% to 50%, 30% to 60%, 30% to 70%, 30% to 80%, 30% to 90%, 30% to 95%, 30% to 99%, or from about 40% to about 100%, or any range in between, relative to tubulin polymerization and BMI-1 function prior to administration of Compound 1 to the subject, as assessed by methods well known in the art.

In a specific aspect, a method for inhibiting or reducing tubulin polymerization and BMI-1 function as described herein inhibits proliferation or reduces an in vitro or in vivo proliferating cell or cell line population by about 5%, 10%, 15%, 20%, 25%, 30%, 35%, 40%, 45%, 50%, 55%, 60%, 65%, 80%, 85%, 90%, 95%, or 100%, relative to the in vitro or in vivo proliferating cell or cell line population prior to administration of Compound 1 to the subject, as assessed by methods well known in the art.

In a specific aspect, a method for inhibiting or reducing tubulin polymerization and BMI-1 function as described herein inhibits proliferation or reduces an in vitro or in vivo proliferating cell or cell line population in a range of from about 5% to about 20%, 10% to 30%, 15% to 40%, 15% to 50%, 20% to 30%, 20% to 40%, 20% to 50%, 30% to 60%, 30% to 70%, 30% to 80%, 30% to 90%, 30% to 95%, 30% to 99%, or from about 40% to about 100%, or any range in between, relative to the in vitro or in vivo proliferating cell or cell line population prior to administration of Compound 1 to the subject, as assessed by methods well known in the art.

In various aspects, a method for inhibiting or reducing tubulin polymerization and BMI-1 function as described herein reduces the plasma concentration of BMI-1 in a subject as assessed by methods well known in the art, e.g., ELISA.

In one aspect, a method for preventing, treating or ameliorating a pancreatic cancer in a subject in need thereof comprises, administering an amount of Compound 1 effective to inhibit or reduce tubulin polymerization and BMI-1 function in the subject is described herein.

In a specific aspect, a method for preventing, treating or ameliorating a pancreatic cancer in a subject in need thereof as described herein inhibits or reduces tubulin polymerization and BMI-1 function by about 5%, 10%, 15%, 20%, 25%, 30%, 35%, 40%, 45%, 50%, 55%, 60%, 65%, 80%, 85%, 90%, 95%, or 100% relative to tubulin polymerization and BMI-1 function prior to administration of Compound 1 to the subject, as assessed by methods well known in the art.

In a specific aspect, a method for preventing, treating or ameliorating a pancreatic cancer in a subject in need thereof as described herein inhibits or reduces tubulin polymerization and BMI-1 function in a range of from about 5% to about 20%, 10% to 30%, 15% to 40%, 15% to 50%, 20% to 30%, 20% to 40%, 20% to 50%, 30% to 60%, 30% to 70%, 30% to 80%, 30% to 90%, 30% to 95%, 30% to 99%, or from about 40% to about 100%, or any range in between, relative to tubulin polymerization and BMI-1 function prior to administration of Compound 1 to the subject, as assessed by methods well known in the art.

In various aspects, a method for preventing, treating or ameliorating a pancreatic cancer in a subject in need thereof as described herein reduces the concentration of BMI-1 in a subject as assessed by methods well known in the art, e.g., ELISA.

In one aspect, a method for preventing, treating or ameliorating a pancreatic cancer in a subject in need thereof comprises, administering an amount of Compound 1 effective to inhibit proliferation or reduce an in vitro or in vivo proliferating cell or cell line population in the subject is described herein.

In a specific aspect, a method for preventing, treating or ameliorating a pancreatic cancer in a subject in need thereof as described herein inhibits proliferation or reduces an in vitro or in vivo proliferating cell or cell line population in the subject by about 5%, 10%, 15%, 20%, 25%, 30%, 35%, 40%, 45%, 50%, 55%, 60%, 65%, 80%, 85%, 90%, 95%, or 100% relative to proliferation or in vitro or in vivo proliferating cell or cell line population in the subject prior to administration of Compound 1 to the subject, as assessed by methods well known in the art.

In a specific aspect, a method for preventing, treating or ameliorating a pancreatic cancer in a subject in need thereof as described herein inhibits proliferation or reduces an in vitro or in vivo proliferating cell or cell line population in the subject in a range of from about 5% to about 20%, 10% to 30%, 15% to 40%, 15% to 50%, 20% to 30%, 20% to 40%, 20% to 50%, 30% to 60%, 30% to 70%, 30% to 80%, 30% to 90%, 30% to 95%, 30% to 99%, or from about 40% to about 100%, or any range in between, relative to proliferation or in vitro or in vivo proliferating cell or cell line population in the subject prior to administration of Compound 1 to the subject, as assessed by methods well known in the art.

In various aspects, a method for preventing, treating or ameliorating a pancreatic cancer in a subject in need thereof as described herein inhibits proliferation or reduces an in vitro or in vivo proliferating cell or cell line population in a subject as assessed by methods well known in the art, e.g., ELISA.

In one aspect, a method for preventing, treating or ameliorating a pancreatic cancer in a subject in need thereof comprises, administering an amount of Compound 1 effective to inhibit proliferation or reduce an in vitro or in vivo proliferating cell or cell line population in the subject in combination with another therapy (e.g., one or more additional therapies that do not comprise Compound 1, or that comprise a different anti-proliferative agent) to a subject in need thereof is described herein.

Such methods may involve administering Compound 1 prior to, concurrent with, or subsequent to administration of the additional therapy. In certain aspects, such methods have an additive or synergistic effect.

In a specific aspect, presented herein is a method for preventing, treating or ameliorating a pancreatic cancer in a subject in need thereof comprising, administering to a subject in need thereof an effective amount of Compound 1 and an effective amount of another therapy.

Specific examples of cancers that can be prevented, treated or ameliorated in accordance with the methods provided herein include, but are not limited to, pancreatic cancers such as but not limited to, pancreatic ductal adenocarcinoma.

In certain aspects, pancreatic cancers that can be prevented, treated or ameliorated in accordance with the methods provided herein are selected from pancreatic ductal adenocarcinoma.

In one aspect, presented herein is a method for preventing, treating or ameliorating a pancreatic cancer, comprising: (a) administering to a subject in need thereof one or more doses of Compound 1 or a pharmaceutically acceptable salt or pharmaceutical composition thereof a pharmaceutical composition thereof; and (b) monitoring the concentration of certain biomarkers, before and/or after step (a).

In a specific aspect, the monitoring step (b) is carried out before and/or after a certain number of doses (e.g., 1, 2, 4, 6, 8, 10, 12, 14, 15, or 29 doses, or more doses; 2 to 4, 2 to 8, 2 to 20 or 2 to 30 doses) or a certain time period (e.g., 1, 2, 3, 4, 5, 6, or 7 days; or 1, 2, 3, 4, 5, 10, 15, 20, 30, 40, 45, 48, or 50 weeks) of administering Compound 1 or a pharmaceutically acceptable salt or pharmaceutical composition thereof.

In a specific aspect, one or more of these monitoring parameters are detected prior to administration of Compound 1 or a pharmaceutically acceptable salt or pharmaceutical composition thereof to the subject.

In a specific aspect, a decrease in the proliferation of an in vitro or in vivo proliferating cell or cell line population following administration of Compound 1 or a pharmaceutically acceptable salt or pharmaceutical composition thereof indicates that the course of treatment is effective for preventing, treating or ameliorating the pancreatic cancer.

In a specific aspect, a change in the proliferation of an in vitro or in vivo proliferating cell or cell line population following administration of Compound 1 or a pharmaceutically acceptable salt or pharmaceutical composition thereof may indicate that the dosage, frequency and/or length of administration of Compound 1 or a pharmaceutically acceptable salt or pharmaceutical composition thereof may be adjusted (e.g., increased, reduced or maintained).

In a specific aspect, the concentration of certain biomarkers in biological specimens of a subject is monitored before, during and/or after a course of treatment for a pancreatic cancer involving the administration of Compound 1 or a pharmaceutically acceptable salt or pharmaceutical composition thereof to the subject.

The dosage, frequency and/or length of administration of Compound 1 or a pharmaceutically acceptable salt or pharmaceutical composition thereof to a subject might be modified as a result of the proliferation of an in vitro or in vivo proliferating cell or cell line population. Alternatively, the changes in these monitoring parameters (e.g., concentration of certain biomarkers) might indicate that the course of treatment involving the administration of the Compound 1 or a pharmaceutically acceptable salt or pharmaceutical composition thereof is effective in preventing, treating or ameliorating the pancreatic cancer.

The concentration of certain biomarkers in a subject may be detected by any technique known to one of skill in the art. In certain aspects, the method for detecting the concentration of certain biomarkers of a subject comprises obtaining a biological sample (e.g., tissue or fluid sample) from the subject and detecting the concentration of the biomarkers in the biological sample (e.g., from plasma, serum, urine, or any other biofluids), that has been subjected to certain types of treatment (e.g., centrifugation), and detection by use of immunological techniques, such as ELISA.

In a specific aspect, an ELISA assay, as described herein, may be used to detect the concentration of the biomarkers in a biological sample (e.g., from plasma, serum, urine, or any other biofluids) that has been subjected to certain types of treatment (e.g., centrifugation). Other techniques known in the art that may be used to detect the concentration of the biomarkers in a biological sample include multiplex or proteomic assays.

In specific aspects, the methods for preventing, treating or ameliorating a pancreatic cancer provided herein alleviate or manage one, two or more symptoms associated with the pancreatic cancer. Alleviating or managing one, two or more symptoms of the pancreatic cancer may be used as a clinical endpoint for efficacy of Compound 1 or a pharmaceutically acceptable salt or pharmaceutical composition thereof for preventing, treating or ameliorating the pancreatic cancer. In some aspects, the methods for preventing, treating or ameliorating the pancreatic cancer provided herein reduce the duration and/or severity of one or more symptoms associated with the pancreatic cancer. In some aspects, the methods for preventing, treating or ameliorating the pancreatic cancer provided herein inhibit the onset, progression and/or recurrence of one or more symptoms associated with the pancreatic cancer. In some aspects, the methods for treating the pancreatic cancer provided herein reduce the number of symptoms associated with the pancreatic cancer.

In certain aspects, the methods for preventing, treating or ameliorating a pancreatic cancer provided herein prolong or delay the G1/S or late G1/S phase of the cell cycle (i.e., the period between the late checkpoint (resting or pre-DNA synthesis phase), and the early DNA synthesis phase). In other aspects, the methods for preventing, treating or ameliorating a pancreatic cancer provided herein prolong or delay the S or G2/M phase of the cell cycle (i.e., the period between DNA synthesis and the early division phase).

In some aspects, the methods for preventing, treating or ameliorating a pancreatic cancer provided herein reduce, ameliorate, or alleviate the severity of the pancreatic cancer and/or one or more symptoms thereof. In other aspects, the methods for preventing, treating or ameliorating a pancreatic cancer provided herein reduce hospitalization (e.g., the frequency or duration of hospitalization) of a subject diagnosed with the pancreatic cancer.

In certain aspects, the methods provided herein increase the survival of a subject diagnosed with a pancreatic cancer. In specific aspects, the methods provided herein increase the survival of a subject diagnosed with a pancreatic cancer by about 6 months or more, about 7 months or more, about 8 months or more, about 9 months or more, or about 12 months or more.

In particular aspects, the methods for preventing, treating or ameliorating a pancreatic cancer provided herein inhibit or reduce the progression of the pancreatic cancer, or one or more symptoms associated therewith. In specific aspects, the methods for preventing, treating or ameliorating a pancreatic cancer provided herein enhance or improve the therapeutic effect of another therapy (e.g., an anti-cancer agent, radiation, drug therapy, such as chemotherapy, anti-androgen therapy, or surgery). In certain aspects, the methods for preventing, treating or ameliorating a pancreatic cancer provided herein involve the use of Compound 1 or a pharmaceutically acceptable salt or pharmaceutical composition thereof as an adjuvant therapy.

In particular aspects, the methods for preventing, treating or ameliorating a pancreatic cancer provided herein reduce the mortality of subjects diagnosed with the pancreatic cancer. In certain aspects, the methods for preventing, treating or ameliorating a pancreatic cancer provided herein increase the number of subjects in remission or decrease the hospitalization rate. In other aspects, the methods for preventing, treating or ameliorating a pancreatic cancer provided herein prevent the development, onset or progression of one or more symptoms associated with the pancreatic cancer.

In particular aspects, the methods for preventing, treating or ameliorating a pancreatic cancer provided herein increase symptom-free survival of pancreatic cancer subjects. In some aspects, the methods for preventing, treating or ameliorating a pancreatic cancer provided herein do not cure the pancreatic cancer in subjects, but prevent the progression or worsening of the disease. In some aspects, the methods for preventing, treating or ameliorating a pancreatic cancer provided herein improve the subject's quality of life.

In certain aspects, the methods for preventing, treating or ameliorating a pancreatic cancer provided herein increase the cancer-free survival rate of subjects diagnosed with the cancer. In some aspects, the methods for preventing, treating or ameliorating a pancreatic cancer provided herein increase relapse-free survival. In certain aspects, the methods for preventing, treating or ameliorating a pancreatic cancer provided herein increase the number of subjects in remission. In other aspects, the methods for preventing, treating or ameliorating a pancreatic cancer provided herein increase the length of remission in subjects.

Treatment Population

In some aspects, a subject treated for a pancreatic cancer in accordance with the methods provided herein is a human who has or is diagnosed with a pancreatic cancer. In other aspects, a subject treated for a pancreatic cancer in accordance with the methods provided herein is a human predisposed or susceptible to a pancreatic cancer. In some aspects, a subject treated for a pancreatic cancer in accordance with the methods provided herein is a human at risk of developing a pancreatic cancer.

In one aspect, a subject treated for a pancreatic cancer in accordance with the methods provided herein is a human infant. In another aspect, a subject treated for a pancreatic cancer in accordance with the methods provided herein is a human toddler. In another aspect, a subject treated for a pancreatic cancer in accordance with the methods provided herein is a human child. In another aspect, a subject treated for a pancreatic cancer in accordance with the methods provided herein is a human adult. In another aspect, a subject treated for a pancreatic cancer in accordance with the methods provided herein is a middle-aged human. In another aspect, a subject treated for a pancreatic cancer in accordance with the methods provided herein is an elderly human.

In certain aspects, a subject treated for cancer in accordance with the methods provided herein has a pancreatic cancer metastasized to other areas of the body, such as the bones, lung and liver. In certain aspects, a subject treated for pancreatic cancer in accordance with the methods provided herein is in remission from the pancreatic cancer. In some aspects, the subject treated for pancreatic cancer in accordance with the methods provided herein had a recurrence of the pancreatic cancer. In certain aspects, a subject treated in accordance with the methods provided herein is experiencing recurrence of one or more symptoms associated with the pancreatic cancer.

In certain aspects, a subject treated for a pancreatic cancer in accordance with the methods provided herein is a human that is about 1 to about 5 years old, about 5 to 10 years old, about 10 to about 18 years old, about 18 to about 30 years old, about 25 to about 35 years old, about 35 to about 45 years old, about 40 to about 55 years old, about 50 to about 65 years old, about 60 to about 75 years old, about 70 to about 85 years old, about 80 to about 90 years old, about 90 to about 95 years old or about 95 to about 100 years old, or any age in between.

In a specific aspect, a subject treated for a pancreatic cancer in accordance with the methods provided herein is a human that is 18 years old or older. In a particular aspect, a subject treated for a pancreatic cancer in accordance with the methods provided herein is a human child that is between the age of 1 year old to 18 years old. In a certain aspect, a subject treated for a pancreatic cancer in accordance with the methods provided herein is a human that is between the age of 12 years old and 18 years old. In a certain aspect, the subject is a male human. In another aspect, the subject is a female human. In one aspect, the subject is a female human that is not pregnant or is not breastfeeding. In one aspect, the subject is a female that is pregnant or will/might become pregnant, or is breast feeding.

In particular aspects, a subject treated for a pancreatic cancer in accordance with the methods provided herein is a human that is in an immunocompromised state or immunosuppressed state. In certain aspects, a subject treated for a pancreatic cancer in accordance with the methods provided herein is a human receiving or recovering from immunosuppressive therapy. In certain aspects, a subject treated for a pancreatic cancer in accordance with the methods provided herein is a human that has or is at risk of getting a pancreatic cancer. In certain aspects, a subject treated for a pancreatic cancer in accordance with the methods provided herein is a human who is, will or has undergone surgery, drug therapy, such as chemotherapy, hormonal therapy and/or radiation therapy.

In some aspects, a subject treated for a pancreatic cancer in accordance with the methods provided herein is administered Compound 1 or a pharmaceutically acceptable salt or pharmaceutical composition thereof, or a combination therapy before any adverse effects or intolerance to therapies other than Compound 1 develops. In some aspects, a subject treated for a pancreatic cancer in accordance with the methods provided herein is a refractory subject. In certain aspects, a refractory subject is a subject refractory to a standard therapy (e.g., surgery, radiation and/or drug therapy such as chemotherapy). In certain aspects, a subject with a pancreatic cancer is refractory to a therapy when the pancreatic cancer has not significantly been eradicated and/or the one or more symptoms have not been significantly alleviated. The determination of whether a subject refractory can be made either in vivo or in vitro by any method known in the art for assaying the effectiveness of a treatment of a pancreatic cancer, using art-accepted meanings of "refractory" in such a context.

In some aspects, a subject treated for a pancreatic cancer in accordance with the methods provided herein is a human that has proven refractory to therapies other than treatment with Compound 1 or a pharmaceutically acceptable salt or pharmaceutical composition thereof, but is no longer on these therapies. In certain aspects, a subject treated for a pancreatic cancer in accordance with the methods provided herein is a human already receiving one or more conventional anti-cancer therapies, such as surgery, drug therapy such as chemotherapy, anti-androgen therapy or radiation. Among these subjects are refractory subjects, subjects who are too young for conventional therapies, and subjects with recurring pancreatic cancers despite treatment with existing therapies.

In some aspects, a subject treated for a pancreatic cancer in accordance with the methods provided herein is a human susceptible to adverse reactions to conventional therapies. In some aspects, a subject treated for a pancreatic cancer in accordance with the methods provided herein is a human that has not received a therapy, e.g., drug therapy such as chemotherapy, surgery, anti-androgen therapy or radiation therapy, prior to the administration of Compound 1 or a pharmaceutically acceptable salt or pharmaceutical composition thereof. In other aspects, a subject treated for a pancreatic cancer in accordance with the methods provided herein is a human that has received a therapy prior to administration of Compound 1 or a pharmaceutically acceptable salt or pharmaceutical composition thereof. In some aspects, a subject treated for a pancreatic cancer in accordance with the methods provided herein is a human that has experienced adverse side effects to the prior therapy or the prior therapy was discontinued due to unacceptable levels of toxicity to the human.

Dosage and Administration

In accordance with the methods for preventing, treating or ameliorating a pancreatic cancer provided herein, Compound 1 or a pharmaceutically acceptable salt or pharmaceutical composition thereof can be administered to a subject in need thereof by a variety of routes in amounts which result in a beneficial or therapeutic effect. Compound 1 or a pharmaceutically acceptable salt or pharmaceutical composition thereof may be orally administered to a subject in need thereof in accordance with the methods for preventing, treating or ameliorating a pancreatic cancer provided herein. The oral administration of Compound 1 or a pharmaceutically acceptable salt or pharmaceutical composition thereof may facilitate subjects in need of such treatment complying with a regimen for taking Compound 1 or a pharmaceutically acceptable salt or pharmaceutical composition thereof. Thus, in a specific aspect, Compound 1 or a pharmaceutically acceptable salt or pharmaceutical composition thereof is administered orally to a subject in need thereof. In another aspect, Compound 1 or a pharmaceutically acceptable salt or pharmaceutical composition thereof provided herein can be administered orally, with or without food or water.

Other routes of administration include, but are not limited to, intravenous, intradermal, intrathecal, intramuscular, subcutaneous, intranasal, inhalation, transdermal, topical, transmucosal, intracranial, epidural and intra-synovial. In one aspect, Compound 1 or a pharmaceutically acceptable salt or pharmaceutical composition thereof is administered systemically (e.g., parenterally) to a subject in need thereof. In one aspect, Compound 1 or a pharmaceutically acceptable salt or pharmaceutical composition thereof is administered via a route that permits Compound 1 or a pharmaceutically acceptable salt or pharmaceutical composition thereof to cross the blood-brain barrier (e.g., orally).

In accordance with the methods for preventing, treating or ameliorating a pancreatic cancer provided herein that involve administration of Compound 1 or a pharmaceutically acceptable salt or pharmaceutical composition thereof in combination with one or more additional therapies, Compound 1 or a pharmaceutically acceptable salt or pharmaceutical composition thereof and one or more additional therapies may be administered by the same route or a different route of administration.

The dosage and frequency of administration of Compound 1 or a pharmaceutically acceptable salt or pharmaceutical composition thereof to a subject in need thereof in accordance with the methods for preventing, treating or ameliorating a pancreatic cancer provided herein will be efficacious while minimizing any side effects. The exact dosage and frequency of administration of Compound 1 or a pharmaceutically acceptable salt or pharmaceutical composition thereof can be determined by a practitioner, in light of factors related to the subject that requires treatment.

Factors which may be taken into account include the severity of the disease state, general health of the subject, age, weight, and gender of the subject, diet, time and frequency of administration, drug combination(s), reaction sensitivities, and tolerance/response to therapy. The dosage and frequency of administration of Compound 1 or a pharmaceutically acceptable salt or pharmaceutical composition thereof may be adjusted over time to provide an effective amount of Compound 1 or a pharmaceutically acceptable salt or pharmaceutical composition thereof or to maintain the desired effect.

As described herein, the methods for preventing, treating or ameliorating a pancreatic cancer in a subject in need thereof presented herein comprises, administering to the subject an effective amount of Compound 1 or a pharmaceutically acceptable salt or pharmaceutical composition thereof, wherein the effective amount is a dose administered to the subject twice per week on different days, wherein the second dose in a week follows the first by three days, and wherein the first dose in a following week follows the second dose in a preceding week by four days.

In a specific aspect, the effective amount is a dose administered to the subject that may be increased or decreased depending on subject response.

In a specific aspect, a method for preventing, treating or ameliorating a pancreatic cancer in a subject in need thereof comprises the administration of an effective amount of Compound 1 or a pharmaceutically acceptable salt or pharmaceutical composition thereof to the subject, wherein the effective amount is a dose selected from a dose in a range of from about 50 mg to about 200 mg, from about 100 mg to about 200 mg, from about 150 mg to about 200 mg, and the like, or any range in between, administered orally twice per week.

In a specific aspect, a method for preventing, treating or ameliorating a pancreatic cancer in a subject in need thereof comprises the administration of an effective amount of Compound 1 or a pharmaceutically acceptable salt or pharmaceutical composition thereof to the subject, wherein the effective amount is a dose selected from about 50 mg, about 100 mg, about 150 mg or about 200 mg, and the like, or any range in between, administered orally twice per week.

In a specific aspect, a method for preventing, treating or ameliorating a pancreatic cancer in a subject in need thereof comprises the administration of an effective amount of Compound 1 or a pharmaceutically acceptable salt or pharmaceutical composition thereof to the subject, wherein the effective amount is a dose of about 50 mg administered orally twice per week.

In some aspects, a method for preventing, treating or ameliorating a pancreatic cancer in a subject in need thereof comprises the administration of an effective amount of Compound 1 or a pharmaceutical composition thereof to the subject, wherein the effective amount is a dosage that is expressed as mg per meter squared ($mg/m^2$). The $mg/m^2$ for Compound 1 may be determined, for example, by multiplying a conversion factor for an animal by an animal dose in mg per kilogram (mg/kg) to obtain the dose in $mg/m^2$ for human dose equivalent. For regulatory purposes, the following conversion factors may be used: Mouse=3, Hamster=4.1, Rat=6, Guinea Pig=7.7. (based on Freireich et al., Cancer Chemother. Rep. 50(4):219-244 (1966)). The height and weight of a human may be used to calculate a human body surface area applying Boyd's Formula of Body Surface Area. In specific aspects, a method for preventing, treating or ameliorating a pancreatic cancer in a subject in need thereof comprises the administration of an effective amount of Compound 1 or a pharmaceutical composition thereof to the subject, wherein the effective amount is an amount in the range of from about 0.1 $mg/m^2$ to about 1000 $mg/m^2$, or any range in between.

In one aspect, a method for preventing, treating or ameliorating a pancreatic cancer in a subject in need thereof comprises the administration of an effective amount of Compound 1 or a pharmaceutical composition thereof to the subject, wherein the effective amount is a dosage that achieves a target mean plasma concentration of Compound 1 in a subject with a pancreatic cancer or an animal model with a pre-established pancreatic cancer.

In a specific aspect, a method for preventing, treating or ameliorating a pancreatic cancer in a subject in need thereof comprises the administration of an effective amount of Compound 1 or a pharmaceutical composition thereof to the subject, wherein the effective amount is a dosage that achieves a mean plasma concentration of Compound 1 in a 24 hour period in a range of from approximately 3 hr-µg/mL to approximately 70 hr-µg/mL, from approximately 3 hr-µg/mL to approximately 60 hr-µg/mL, from approximately 3 hr-µg/mL to approximately 50 hr-µg/mL, from approximately 3 hr-µg/mL to approximately 40 hr-µg/mL, from approximately 3 hr-µg/mL to approximately 30 hr-µg/mL, from approximately 3 hr-µg/mL to approximately 20 hr-µg/mL, from approximately 3 hr-µg/mL to approximately 10 hr-µg/mL, and the like, or any range in between, in a subject with the pancreatic cancer or an animal model with a pre-established pancreatic cancer.

In a specific aspect, a method for preventing, treating or ameliorating a pancreatic cancer in a subject in need thereof comprises the administration of an effective amount of Compound 1 or a pharmaceutical composition thereof to the subject, wherein the effective amount is a dosage that achieves a mean plasma concentration of Compound 1 in a 24 hour period of approximately 3 hr-µg/mL, approximately 10 hr-µg/mL, approximately 20 hr-µg/mL, approximately 30 hr-µg/mL, approximately 40 hr-µg/mL, approximately 50 hr-µg/mL, approximately 60 hr-µg/mL, approximately 70 hr-µg/mL, and the like, or any range in between, in a subject with the pancreatic cancer or an animal model with a pre-established pancreatic cancer.

To achieve such plasma concentrations, a dose described herein of Compound 1 or a pharmaceutical composition thereof may be administered. In certain aspects, subsequent doses of Compound 1 or a pharmaceutical composition thereof may be adjusted accordingly based on the mean plasma concentrations of Compound 1 achieved with a dose of Compound 1 or a pharmaceutical composition thereof administered to the subject.

In specific aspects, a method for preventing, treating or ameliorating a pancreatic cancer in a subject in need thereof comprises the administration of an effective amount of Compound 1 or a pharmaceutical composition thereof to the subject, wherein the effective amount is a dosage that achieves a reduced target mean plasma concentration of one or more biomarkers in a subject with the pancreatic cancer or an animal model with a pre-established pancreatic cancer.

In particular aspects, a method for preventing, treating or ameliorating a pancreatic cancer in a subject in need thereof comprises the administration of an effective amount of Compound 1 or a pharmaceutical composition thereof to the subject, wherein the effective amount is a dosage that achieves the desired tissue to mean plasma concentration ratios of Compound 1 or a pharmaceutical composition thereof as determined, e.g., by any imaging techniques known in the art, in a subject with the pancreatic cancer or an animal model with a pre-established pancreatic cancer.

In some aspects, a method for preventing, treating or ameliorating a pancreatic cancer in a subject in need thereof comprises the administration of an effective amount of Compound 1 or a pharmaceutical composition thereof to the subject, wherein the effective amount may or may not be the same for each dose. In particular aspects, a first (i.e., initial) dose of Compound 1 or a pharmaceutical composition thereof is administered to a subject in need thereof for a first period of time, followed by a second (i.e., loading) dose of Compound 1 or a pharmaceutical composition thereof is administered to the subject for a second period of time and, subsequently, a third (i.e., maintenance) dose of Compound 1 or a pharmaceutical composition thereof is administered to the subject for a third period of time. The first dose may be more than the second dose, or the first dose may be less than the second dose. In similar fashion, the third dose of Compound 1 or a pharmaceutical composition thereof may be more or less than the second dose and more or less than the first dose.

In some aspects, the dosage amounts described herein refer to total amounts administered; that is, if more than one Compound is administered, then, in some aspects, the dosages correspond to the total amount administered. In a specific aspect, oral compositions contain about 5% to about 95% of Compound 1 by weight.

The length of time that a subject in need thereof is administered Compound 1 or a pharmaceutical composition thereof in accordance with a method for preventing, treating or ameliorating a pancreatic cancer in a subject in need thereof will be the time period that is determined by cancer free survival or freedom from symptoms. In certain aspects, a method for treating a pancreatic cancer presented herein comprises the administration of Compound 1 or a pharmaceutical composition thereof for a period of time until the severity and/or number of one or more symptoms associated with the pancreatic cancer decreases.

In some aspects, a method for preventing, treating or ameliorating a pancreatic cancer in a subject in need thereof comprises the administration of Compound 1 or a pharmaceutical composition thereof for up to 48 weeks. In other aspects, a method for preventing, treating or ameliorating a pancreatic cancer in a subject in need thereof comprises the administration of Compound 1 or a pharmaceutical composition thereof for up to 4 weeks, 8 weeks, 12 weeks, 16 weeks, 20 weeks, 24 weeks, 26 weeks (0.5 year), 52 weeks (1 year), 78 weeks (1.5 years), 104 weeks (2 years), or 130 weeks (2.5 years) or more.

In certain aspects, a method for preventing, treating or ameliorating a pancreatic cancer in a subject in need thereof comprises the administration of Compound 1 or a pharmaceutical composition thereof for an indefinite period of time. In some aspects, a method for treating a pancreatic cancer presented herein comprises the administration of Compound 1 or a pharmaceutical composition thereof for a period of time followed by a period of rest (i.e., a period wherein Compound 1 or a pharmaceutical composition thereof is not administered) before the administration of Compound 1 or a pharmaceutical composition thereof is resumed.

In specific aspects, a method for preventing, treating or ameliorating a pancreatic cancer in a subject in need thereof comprises the administration of Compound 1 or a pharmaceutical composition thereof in cycles, e.g., 1 week cycles, 2 week cycles, 3 week cycles, 4 week cycles, 5 week cycles, 6 week cycles, 8 week cycles, 9 week cycles, 10 week cycles, 11 week cycles, or 12 week cycles. In such cycles, Compound 1 or a pharmaceutical composition thereof may be administered once or twice per week. In a specific aspect of a weekly cycle, Compound 1 or a pharmaceutical composition thereof may be administered twice per week. In a specific aspect of such a weekly cycle, Compound 1 or a pharmaceutical composition thereof may be administered once per day.

In specific aspects, the period of time of administration of Compound 1 or a pharmaceutical composition thereof may be dictated by one or more monitoring parameters, e.g., concentration of certain biomarkers.

In particular aspects, the period of time of administration of Compound 1 or a pharmaceutical composition thereof may be adjusted based on one or more monitoring parameters, e.g., concentration of biomarkers.

In certain aspects, in accordance with a method for preventing, treating or ameliorating a pancreatic cancer in a subject in need thereof, Compound 1 or a pharmaceutical composition thereof is administered to a subject in need thereof prior to, concurrently with, or after a meal (e.g., breakfast, lunch, or dinner). In specific aspects, in accordance with the methods for treating a pancreatic cancer presented herein, Compound 1 or a pharmaceutical composition thereof is administered to a subject in need thereof in the morning (e.g., between 5 am and 12 pm).

In certain aspects, in accordance with a method for preventing, treating or ameliorating a pancreatic cancer in a subject in need thereof, Compound 1 or a pharmaceutical composition thereof is administered to a subject in need thereof at noon (i.e., 12 pm). In particular aspects, in accordance with the methods for treating a pancreatic cancer presented herein, Compound 1 or a pharmaceutical composition thereof is administered to a subject in need thereof in the afternoon (e.g., between 12 pm and 5 pm), evening (e.g., between 5 pm and bedtime), and/or before bedtime.

In a specific aspect, a dose of Compound 1 or a pharmaceutical composition thereof is administered to a subject once per day and twice per week.

Combination Therapies

Presented herein are combination therapies for the treatment of a pancreatic cancer which involve the administration of Compound 1 or a pharmaceutical composition thereof in combination with one or more additional therapies to a subject in need thereof. In a specific aspect, presented herein are combination therapies for the treatment of a pancreatic cancer which involve the administration of an effective amount of Compound 1 or a pharmaceutical composition thereof in combination with an effective amount of another therapy to a subject in need thereof.

As used herein, the term "in combination," refers, in the context of the administration of Compound 1 or a pharmaceutical composition thereof, to the administration of Compound 1 or a pharmaceutical composition thereof prior to, concurrently with, or subsequent to the administration of one or more additional therapies (e.g., agents, surgery, or radiation) for use in treating a pancreatic cancer. The use of the term "in combination" does not restrict the order in which one or more therapeutic agents and one or more additional therapies are administered to a subject. In specific aspects, the interval of time between the administration of Compound 1 or a pharmaceutical composition thereof and the administration of one or more additional therapies may be about 1-5 minutes, 1-30 minutes, 30 minutes to 60 minutes, 1 hour, 1-2 hours, 2-6 hours, 2-12 hours, 12-24 hours, 1-2 days, 2 days, 3 days, 4 days, 5 days, 6 days, 7 days, 1 week, 2 weeks, 3 weeks, 4 weeks, 5 weeks, 6 weeks, 7 weeks, 8 weeks, 9 weeks, 10 weeks, 15 weeks, 20 weeks, 26 weeks, 52 weeks, 11-15 weeks, 15-20 weeks, 20-30 weeks, 30-40 weeks, 40-50 weeks, 1 month, 2 months, 3 months, 4 months 5 months, 6 months, 7 months, 8 months, 9 months, 10 months, 11 months, 12 months, 1 year, 2 years, or any period of time in between. In certain aspects, Compound 1 or a pharmaceutical composition thereof and one or more additional therapies are administered less than 1 day, 1 week, 2 weeks, 3 weeks, 4 weeks, one month, 2 months, 3 months, 6 months, 1 year, 2 years, or 5 years apart.

In some aspects, the combination therapies provided herein involve administering Compound 1 or a pharmaceutical composition thereof daily, and administering one or more additional therapies once a week, once every 2 weeks, once every 3 weeks, once every 4 weeks, once every month, once every 2 months (e.g., approximately 8 weeks), once every 3 months (e.g., approximately 12 weeks), or once every 4 months (e.g., approximately 16 weeks). In certain aspects, Compound 1 or a pharmaceutical composition thereof and one or more additional therapies are cyclically administered to a subject. Cycling therapy comprises the administration of Compound 1 or a pharmaceutical composition thereof for a period of time, followed by the administration of one or more additional therapies for a period of time, and repeating this sequential administration. In certain aspects, cycling therapy may also include a period of rest where Compound 1 or a pharmaceutical composition thereof or the additional therapy is not administered for a period of time (e.g., 2 days, 3 days, 4 days, 5 days, 6 days, 7 days, 1 week, 2 weeks, 3 weeks, 4 weeks, 5 weeks, 10 weeks, 20 weeks, 1 month, 2 months, 3 months, 4 months, 5 months, 6 months, 7 months, 8 months, 9 months, 10 months, 11 months, 12 months, 2 years, or 3 years). In an aspect, the number of cycles administered is from 1 to 12 cycles, from 2 to 10 cycles, or from 2 to 8 cycles.

In some aspects, a method for preventing, treating or ameliorating a pancreatic cancer in a subject in need thereof comprises administering Compound 1 or a pharmaceutical composition thereof as a single agent for a period of time prior to administering Compound 1 or a pharmaceutical composition thereof in combination with an additional therapy. In certain aspects, the methods for treating a pancreatic cancer provided herein comprise administering an additional therapy alone for a period of time prior to administering Compound 1 or a pharmaceutical composition thereof in combination with the additional therapy.

In some aspects, the administration of Compound 1 or a pharmaceutical composition thereof and one or more additional therapies in accordance with the methods presented herein have an additive effect relative the administration of Compound 1 or a pharmaceutical composition thereof or said one or more additional therapies alone. In some aspects, the administration of Compound 1 or a pharmaceutical composition thereof and one or more additional therapies in accordance with the methods presented herein have a synergistic effect relative to the administration of Compound 1 or a pharmaceutical composition thereof or said one or more additional therapies alone.

As used herein, the term "synergistic," refers to the effect of the administration of Compound 1 or a pharmaceutical composition thereof in combination with one or more additional therapies (e.g., agents), which combination is more effective than the additive effects of any two or more single therapies (e.g., agents).

In a specific aspect, a synergistic effect of a combination therapy permits the use of lower dosages (i.e., sub-optimal doses) of Compound 1 or a pharmaceutical composition thereof or an additional therapy and/or less frequent administration of Compound 1 or a pharmaceutical composition thereof or an additional therapy to a subject.

In certain aspects, the ability to utilize lower dosages of Compound 1 or a pharmaceutical composition thereof or of an additional therapy and/or to administer Compound 1 or a pharmaceutical composition thereof or said additional therapy less frequently reduces the toxicity associated with the administration of Compound 1 or a pharmaceutical composition thereof or of said additional therapy, respectively, to a subject without reducing the efficacy of Compound 1 or a pharmaceutical composition thereof or of said additional therapy, respectively, in the treatment of a pancreatic cancer.

In some aspects, a synergistic effect results in improved efficacy of Compound 1 or a pharmaceutical composition thereof and each of said additional therapies in treating a pancreatic cancer. In some aspects, a synergistic effect of a combination of Compound 1 or a pharmaceutical composition thereof and one or more additional therapies avoids or reduces adverse or unwanted side effects associated with the use of any single therapy.

The combination of Compound 1 or a pharmaceutical composition thereof and one or more additional therapies can be administered to a subject in the same pharmaceutical composition. Alternatively, Compound 1 or a pharmaceutical composition thereof and one or more additional therapies can be administered concurrently to a subject in separate pharmaceutical compositions. Compound 1 or a pharmaceutical composition thereof and one or more additional therapies can be administered sequentially to a subject in separate pharmaceutical compositions. Compound 1 or a pharmaceutical composition thereof and one or more additional therapies may also be administered to a subject by the same or different routes of administration.

The combination therapies provided herein involve administering to a subject to in need thereof Compound 1 or a pharmaceutical composition thereof in combination with conventional, or known, therapies for treating a pancreatic cancer. Other therapies for a pancreatic cancer or a condition associated therewith are aimed at controlling or relieving one or more symptoms. Accordingly, in some aspects, the combination therapies provided herein involve administering to a subject to in need thereof a pain reliever, or other therapies aimed at alleviating or controlling one or more symptoms associated with a pancreatic cancer or a condition associated therewith.

Specific examples of anti-cancer agents that may be used in combination with Compound 1 or a pharmaceutical composition thereof for treating a pancreatic cancer include: a hormonal agent (e.g., aromatase inhibitor, selective estrogen receptor modulator (SERM), and estrogen receptor antagonist), chemotherapeutic agent (e.g., microtubule dissembly blocker, antimetabolite, topisomerase inhibitor, and DNA crosslinker or damaging agent), anti-angiogenic agent (e.g., VEGF antagonist, receptor antagonist, integrin antagonist, vascular targeting agent (VTA)/vascular disrupting agent (VDA)), radiation therapy, and conventional surgery.

Non-limiting examples of hormonal agents that may be used in combination with Compound 1 or a pharmaceutical composition thereof for treating a pancreatic cancer include aromatase inhibitors, SERMs, and estrogen receptor antagonists. Hormonal agents that are aromatase inhibitors may be steroidal or nonsteroidal. Non-limiting examples of nonsteroidal hormonal agents include letrozole, anastrozole, aminoglutethimide, fadrozole, and vorozole. Non-limiting examples of steroidal hormonal agents include aromasin (exemestane), formestane, and testolactone. Non-limiting examples of hormonal agents that are SERMs include tamoxifen (branded/marketed as Nolvadex®), afimoxifene, arzoxifene, bazedoxifene, clomifene, femarelle, lasofoxifene, ormeloxifene, raloxifene, and toremifene. Non-limiting examples of hormonal agents that are estrogen receptor antagonists include fulvestrant. Other hormonal agents include but are not limited to abiraterone and Ionaprisan.

Non-limiting examples of chemotherapeutic agents that may be used in combination with Compound 1 or a pharmaceutical composition thereof for treating cancer include microtubule disassembly blocker, antimetabolite, topoisomerase inhibitor, and DNA crosslinker or damaging agent.

Chemotherapeutic agents that are microtubule disassembly blockers include, but are not limited to, taxenes (e.g., paclitaxel (branded/marketed as TAXOL®), docetaxel, nab-paclitaxel (nanoparticle albumin-bound paclitaxel, branded/marketed as ABRAXANE®), larotaxel, ortataxel, and tesetaxel); epothilones (e.g., ixabepilone); and vincalkaloids (e.g., vinorelbine, vinblastine, vindesine, and vincristine (branded/marketed as ONCOVIN®)).

Chemotherapeutic agents that are antimetabolites include, but are not limited to, folate antimetabolites (e.g., methotrexate, aminopterin, pemetrexed, raltitrexed); purine antimetabolites (e.g., cladribine, clofarabine, fludarabine, mercaptopurine, pentostatin, thioguanine); pyrimidine antimetabolites (e.g., 5-fluorouracil, capcitabine, gemcitabine (GEMZAR), cytarabine, decitabine, floxuridine, tegafur); and deoxyribonucleotide antimetabolites (e.g., hydroxyurea).

Chemotherapeutic agents that are topoisomerase inhibitors include, but are not limited to, class I (camptotheca) topoisomerase inhibitors (e.g., topotecan (branded/marketed as HYCAMTIN®) irinotecan, rubitecan, and belotecan); class II (podophyllum) topoisomerase inhibitors (e.g., etoposide or VP-16, and teniposide); anthracyclines (e.g., doxorubicin, epirubicin, Doxil, aclarubicin, amrubicin, daunorubicin, idarubicin, pirarubicin, valrubicin, and zorubicin); and anthracenediones (e.g., mitoxantrone, and pixantrone).

Chemotherapeutic agents that are DNA crosslinkers (or DNA damaging agents) include, but are not limited to, alkylating agents (e.g., cyclophosphamide, mechlorethamine, ifosfamide (branded/marketed as IFEX®), trofosfamide, chlorambucil, melphalan, prednimustine, bendamustine, uramustine, estramustine, carmustine (branded/marketed as BiCNU®), lomustine, semustine, fotemustine, nimustine, ranimustine, streptozocin, busulfan, mannosulfan, treosulfan, carboquone, N,N'N'-triethylenethiophosphoramide, triaziquone, triethylenemelamine); alkylating-like agents (e.g., carboplatin (branded/marketed as PARAPLATIN®), cisplatin, oxaliplatin, nedaplatin, triplatin tetranitrate, satraplatin, picoplatin); nonclassical DNA crosslinkers (e.g., procarbazine, dacarbazine, temozolomide (branded/marketed as TEMODAR®), altretamine, mitobronitol); and intercalating agents (e.g., actinomycin, bleomycin, mitomycin, and plicamycin).

Non-limiting examples of anti-angiogenic agents that may be used in combination with Compound 1 or a pharmaceutical composition thereof for treating a pancreatic cancer include VEGF antagonists, receptor antagonists, integrin antagonists (e.g., vitaxin, cilengitide, and S247), and VTAs/VDAs (e.g., fosbretabulin). VEGF antagonists include, but are not to, anti-VEGF antibodies (e.g., bevacizumab (branded/marketed as AVASTIN®) and ranibizumab (branded/marketed as LUCENTIS®)), VEGF traps (e.g., aflibercept), VEGF antisense or siRNA or miRNA, and aptamers (e.g., pegaptanib (branded/marketed as MACUGEN®)). Anti-angiogenic agents that are receptor antagonists include, but are not limited to, antibodies (e.g., ramucirumab) and kinase inhibitors (e.g., sunitinib, sorafenib, cediranib, panzopanib, vandetanib, axitinib, and AG-013958) such as tyrosine kinase inhibitors. Other non-limiting examples of anti-angiogenic agents include ATN-224, anecortave acetate (branded/marketed as RETAANE®), microtubule depolymerization inhibitor such as combretastatin A4 prodrug, and protein or protein fragment such as collagen 18 (endostatin).

Non-limiting examples of other therapies that may be administered to a subject in combination with Compound 1 or a pharmaceutical composition thereof for treating a pancreatic cancer include:

(1) a statin such as lovostatin (e.g., branded/marketed as MEVACOR®);
(2) an mTOR inhibitor such as sirolimus which is also known as Rapamycin (e.g., branded/marketed as RAPAMUNE®), temsirolimus (e.g., branded/marketed as TORISEL), evorolimus (e.g., branded/marketed as AFINITOR®), and deforolimus;
(3) a farnesyltransferase inhibitor agent such as tipifarnib (e.g., branded/marketed as ZARNESTRA®);
(4) an antifibrotic agent such as pirfenidone;
(5) a pegylated interferon such as PEG-interferon alfa-2b;
(6) a CNS stimulant such as methylphenidate (branded/marketed as RITALIN®);
(7) a HER-2 antagonist such as anti-HER-2 antibody (e.g., trastuzumab) and kinase inhibitor (e.g., lapatinib);
(8) an IGF-1 antagonist such as an anti-IGF-1 antibody (e.g., AVE1642 and IMC-A11) or an IGF-1 kinase inhibitor;
(9) EGFR/HER-1 antagonist such as an anti-EGFR antibody (e.g., cetuximab, panitumamab) or EGFR kinase inhibitor (e.g., erlotinib (e.g., branded/marketed as TARCEVA®), gefitinib);
(10) SRC antagonist such as bosutinib;
(11) cyclin dependent kinase (CDK) inhibitor such as seliciclib;
(12) Janus kinase 2 inhibitor such as lestaurtinib;
(13) proteasome inhibitor such as bortezomib;
(14) phosphodiesterase inhibitor such as anagrelide;
(15) inosine monophosphate dehydrogenase inhibitor such as tiazofurine;
(16) lipoxygenase inhibitor such as masoprocol;
(17) endothelin antagonist;
(18) retinoid receptor antagonist such as tretinoin or alitretinoin;
(19) immune modulator such as lenalidomide, pomalidomide, or thalidomide (e.g., branded/marketed as THALIDOMID®);
(20) kinase (eg, tyrosine kinase) inhibitor such as imatinib (e.g., branded/marketed as GLEEVEC®), dasatinib, erlotinib, nilotinib, gefitinib, sorafenib, sunitinib (e.g., branded/marketed as SUTENT®), lapatinib, AEE788, or TG100801;

(21) non-steroidal anti-inflammatory agent such as celecoxib (branded/marketed as CELEBREX®);
(22) human granulocyte colony-stimulating factor (G-CSF) such as filgrastim (branded/marketed as NEUPOGEN®);
(23) folinic acid or leucovorin calcium;
(24) integrin antagonist such as an integrin α5β1-antagonist (e.g., JSM6427);
(25) nuclear factor kappa beta (NF-κβ) antagonist such as OT-551, which is also an anti-oxidant;
(26) hedgehog inhibitor such as CUR61414, cyclopamine, GDC-0449, or anti-hedgehog antibody;
(27) histone deacetylase (HDAC) inhibitor such as SAHA (also known as vorinostat (branded/marketed as ZOLINZA®)), PCI-24781, SB939, CHR-3996, CRA-024781, ITF2357, JNJ-26481585, or PCI-24781;
(28) retinoid such as isotretinoin (e.g., branded/marketed as ACCUTANE®);
(29) hepatocyte growth factor/scatter factor (HGF/SF) antagonist such as HGF/SF monoclonal antibody (e.g., AMG 102);
(30) synthetic chemical such as antineoplaston;
(31) anti-diabetic such as rosiglitazone maleate (e.g., branded/marketed as AVANDIA®);
(32) antimalarial and amebicidal drug such as chloroquine (e.g., branded/marketed as ARALEN®);
(33) synthetic bradykinin such as RMP-7;
(34) platelet-derived growth factor receptor inhibitor such as SU-101;
(35) receptor tyrosine kinase inhibitors of Flk-1/KDR/VEGFR2, FGFR1 and PDGFR beta such as SU5416 and SU6668;
(36) anti-inflammatory agent such as sulfasalazine (e.g., branded/marketed as AZULFIDINE®); and (37) TGF-beta antisense therapy.

Non-limiting examples of other therapies that may be administered to a subject in combination with Compound 1 or a pharmaceutical composition thereof for treating a pancreatic cancer include: a synthetic nonapeptide analog of naturally occurring gonadotropin releasing hormone such as leuprolide acetate (branded/marketed as LUPRON); a non-steroidal, anti-androgen such as flutamide (branded/marketed as EULEXIN) or nilutamide (branded/marketed as NILANDRON®); a non-steroidal androgen receptor inhibitor such as bicalutamide (branded/marketed as CASODEX®); steroid hormone such as progesterone; anti-fungal agent such as Ketoconazole (branded/marketed as NIZORAL); glucocorticoid such as prednisone; estramustine phosphate sodium (branded/marketed as EMCYT®); and bisphosphonate such as pamidronate, alendronate, and risedronate.

Additional specific examples of therapies that may be used in combination with Compound 1 or a pharmaceutical composition thereof for treating a pancreatic cancer include, but are not limited to, agents associated with cancer immunotherapy (e.g., cytokines, interleukins, and cancer vaccines).

Specific examples of agents alleviating side-effects associated with a pancreatic cancer that can be used as therapies in combination with Compound 1 or a pharmaceutical composition thereof, include, but are not limited to: antiemetics, e.g., Ondansetron hydrochloride (branded/marketed as ZOFRAN®), Granisetron hydrochloride (branded/marketed as KYTRIL®), Lorazepam (branded/marketed as ATIVAN®) and Dexamethasone (branded/marketed as DECADRON®).

In certain aspects, combination therapies provided herein for treating a pancreatic cancer comprise administering Compound 1 or a pharmaceutical composition thereof in combination with one or more agents used to treat and/or manage a side effect, such as, bleeding (usually transient, low-grade epistaxis), arterial and venous thrombosis, hypertension, delayed wound healing, asymptomatic proteinuria, nasal septal perforation, reversible posterior leukoencephalopathy syndrome in association with hypertension, lightheadedness, ataxia, headache, hoarseness, nausea, vomiting, diarrhea, rash, subungual hemorrhage, myelodysplastic syndromes, myelosuppression, fatigue, hypothyroidism, QT interval prolongation, or heart failure.

In certain aspects, Compound 1 or a pharmaceutical composition thereof is not used in combination with a drug that is primarily metabolized by CYP2D6 (such as an antidepressant (e.g, a tricyclic antidepressant, a selective serotonin reuptake inhibitor, and the like), an antipsychotic, a beta-adrenergic receptor blocker, or certain types of anti-arrhythmics) to treat a pancreatic cancer.

Kits

Provided herein is a pharmaceutical pack or kit comprising one or more containers filled with Compound 1 or a pharmaceutical composition thereof. Additionally, one or more other therapies useful for the treatment of a pancreatic cancer, or other relevant agents can also be included in the pharmaceutical pack or kit. Also provided herein is a pharmaceutical pack or kit comprising one or more containers filled with one or more of the ingredients of the pharmaceutical compositions described herein. Optionally associated with such kits can be a notice in the form prescribed by a governmental agency regulating the manufacture, use or sale of pharmaceuticals or biological products, which notice reflects approval by the agency of manufacture, use or sale for human administration.

Without regard to whether a document cited herein was specifically and individually indicated as being incorporated by reference, all documents referred to herein are incorporated by reference into the present application for any and all purposes to the same extent as if each individual reference was fully set forth herein.

Having now fully described the subject matter of the claims, it will be understood by those having ordinary skill in the art that the same can be performed within a wide range of equivalents without affecting the scope of the subject matter or aspects described herein. It is intended that the appended claims be interpreted to include all such equivalents.

Examples

The following examples are intended to illustrate the various methods of the invention, but in no way limit the scope of the invention.

The materials and methods used in the following examples were either available from commercial sources or were obtained by methods known to those skilled in the art following known procedures or procedures described in the indicated references.

Compound 1 was prepared according to the procedure described in International Publication No. WO2014/081906.

Compound 2 refers to 6-(5,6-difluoro-2-methyl-1H-benzo[d]imidazol-1-yl)-N-(4-(trifluoromethyl)phenyl)pyrazin-2-amine, a known inhibitor of BMI-1 function, prepared according to the procedure described in International Publication No. WO2015/076800.

Cell Lines, Cell Culture, and Viability Assays

Authenticated human cell lines were purchased from ATCC, utilized within 30 cumulative passages of initial purchase. Murine KPC lines were generated and used within 30 cumulative passages. J1002 cells were generated from KPBBR mice and used within 15 cumulative passages. All cell lines consistently tested negative for mycoplasma throughout the period of experimentation using the MycoAlert Mycoplasma Detection Kit (Lonza; LT07-318). Cells were maintained under standard conditions at 37° C. and 5% $CO_2$ and were grown in DMEM (Life Technologies, 12430-054) supplemented with penicillin and streptomycin (Corning, 30-003-CI), and 10% FBS (Life Technologies, 10438-034).

Figure 10A:
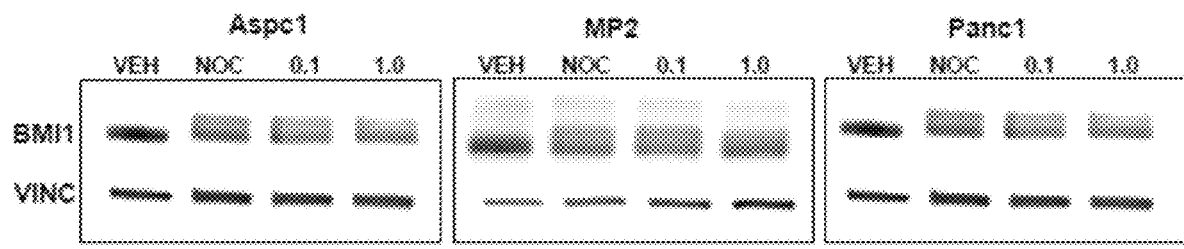
FIG. 10a is a series of western blots showing BMI-1 levels in Aspc1, MiaPaCa-2, and Panc1 cells treated for 24 hours with vehicle (VEH), 0.1 uM nocodazole (NOC), 0.1 µM Compound 1 (0.1), or 1.0 µM Compound 1 (1.0) relative to vinculin (VINC) loading control.
Figure 10B:
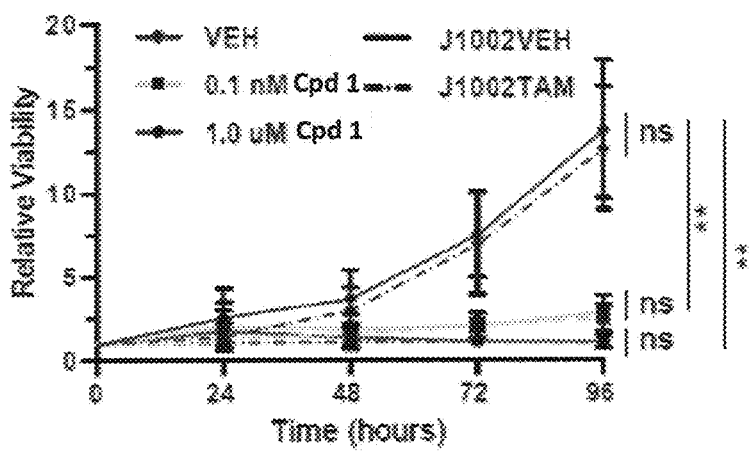
FIG. 10b is a graph of relative viability of J1002VEH and J1002TAM cells treated with vehicle (VEH), 0.1 µM Compound 1 (Cpd 1), or 1.0 µM Compound 1 (Cpd 1) over 96 hours.

For proliferation curves, cells were plated in 96-well plates (Corning, 3603) and allowed to seed overnight. Replicate plates were plated for each time point since viability measurements were an endpoint procedure. The following day, cells were treated with Compound at indicated concentrations and treated with DMSO at the highest used concentration (always below 0.003%). Cells were treated for 96 hours, and viability was determined every 24 hours using AlamarBlue reagent (BioRad, BUF012B). Briefly, 10 µL of AlamarBlue was added to each well (100 µL), mixed briefly, and allowed to incubate at 37° C. and 5% $CO_2$ for 4 hours. Following incubation, fluorescence was measured on a Promega multimode microplate reader. For analysis, background levels were subtracted from raw results, which were then normalized to be represented as a fold change compared to DMSO-treated cells on Day 0. All assays were carried out in at least triplicate with 4-8 technical replicates per treatment group, per experiment. (FIG. 1a and FIG. 10b)

Figure 10C:
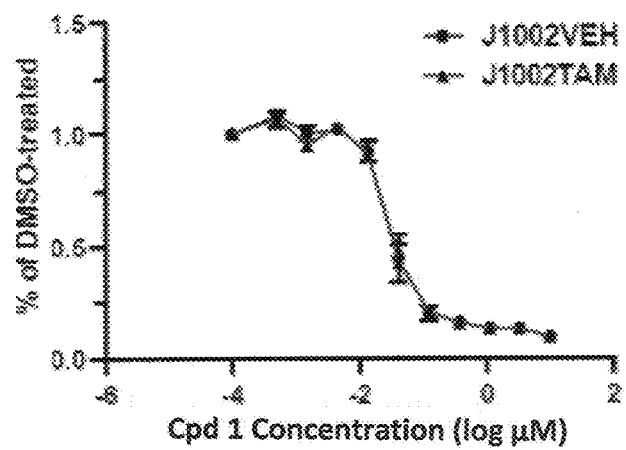
FIG. 10c is a graph of dose response curves for J1002VEH and J1002TAM cells treated with Compound 1 for 72 hours.

For dose response curves, cells were plated in 96-well plates (Corning, 3603) and allowed to seed overnight. The following day, cells were treated with Compound 1. Dose response curves began at 10 µM, were decreased in 3-fold increments, and ended with DMSO at the highest used concentration (always below 0.03%). Cells were treated for 72 hours and then viability was determined using AlamarBlue reagent (BioRad, BUF012B). Briefly, 10 µL of AlamarBlue was added to each well (100 µL), mixed briefly, and allowed to incubate at 37° C. and 5% $CO_2$ for 4 hours. Following incubation, fluorescence was measured on a Promega multimode microplate reader. For analysis, background levels were subtracted from raw results, which were then normalized to be represented as a percent of DMSO-treated cells. All assays were carried out in at least triplicate with 4-8 technical replicates per experiment. (FIG. 10c)

Cell Cycle Analysis

Cells were seeded into 12-well or 6-well plates such that 16 hours later they would be approximately 30-50% confluent. Cells were then treated for 24 hours with either DMSO (<0.003%), Compound 1 (100 nM or 1 µM), or 100 nM nocodazole (Sigma, M1404). Following treatment, cells were harvested and fixed in ice-cold 70% ethanol for a minimum of one hour. Following fixation, cells were resuspended in PBS+2% FBS+3 µM DAPI (BioLegend, 422801) or 0.25 µg 7-AAD (BD Pharmingen, 559925), and analyzed on a MACSQuant® Analyzer 10 (Miltenyi Biotec) or BD LSR II™. For cell cycle analysis time course experiments, cells were prepared as described above, except treated for 24, 48, or 72 hours. Data was analyzed using FlowJo software. Percent populations in G2/M were identified using the univariate cell cycle platform offered by FlowJo software. Percent populations >4N were determined by gating above the 4N population of DMSO-treated cells. (FIG. 1b, FIG. 1c, FIG. 2a, FIG. 2b, FIG. 10e, and FIG. 10g)

Flow Cytometry for Intracellular Proteins

Figure 1D:
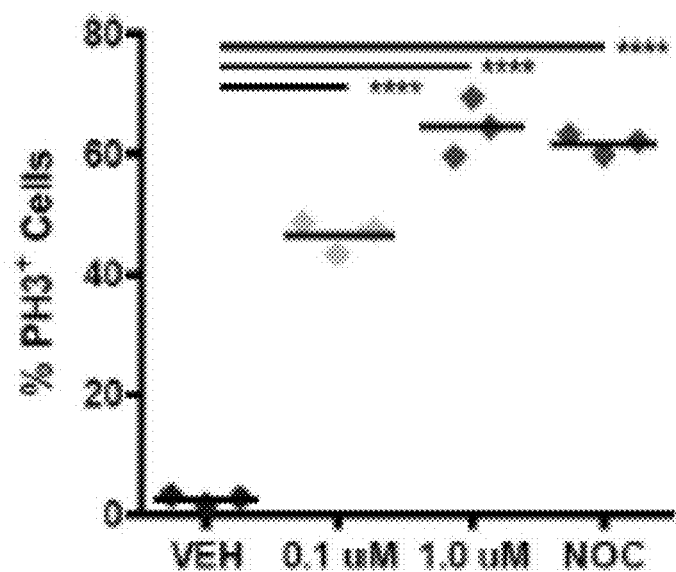
FIG. 1d is a plot of the percent of Aspc1 cells in mitosis (PH3+/4N DNA content) after treatment for 24 hours with DMSO, Compound 1 (0.1 μM or 1.0 μM), or 0.1 μM nocodazole (NOC).
Figure 2A:
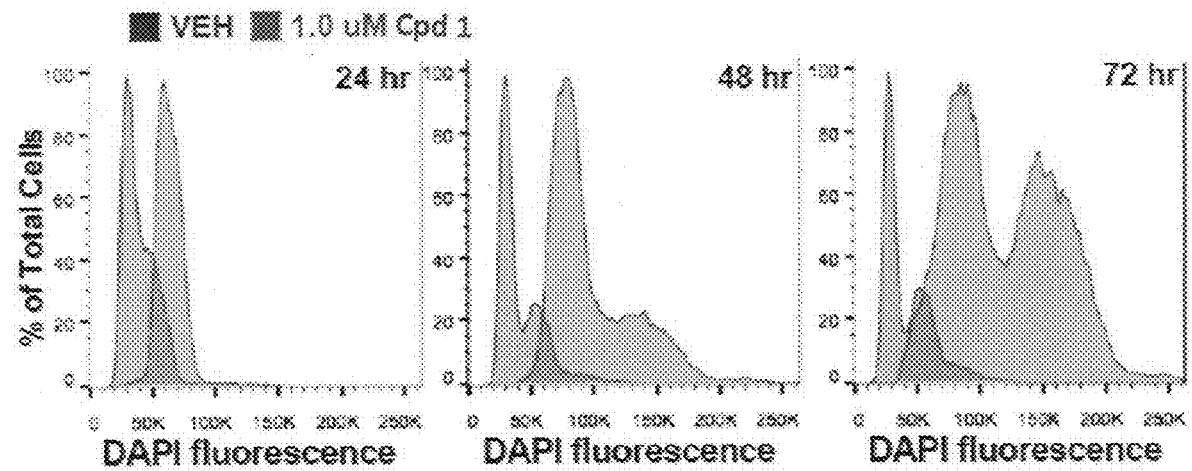
FIG. 2a depicts representative histograms of DNA content measured by DAPI fluorescence in Aspc1 cells treated with vehicle or Compound 1 (1.0 μM) at 24 hour, 48 hour, and 72 hour timepoints.
Figure 2B:
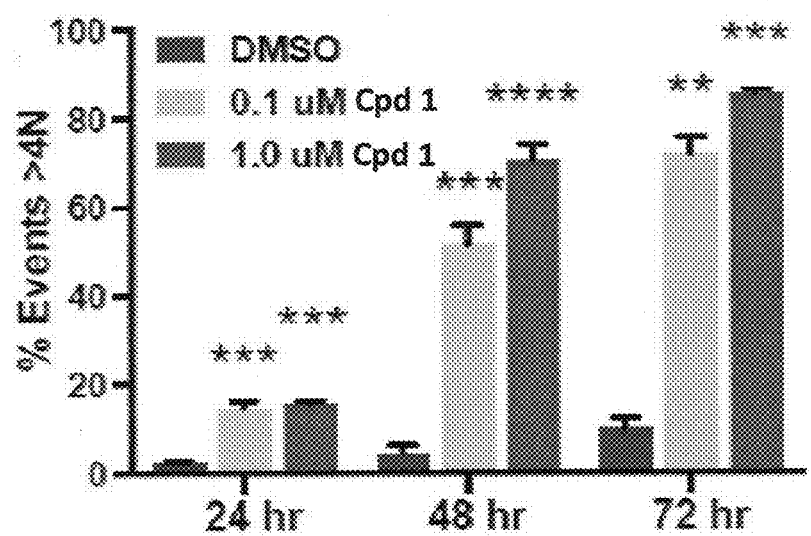
FIG. 2b is a graph of the percent of Aspc1 cells with DNA content >4N after treatment with DMSO or Compound 1 (0.1 μM or 1.0 μM) at 24 hour, 48 hour, 72 hour timepoints.
Figure 3A:
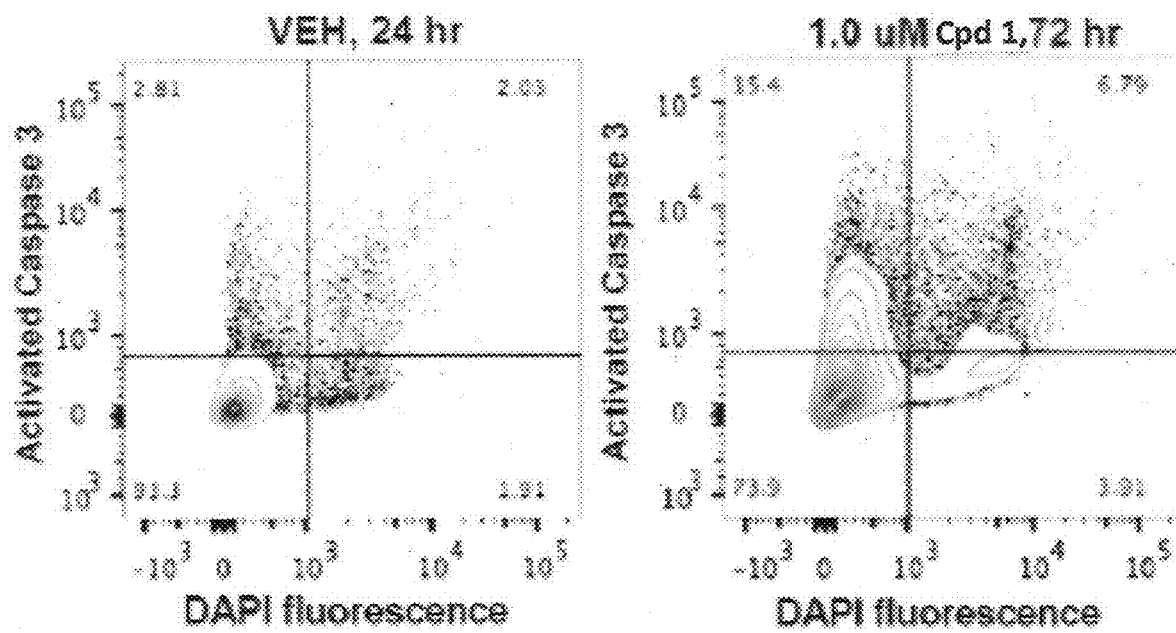
FIG. 3a depicts representative flow cytometry scatter plots showing induction of apoptosis in Aspc1 cells following treatment with DMSO for 24 hours, or 1.0 μM Compound 1 at 72 hours. Unfixed cells were stained for active caspase 3 and DAPI to distinguish viable cells (lower left) from early apoptosis (top left), late apoptosis (top right), and necrosis (lower right).

For phospho-Histone H3 (PH3) staining, cells were fixed and permeabilized according to manufacturer's instructions using the eBioscience Foxp3/Transcription Factor Staining Buffer Set (ThermoFisher, 00-5523-00). Cells were blocked with Fc Block (BD Biosciences, 564220) and stained using a PH3 (Ser10) antibody (BioLegend, 650805) with 5 uL per million cells (45 min, room temp, dark). Samples were analyzed on a BD Fortessa™ and analyzed by FlowJo software. (FIG. 1d and FIG. 3a)

Figure 3B:
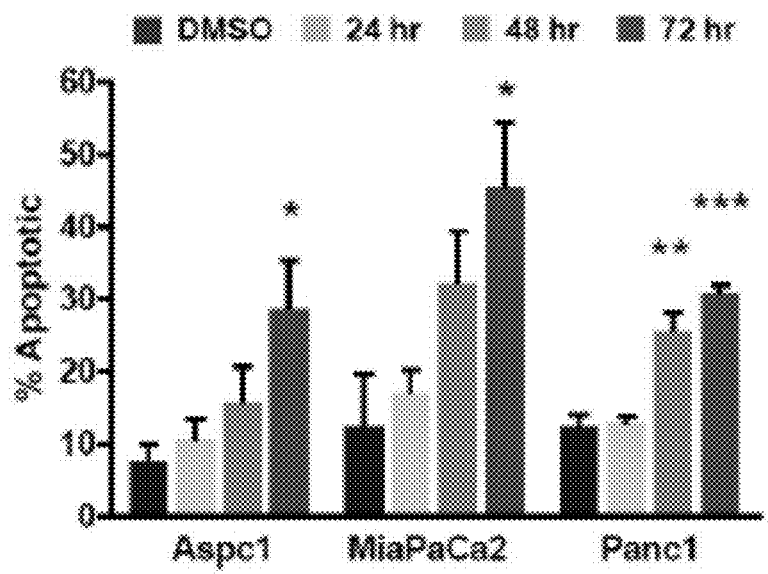
FIG. 3b is a graph of total apoptotic Aspc1 cells (active caspase 3+) quantified for DMSO or Compound at 24 hour, 48 hour, and 72 hour timepoints.

For active Caspase-3 (ActCasp3) staining, the Caspase 3 (active) FITC Staining Kit (Abcam, ab65613) was used according to manufacturer's instructions. Cells were seeded in 12-well plates such that ~16 hours later they would be approximately 50-60% confluent. Cells were then treated with drugs at the indicated concentrations, or DMSO vehicle, for 24 hours, at which point they were harvested, stained with FITC-DEVD-FMK (1 µL/sample, 1 hour, room temp, dark), washed, and then stained with DAPI for analysis. Samples were analyzed on a BD LSR II™ and analyzed by FlowJo software. (FIG. 3a and FIG. 3b)

Western Blotting

Figure 5A:
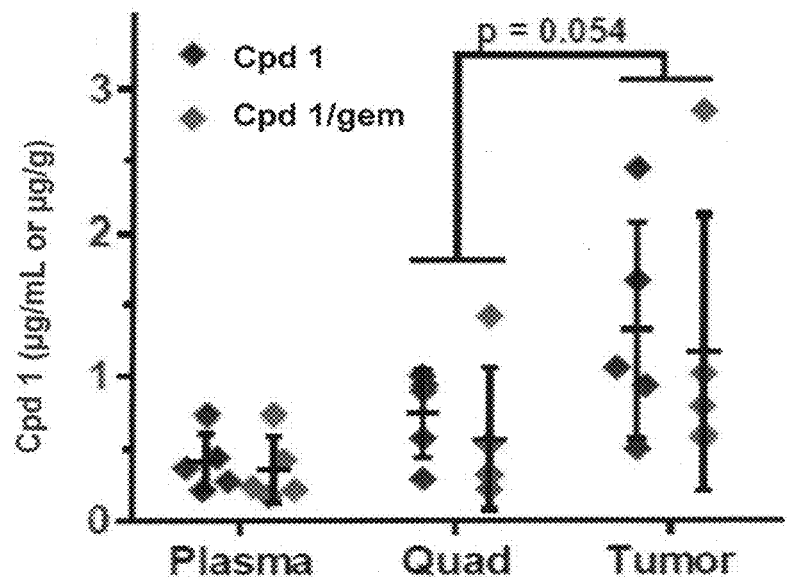
FIG. 5a is a plot of Compound 1 concentrations in plasma, quadriceps, and PDA tissues from KPC mice, 24 hours following a single oral dose of Compound 1 (10 mg/kg), alone or in combination with gemcitabine (100 mg/kg).
Figure 5B:
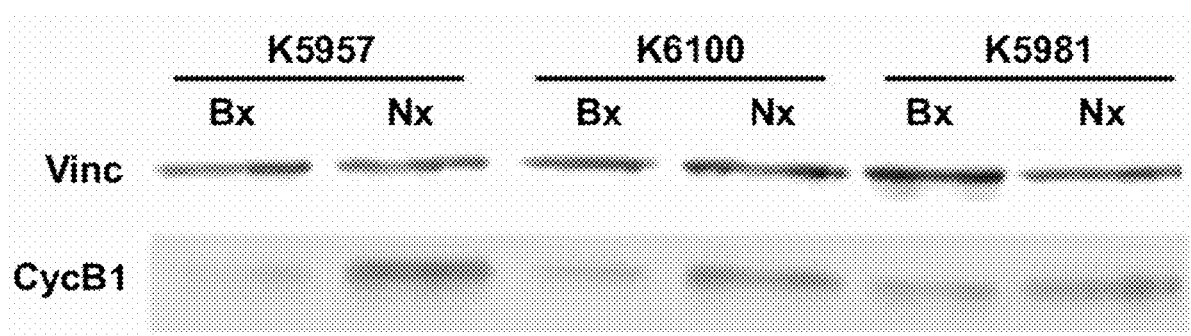
FIG. 5b is a western blot for CYCLIN B1 on tumors from KPC mice treated with 10 mg/kg of Compound 1. Tumor biopsy samples (Bx) were acquired 48 hours prior to first dose, and compared to samples acquired at necropsy (Nx) 24 hours after the third dose.
Figure 5C:
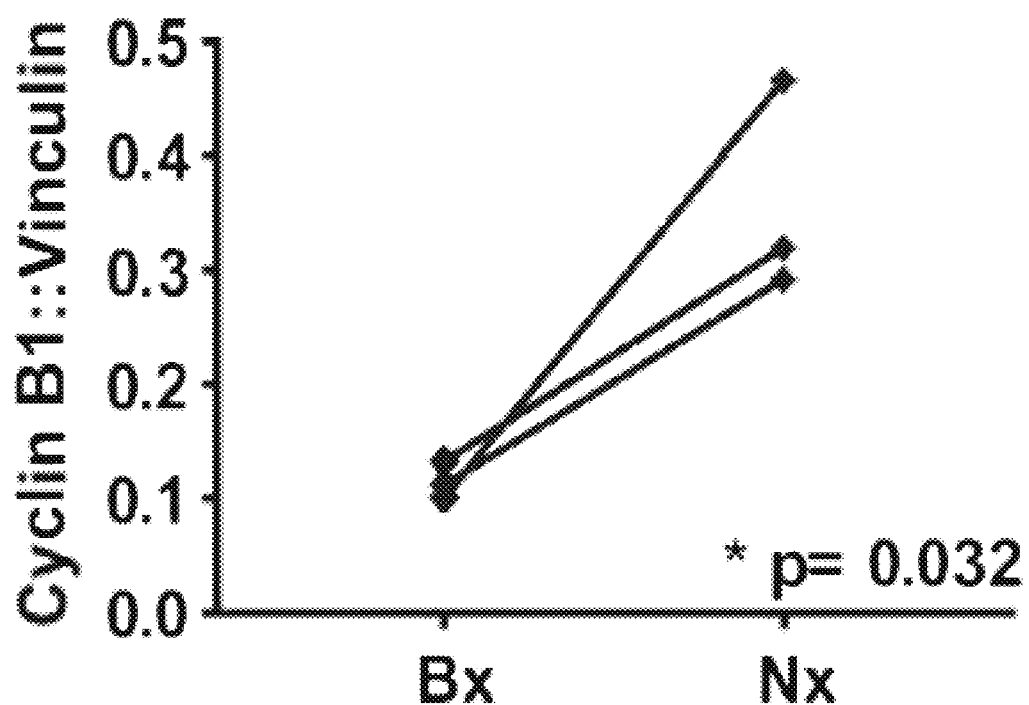
FIG. 5c is a graph quantifying CYCLIN B1 (CycB1) from FIG. 5b, normalized to VINCULIN (Vinc).
Figure 11A:
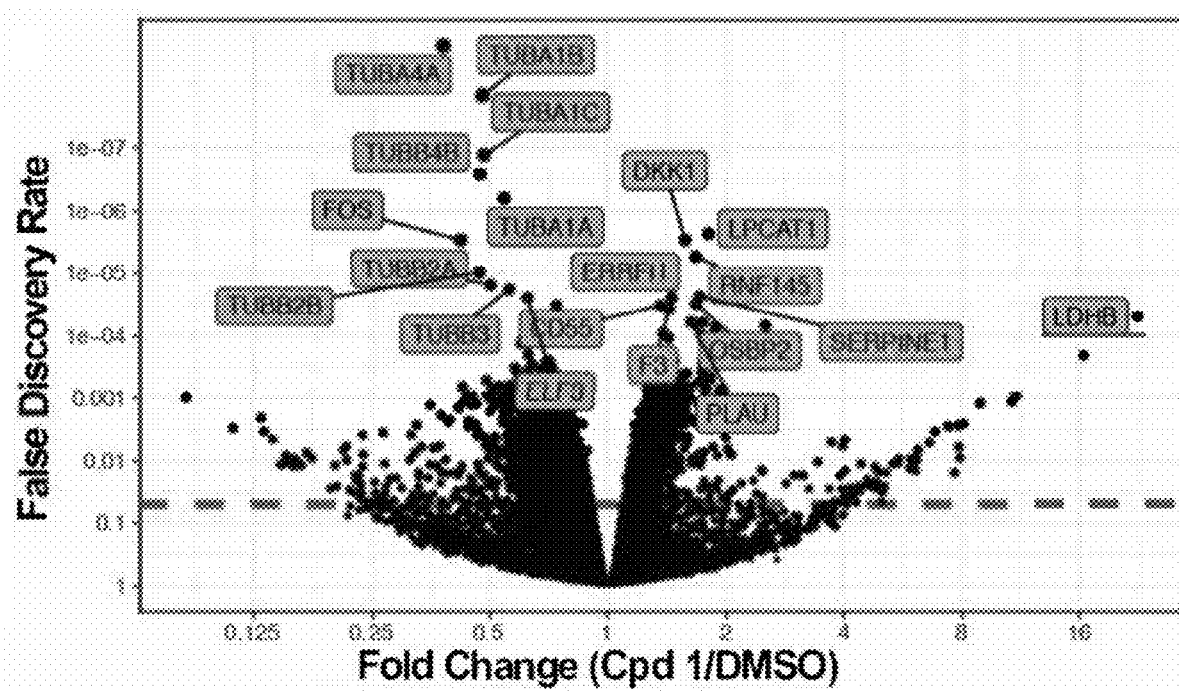
FIG. 11a is a plot of differentially expressed genes measured by RNA-seq on Aspc1 cells treated with DMSO or 1 µM Compound 1 (Cpd 1), integrated over 8, 16, and 24 hour timepoints.
Figure 11B:
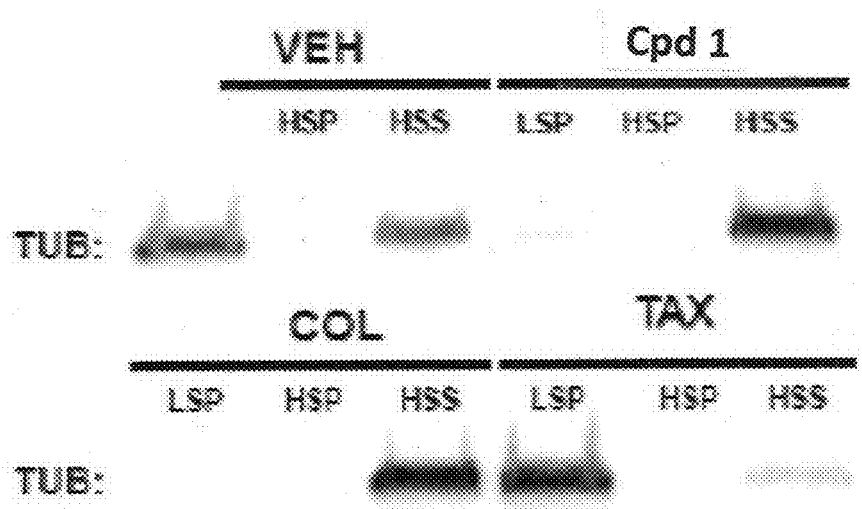
FIG. 11b is a western blot showing free tubulin from Aspc1 cells treated with vehicle (VEH), 3.0 µM Compound 1 (Cpd 1), 1.0 µM colchicine (COL), or 1.0 µM paclitaxel (TAX) for 2 hours. Following treatment, cell lysates were fractionated by centrifugation in order to separate free tubulin from microtubules. LSP=Low Speed Pellet (1,000× g, 5 min), HSP=High Speed Pellet (100,000×g, 1 hour), HSS=High Speed Supernatant (100,000×g, 1 hour).
Figure 11C:
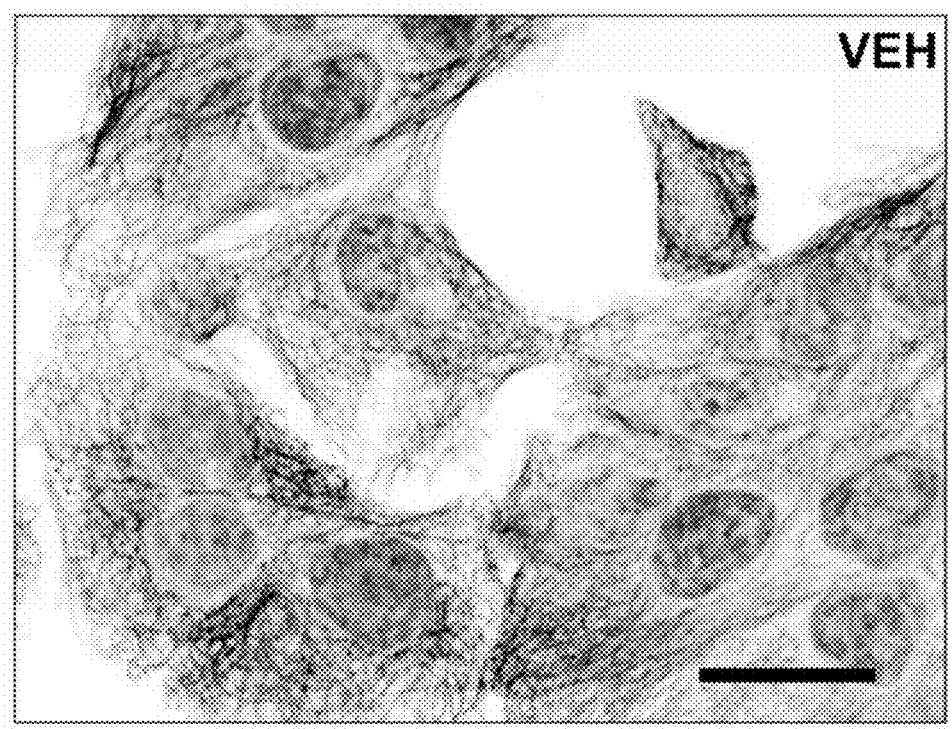
FIG. 11c is an image of tubulin and DAPI in Aspc1 cells treated with vehicle (VEH) for 24 hours.
Figure 11D:
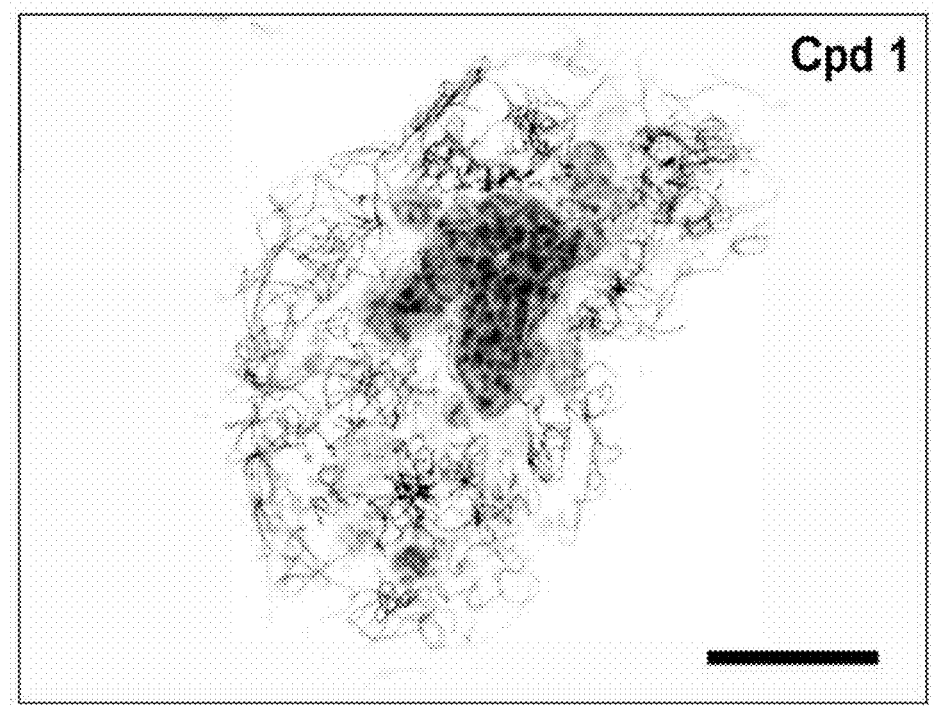
FIG. 11d is an image of tubulin and DAPI in Aspc1 cells treated with Compound 1 (Cpd 1) for 24 hours.

Western blotting was carried out on lysates isolated from treated cells. Cells were lysed using RIPA buffer (50 mM Tris, pH 7.4, 150 mM NaCl, 1% Nonidet P-40, 0.1% SDS, 0.5% deoxycholate) supplemented with cOmplete™ EDTA-free Protease Inhibitor Cocktail (Sigma, 11836170001) and Halt™ Phosphatase Inhibitor Cocktail (ThermoFisher, 78420). Lysates were quantified using the Pierce BCA Protein Assay Kit (ThermoFisher, 23227), diluted in SDS sample buffer, resolved by SDS-PAGE (15-30 µg/sample), and transferred onto PVDF membranes. Membranes were blocked with 5% w/v nonfat dry milk in TBS-T (0.1% Tween20) and primary antibodies were incubated overnight at 4° C., diluted in 5% BSA in TBS-T at the indicated concentrations. HRP-conjugated secondary antibodies were incubated in blocking buffer for 1 hour at room temperature before detection using Super Digital-ECL™ substrate solution (Kindle Biosciences, R1002). (FIG. 5b, FIG. 10a and FIG. 11b)

Western Blot Antibodies:
Bmi1: Cell Signaling, #5856, 1:1000
Vinculin: Cell Signaling, #4650S, 1:1000
Beta-tubulin: Cell Signaling, #2146S, 1:1000

P-Glycoprotein Substrate Activity Experiment

Figure 4A:
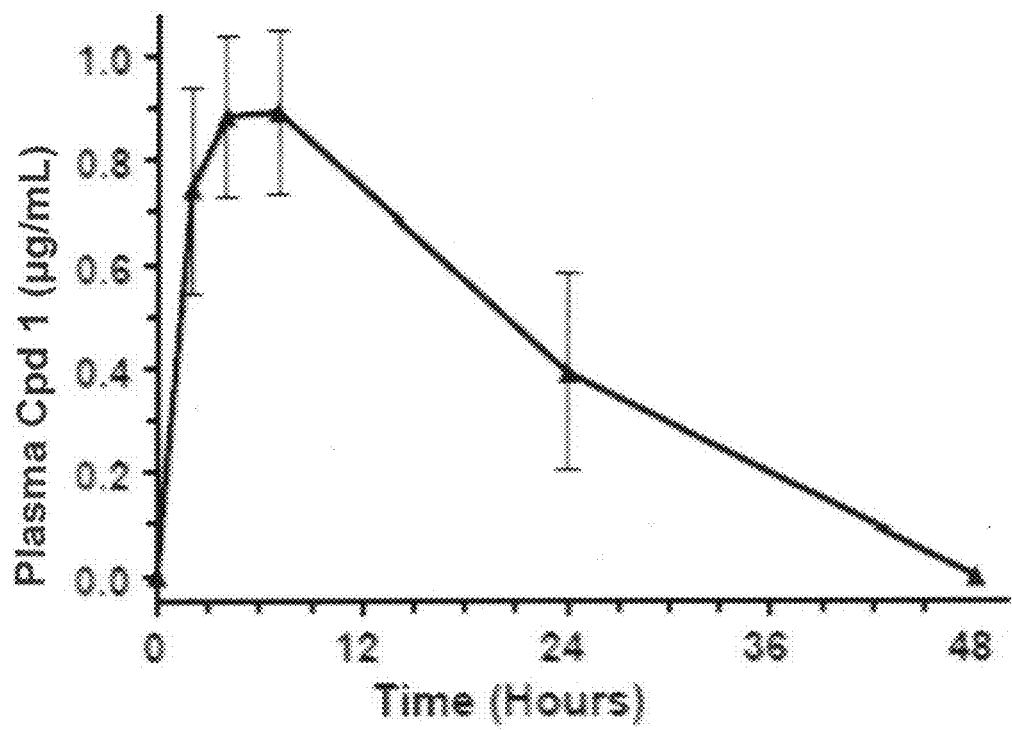
FIG. 4a is a graph of plasma levels of Compound 1 in mice measured by mass spectrometry at baseline, or 2, 4, 7, 24, or 48 hours following a single oral dose of Compound 1 (10 mg/kg).
Figure 4B:
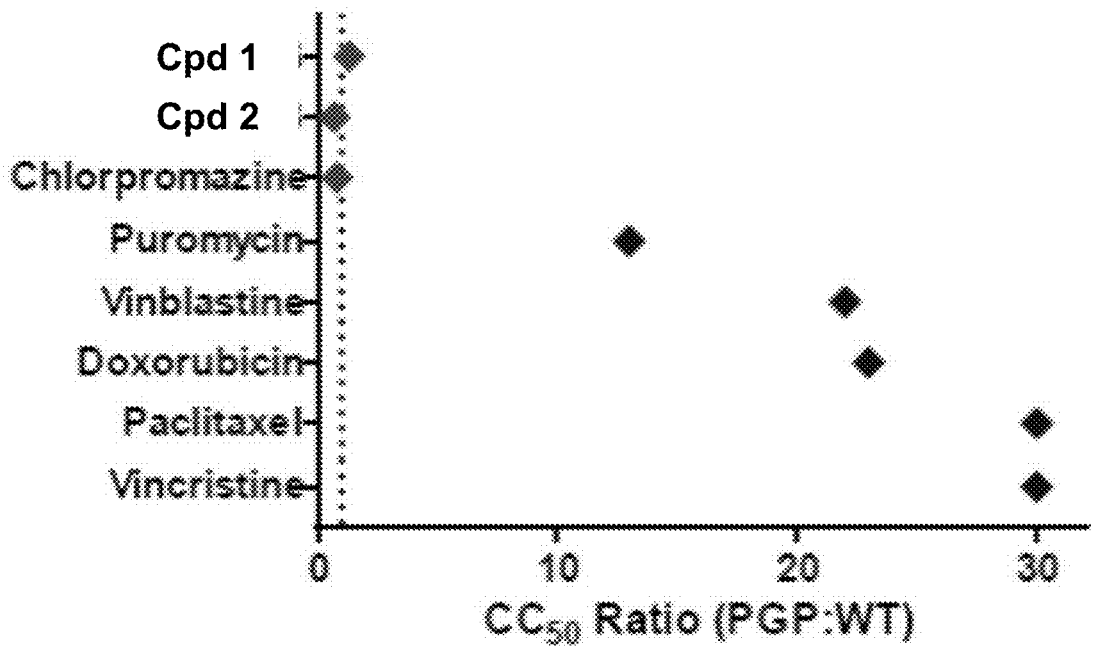
FIG. 4b is a plot of the ratio of $CC_{50}$ values for treatment of MDCK-P-gp vs MDCK-WT cells with Compound 1, Compound 2, chlorpromazine, puromycin, vinblastine, doxorubicin, paclitaxel, and vincristine.

MDCKII-mdr1 and MDCKII-wt cells were purchased from the Netherlands Cancer Institute, NKI-AVL. The cells were cultivated in Dulbecco's modified essential medium (DMEM), supplemented with 10% FBS and 1% Penn-Strep, and used between passage 3-9. Cells were seeded at a density of 3×103 cells/well in 96-well tissue culture treated plates. After 4 hours to allow cells to attach, cells were treated with test compound in the presence or absence of the P-glycoprotein inhibitor Valspodar. The plates were incubated at 37° C., 5% $CO_2$ for 72 hours and ATP was measured vialuminescence using CellTiter-Glo® reagent (Promega). (FIG. 4b)

RNA Sequencing

Approximately 1.75 µg total RNA per sample underwent poly-A pull-down for mRNA enrichment, which then was used as input for the Illumina TruSeq RNA prep kit. Samples were prepared for the Illumina HiSeq 4000 platform using a Beckmann-Coulter Roboter and the SPRworks Fragment Library Kit I. PCR using the KAPA PCR Amplification Kit was carried out. The libraries were then sequenced by the Columbia Genome Center to generate 30 million single-end reads of 100 bp length. (FIG. 11a)

RNA-Seq Analysis

Reads were mapped to the human reference genome (NCBI/build 37.2) using the STAR aligner (version 2.4.2) (Dobin A, Davis Calif., Schlesinger F, et al. STAR: Ultrafast Universal RNA-Seq Aligner, Bioinformatics 2013; 29:15-21) and were quantified at the gene level using the summarizeOverlaps function from the R package 'GenomicAlignments' (Lawrence M, Huber W, Pages H, et al. Software for computing and annotating genomic ranges, PLoS Computational Biology 2013; 9:e1003118) with information on gene annotations from the R package 'TxDb.Hsapiens. UCSC.hg19.knownGene' (Carlson M, Maintainer BP. TxDb.Hsapiens.UCSC.hg19.knownGene:Annotation Package for TxDb Object(s). 2015). RNA-seq data were deposited to GEO (ID: GSE118441). (FIG. 11a)

Differential Gene Expression (DEG)

Differential gene expression analysis between the indicated conditions was carried out using the voom-limma frameworks implemented the R package 'limma' (Ritchie M E, Phipson B, Wu D, et al. Limma powers differential expression analyses for RNA-sequencing and microarray studies, Nucleic Acids Research 2015; 43:e47). The overall effect of Compound 1 treatment as compared to DMSO was assessed using a multivariate design accounting for both treatment and time point.

Gene Set Enrichment

The R implementation of single sample GSEA: gene set variation analysis with default parameters was used (Hanzelmann S, Castelo R, Guinney J. GSVA: gene set variation analysis for microarray and RNA-seq data, BMC Bioinformatics 2013; 14:7). Raw counts from RNA sequencing were normalized to account for different library sizes, and the variance was stabilized by fitting the dispersion to a negative-binomial distribution as implemented in the DESeq2 R package (Love M I, Huber W, Anders S. Moderated estimation of fold change and dispersion for RNA-seq data with DESeq2, Genome Biol 2014; 15:550). Gene sets were retrieved from the MSigDb v6.0 modules HALLMARK, C2 canonical pathways and C6 oncogenic signatures (Subramanian A, Tamayo P, Mootha V K, et al. Gene set enrichment analysis: a knowledge-based approach for interpreting genome-wide expression profiles, Proc Natl Acad Sci USA 2005; 102:15545-50 and Liberzon A, Subramanian A, Pinchback R, et al. Molecular signatures database (MSigDB) 3.0, Bioinformatics 2011; 27:1739-40). Differential enrichment analysis of these gene sets between DMSO and Compound 1 treatment was carried out using the limma R package (Ritchie M E, Phipson B, Wu D, et al. limma powers differential expression analyses for RNA-sequencing and microarray studies, Nucleic Acids Res 2015; 43:e47) and a false discovery rate (FDR)<0.1 was considered significant. Single sample enrichment results for select pathways were depicted in a heatmap using the pheatmap R package (http://CRAN R-project org/package=pheatmap R package version 2017; 1:2). (FIG. 11a)

Gene Set Signatures:

| Abbreviation | Full Name |
| --- | --- |
| APC/c deg. of Cyc B | REACTOME_APC_C_CDC20_MEDIATED_DEGRADATION_OF_CYCLIN_B |
| APC/c late anaphase | REACTOME_CONVERSION_FROM_APC_C_CDC20_TO_APC_C_CDH1_IN_LATE_ANAPHASE |
| phosphorylation of APC/c | REACTOME_PHOSPHORYLATION_OF_THE_APC_C |
| APC/c deg. of NEK2A | REACTOME_APC_CDC20_MEDIATED_DEGRADATION_OF_NEK2A |
| Reg. of mitosis | REACTOME_REGULATION_OF_MITOTIC_CELL_CYCLE |
| POL switching | REACTOME_POL_SWITCHING |
| DNA elongation | REACTOME_DNA_STRAND_ELONGATION |
| G1/S Phases | SA_G1_AND_S_PHASES |
| G1/S Transcription | REACTOME_G1_S_SPECIFIC_TRANSCRIPTION |
| DNA unwinding | REACTOME_UNWINDING_OF_DNA |

Cell-Free Tubulin Polymerization Assay

Figure 11E:
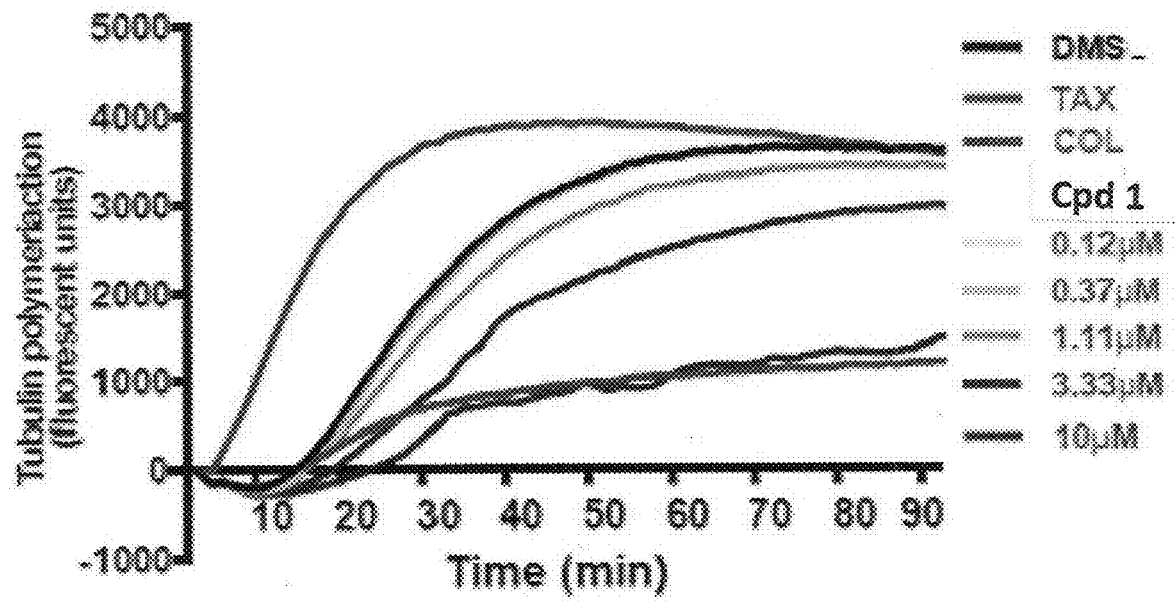
FIG. 11e is a graph of tubulin polymerization assay over time for cells treated with vehicle (DMS), tamoxifen (TAX), carboplatin (COL), and Compound 1 (0.12 µM, 0.37 µM, 1.11 µM, 3.33 µM, and 10 µM).
Figure 11F:
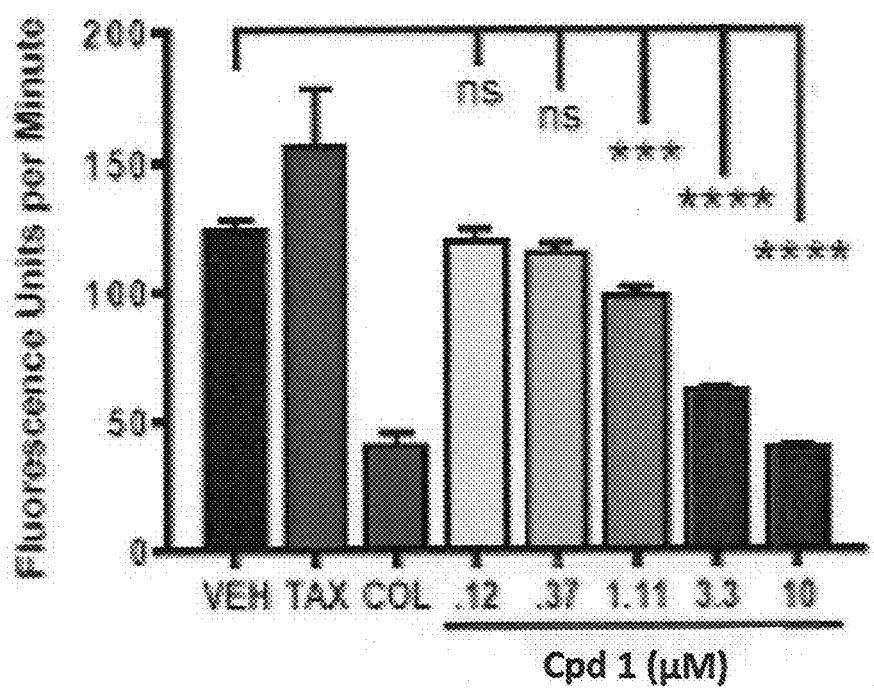
FIG. 11f is a graph of fluorescence units/minute represented in FIG. 11e.

Assays were carried out according to manufacturer's recommendations using the fluorescence-based tubulin polymerization assay kit from Cytoskeleton (#BK011P) which uses >99% pure tubulin from porcine brain. All drugs used were dissolved in DMSO and then diluted in ultrapure water to 10× final concentration. Final percentage of DMSO was kept constant for all samples. Tubulin was prepared by resuspension at 2 mg/mL in 80 mM PIPES pH 6.9, 2.0 mM $MgCl_2$, 0.5 mM EGTA, 1.0 mM GTP, 15% glycerol, and 10 μM fluorescent reporter. All drug samples (10×) were added to a pre-warmed half-area 96-well plate (Corning Costar, 3686) in duplicate, and then warmed to 37° C. for 1 min. Tubulin (50 μL/well) was then added to all wells, and the plate was placed in a plate reader pre-warmed to 37° C. The plate was mixed by medium, orbital shaking for 5 seconds, and fluorescence measured every 60 seconds for 90 minutes (Ex: 340-360+/−20 nm, Em: 410-460 nm+/−20 nm) in a BioTek Synergy 2 plate reader. Polymerization rates (fluorescence units/minute) were determined by measuring the maximal slope (by linear regression) of the linear portion of the growth phase of the polymerization curve. (FIG. 11e and FIG. 11f)

Analysis of Free Tubulin Content

Free heterodimer tubulin was separated from tubulin incorporated into microtubules according to manufacturer's recommendations using the Microtubule/Tubulin In Vivo Assay Biochem Kit (Cytoskeleton, #BK038). Cells were seeded in 12-well plates such that ~16 hours later they would be approximately 50-60% confluent. Cells were treated with drugs at the indicated concentrations, or DMSO vehicle, for 2 hours, at which point they were washed once with PBS and harvested. All steps of this assay were carried out at 37° C. in order to preserve microtubule mass. Cells were lysed in Cytoskeleton's Lysis and Microtubule Stabilization Buffer (LMS01) supplemented with 0.1 mM GTP, 1.0 mM ATP, and 1× protease inhibitor cocktail (#PIC02). Samples were centrifuged at 1,000×g for 5 minutes at 37° C. The supernatant was carefully collected for ultracentrifugation and the low speed pellet (LSP) was suspended in SDS sample buffer (SDS01) and frozen at −20° C. for later analysis by western blot. The low speed supernatant was centrifuged at 100,000×g for 60 minutes at 37° C. The supernatant (high speed supernatant, HSS) was carefully collected, resuspended in SDS sample buffer, and frozen at −20° C. for later analysis by western blot. The pellet (high speed pellet, HSP) was first dissolved in 1× Microtubule Depolymerization Buffer (BUF01) for 15 minutes, resuspended in SDS sample buffer, and frozen at −20° C. for later analysis by western blot. (FIG. 11b)

Immunocytochemistry

Cells were seeded onto glass coverslips in 12-well plates. Coverslips were prepared by soaking in 1N HCl (60° C., 6 hours), washing in 70% ethanol, and coating with poly-l-lysine (Sigma, P5899) according to manufacturer's instructions. Cells were seeded such that they would be 50% confluent the following day. Cells were then treated with vehicle (DMSO, <0.003%) or 1 μM Compound 1 and incubated for 24 hours. Following treatment, cells were washed with TBS and free tubulin was extracted with Brinkley Buffer 1980 (80 mM PIPES pH 6.8, 1 mM $MgCl_2$, 1 mM EGTA) supplemented with 4 mM EGTA and 0.5% Triton-X (30 seconds). After extraction, cells were fixed for 20 minutes in 4% formaldehyde diluted in Cytoskeleton Buffer (10 mM MES pH 6.1, 138 mM KCl, 3 mM $MgCl_2$, 2 mM EGTA) supplemented with 0.32M sucrose. Following fixation, cells were washed with TBS and then blocked in TBS-T (0.1% Triton-X)+2% BSA+22.52 mg/mL glycine for 30 minutes. The beta-tubulin antibody was incubated overnight at 4° C. (Abcam179513, 1:1000), followed by incubation with secondary antibody for one hour at room temperature using a goat anti-rabbit 594 secondary antibody (Life Technologies, A11012) at 1:500. All washes were done with TBS-T and all blocking and antibody incubations were done in TBS-T (0.1% Triton-X)+2% BSA+22.52 mg/mL glycine. After staining, cells were incubated with DAPI (BioLegend, 422801) at 300 nM for 5 min, washed, and mounted with ProLong Diamond Antifade Mountant (Invitrogen, P36965). Slides were left to dry for 24 hours at room temperature and then stored at 4° C. in the dark until image acquisition.

Figure 10D:
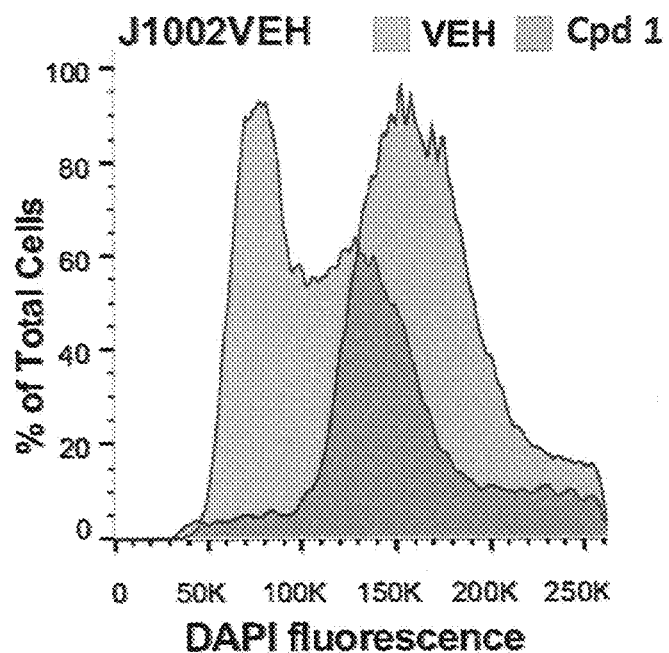
FIG. 10d depicts representative DNA histograms for J1002VEH cells treated for 24 hours with vehicle (VEH) or 1.0 µM Compound 1 (Cpd 1).
Figure 10E:
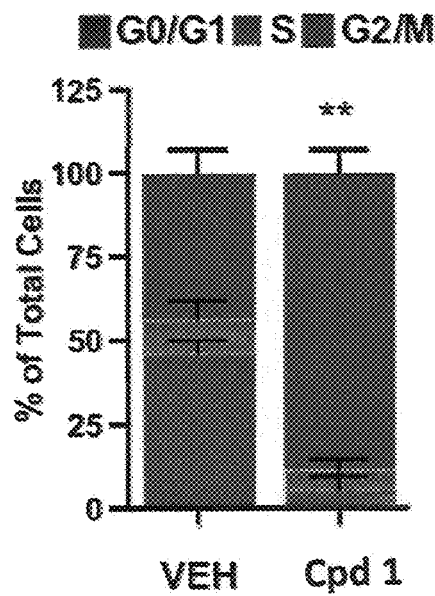
FIG. 10e is a graph of the percent of J1002VEH cells in G0/G1 phase, S phase, and G2/M phase following 24 hours after treatment with vehicle (VEH) or 1.0 µM Compound 1 (Cpd 1).
Figure 10F:
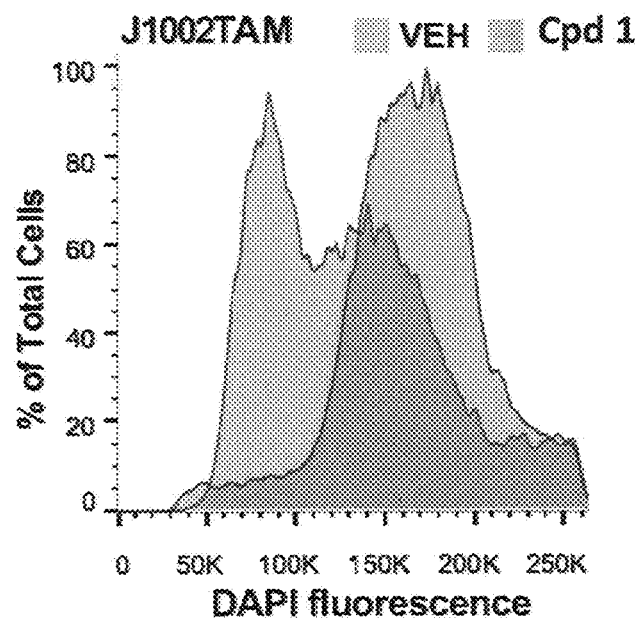
FIG. 10f depicts representative DNA histograms for J1002TAM cells treated for 24 hours with vehicle (VEH) or 1.0 µM Compound 1 (Cpd 1).
Figure 10G:
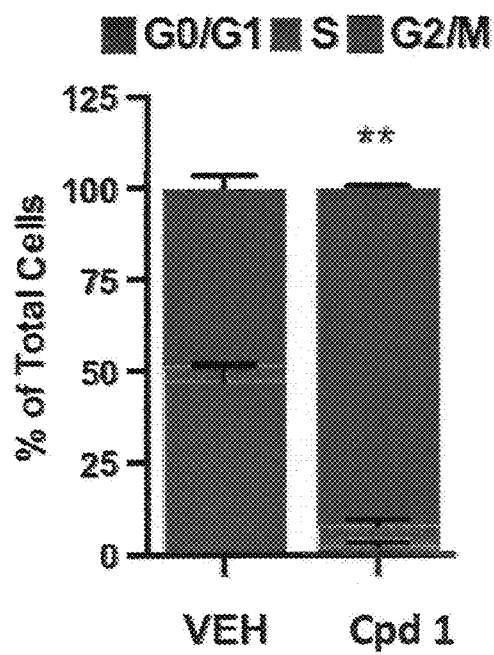
FIG. 10g is a graph of the percent of J1002TAM cells in G0/G1 phase, S phase, and G2/M phase following 24 hours after treatment with vehicle (VEH) or 1.0 µM Compound 1 (Cpd 1).

Confocal imaging was performed using an A1 laser scanning confocal attachment on an Eclipse Ti microscope stand using a 60x/1.49 ApoTIRF oil-immersion objective and standard lasers and filter sets (Nikon Instruments, Melville, N.Y.). The pinhole diameter was set to 1 Airy unit, and single optical sections were acquired near the basal surface of the cells to maximize detection of microtubules. All imaging conditions were kept constant. Images were visualized, analyzed, and prepared for publication using the Fiji distribution of ImageJ (Schindelin J, Arganda-Carreras I, Frise E, et al. Fiji: an open-source platform for biological-image analysis. Nature Methods 2012; 9:676-682). (FIG. 10d and FIG. 10f)

Animal Breeding and Genotyping

Genetically engineered models were generated by intercrossing the following engineered strains, of mixed genetic backgrounds:

$Kras^{LSL.G12D}$—Reported in Tuveson D A, Shaw A T, Willis N A, et al. Endogenous oncogenic K-ras (G12D) stimulates proliferation and widespread neoplastic and developmental defects, Cancer Cell 2004; 5:375-87.

$Tp53^{LSL.R172H}$—Reported in Olive K P, Tuveson D A, Ruhe Z C, et al. Mutant p53 gain of function in two mouse models of Li-Fraumeni syndrome, Cell 2004; 119:847-60.

Pdx1-$Cre^{tg}$—Reported in Hingorani S R, Petricoin E F, Maitra A, et al. Preinvasive and invasive ductal pancreatic cancer and its early detection in the mouse, Cancer Cell 2003; 4:437-50.

$Tp53^{Rox}$—Reported in Jonkers J, Meuwissen R, van der Gulden H, et al. Synergistic tumor suppressor activity of BRCA2 and p53 in a conditional mouse model for breast cancer, Nat Genet 2001; 29:418-25.

$Kras^{FSF.G12D}$—Jackson Laboratory, Stock No. 008653.

$Tp53^{R172H}$—This strain was generated by crossing the $Tp53^{LSL.R172H}$ strain with a Deleter-Cre to induce germline recombination, and then crossing out the Cre allele. This induced recombination of the Lox-STOP-LOX cassette in the $Tp53^{LSL.R172H}$ allele, resulting in a germline $Tp53^{R172H}$ allele with a single exogenous LoxP site in intron 1.

Pdx1-$FlpOt^{tg}$—The proximal 6 kb promoter of the Pdx1-Cre transgene was fused to the start codon of mammalian codon-optimized, thermostable Flp recombinase (FlpO), with subsequent fusion of the 5' end of the FlpO open reading frame to the hGH polyadenylation signal sequence.

$Bmi1^{Rox}$—Described in Mich J K, Signer R A, Nakada D, et al. Prospective identification of functionally distinct stem cells and neurosphere-initiating cells in adult mouse forebrain, Elife 2014; 3:e02669.

$Rosa26^{Cre-ERT2}$—Described in Ventura A, Kirsch D G, McLaughlin M E, et al. Restoration of p53 function leads to tumour regression in vivo, Nature 2007; 445:661-5.

$Kras^{LSL.G12D/+}$; $p53^{LSL.G12D/+}$; Pdx1-$Cre^{tg/+}$ (KPC) mice and related models were utilized as described in Hingorani S R, Wang L, Multani A S, et al. Trp53R172H and KrasG12D cooperate to promote chromosomal instability and widely metastatic pancreatic ductal adenocarcinoma in mice, Cancer Cell 2005; 7:469-83. J1002 cells were derived from an autochthonous pancreatic tumor in a $Kras^{FSF.G12D/+}$; $p53^{R172H/+}$; Pdx1-$FlpOt^{tg/+}$; $Bmi1^{Fl/Fl}$; $Rosa26^{reERT2/+}$ (KPFBR) mouse that arose following ceru-lean treatment (to accelerate tumor development), but prior to tamoxifen treatment. Genotyping was performed by Transnetyx (Cordova, Tenn.). Studies utilized both male and female animals. Animals were provided standard chow and housed under a 12-hour light/dark cycle.

Generation of KPFBR Primary Tumor Cell Lines

A small piece of tumor (~30 mg) was mechanically dissociated by chopping with sterile scissors for a minimum of five minutes in ice-cold tumor digestion buffer (5 mL/sample). Tumor digestion buffer consisted of 75 μg/mL DNase I (ThermoScientific, EN0521), 80 ug/mL Dispase II (ThermoFisher, 17105041), and 1 mg/mL Collagenase V (Sigma Aldrich, C9263) diluted in sterile PBS. After chopping, the dissociated tumor was incubated in digestion buffer at 37° C. for 20 minutes. Following digestion, 40 mL of ice cold PBS was used to dilute the digested tumor and the entire 45 mL was filtered through a 70 μm sterile mesh filter. The single cell suspension was spun down (300×g, 5 min), washed once with PBS, resuspended in serum-free ductal media (SFDM, recipe below) and plated in 1-2 wells of a collagen-coated 6-well plate (Corning, 354400). Cells were expanded in SFDM on collagen-coated plates, and transitioned to standard DMEM (10% FBS, 1% Pen-Strep, 1% L-glutamine) and standard tissue culture plates (no collagen).

SFDM Recipe:
DMEM/F-12 media (ThermoFisher, 12634010)
1.22 mg/mL nicotinamide (Sigma, N3376)
5 mg/mL glucose (Sigma, G6152)
5% ITS+ (BD Biosciences, 354352)
2.5 ug/mL Amphotericin B (ThermoFisher, 15290018)
5% Nu-serum IV (Corning, 392-0321)
25 ug/mL Bovine Pituitary Extract (Sigma, 1476)
20 ng/mL EGF (ThermoFisher, PMG8041)
50 nM 3,3'5-Triiodo-L-thyronine (Sigma, 564605)
1 uM Dexamethasone (Sigma, D1756)
100 ng/mL cholera toxin (Quadratech, 100)

Assessment of Bmi1 Deletion

In order to assess recombination of the conditional Bmi1 allele in J1002 cells, PCR was performed on DNA isolated by phenol-chloroform-isoamyl alcohol extraction. Cells were digested overnight at 55° C. in lysis buffer (10 mM Tris pH 7.5, 10 mM EDTA, 10 mM NaCl, and 0.5% sarkosyl)

supplemented with 1 mg/mL Proteinase K (New England BioLabs, P8107S). The following day, DNA was isolated by combining the lysates with a mixture of 50% phenol, 48% chloroform, and 2% isoamyl alcohol and centrifuging at 16,000×g for 30 minutes. The DNA-containing top layer was removed, and precipitated and washed with 2.5 volumes of 100% ethanol. DNA concentrations were measured using a ThermoScientific™ NanoDrop 2000 spectrophotometer. PCR reactions were carried out using GoTaq® Green Master Mix (Promega, M712B), 1 ng of DNA, and 250 nM of each primer. Three primers were used (DN437, DN438, DN946) which amplify wildtype Bmi1 (Bmi1$^{WT}$), Bmi1 with inserted loxP sites (Bmi1$^{fl/fl}$), and recombed Bmi1 (Bmi1$^{\Delta}$) all in a single reaction. Following PCR, amplified DNA was resolved on a 2% agarose gel supplemented with SYBR™ Safe DNA Gel Stain (ThermoFisher, S33102) and visualized using a UV light.

Figure 12A:
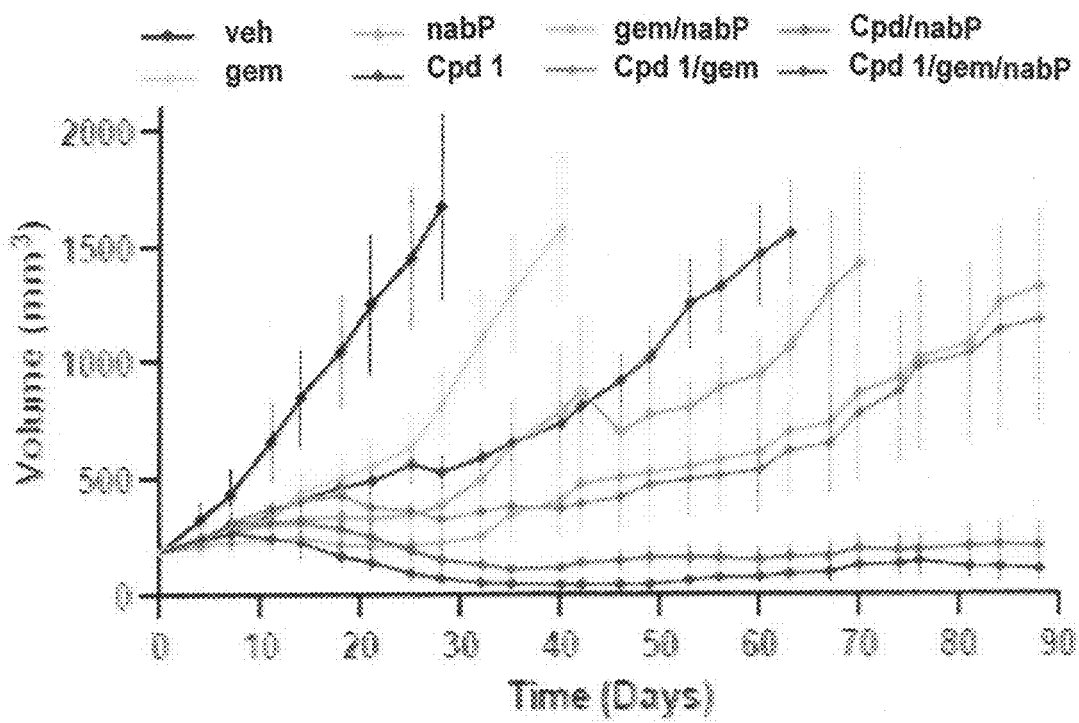
FIG. 12a a is a graph of average tumor volumes over time of subcutaneous patient-derived xenografts derived from a human PDA treated with vehicle (veh), gemcitabine (gem), nab-paclitaxel (nabP), a combination of gemcitabine and nab-paclitaxel (gm/nabP), Compound 1 (Cpd 1), a combination of Compound 1 and gemcitabine (Cpd 1/gem), a combination of Compound 1 and nab-paclitaxel (Cpd 1/nabP), and a combination of Compound 1, gemcitabine, and nab-paclitaxel (Cpd 1/gem/nabP).
Figure 12B:
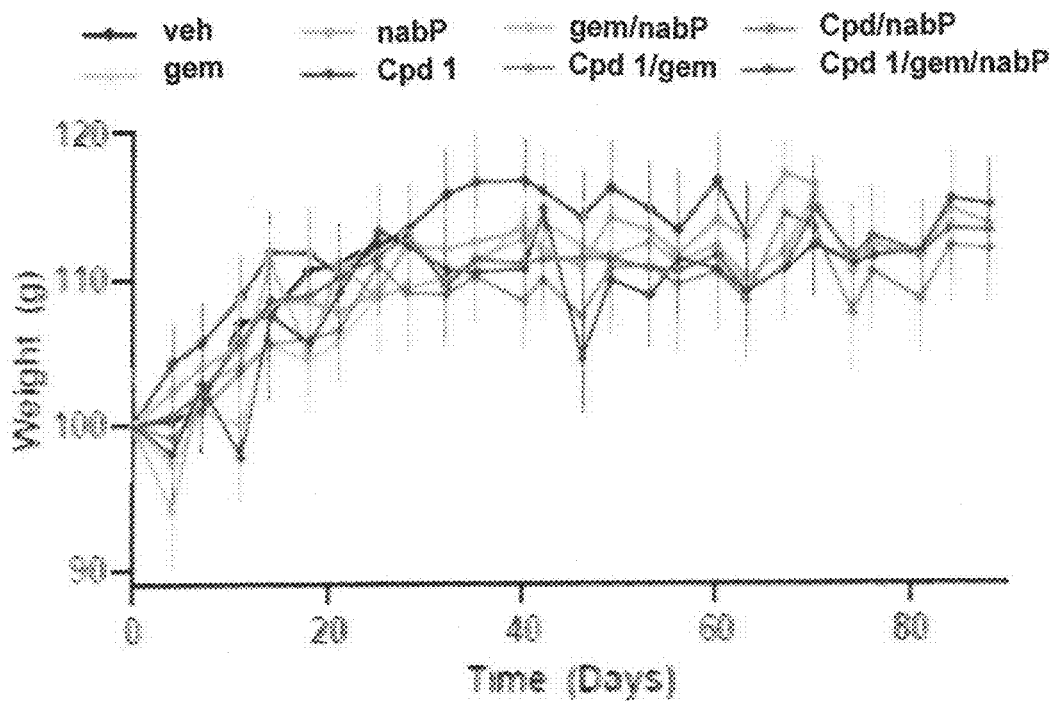
FIG. 12b is a graph of the body weight over time of mice treated with vehicle (veh), gemcitabine (gem), nab-paclitaxel (nabP), a combination of gemcitabine and nab-paclitaxel (gm/nabP), Compound 1 (Cpd 1), a combination of Compound 1 and gemcitabine (Cpd 1/gem), a combination of Compound 1 and nab-paclitaxel (Cpd 1/nabP), and a combination of Compound 1, gemcitabine, and nab-paclitaxel (Cpd 1/gem/nabP).
Figure 12C:
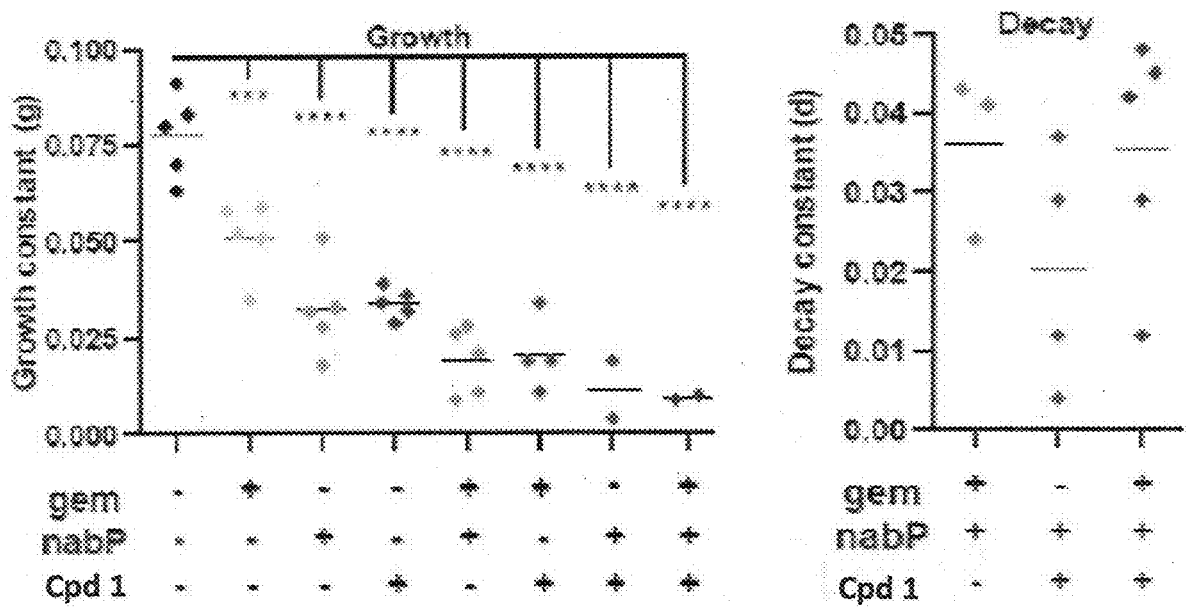
FIG. 12c depicts growth and decay constants for tumors treated with gemcitabine (gem), nab-paclitaxel (nabP), and Compound 1 (Cpd 1).
Figure 12D:
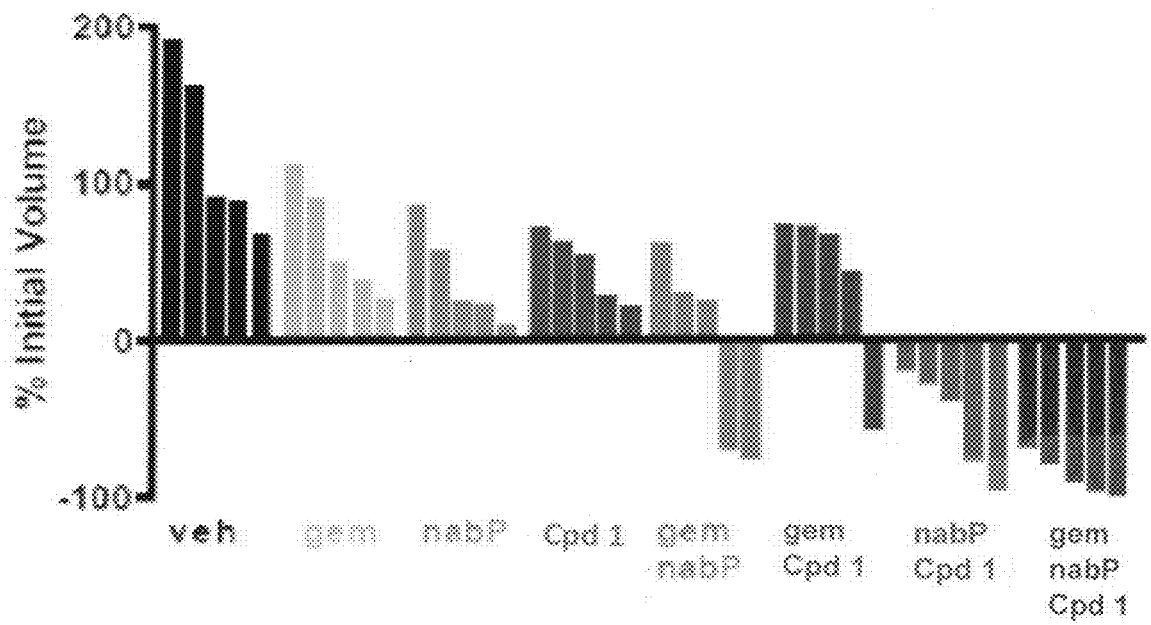
FIG. 12d is a plot of tumor response of each mouse treated with vehicle (veh), gemcitabine (gem), nab-paclitaxel (nabP), a combination of gemcitabine and nab-paclitaxel (gm/nabP), Compound 1 (Cpd 1), a combination of Compound 1 and gemcitabine (Cpd 1/gem), a combination of Compound 1 and nab-paclitaxel (Cpd 1/nabP), and a combination of Compound 1, gemcitabine, and nab-paclitaxel (Cpd 1/gem/nabP).

Primers:
DN437: gctagcattcctggttttgc
DN438: ggcacagtgatgaggtgttg
DN946: cacgaggtgcttctttcctc
Cycling Conditions:
1. 95° C., 2 min
2. 95° C., 15 sec
3. 51.4° C., 15 sec
4. 68° C., 45 sec
   (Repeat steps 2-4 30 times)
5. 68° C., 5 min
6. 4° C., forever
Expected Amplicons:
Wildtype Bmi1 (Bmi1$^{WT}$)=400 bp
Floxed Bmi1 (Bmi1$^{fl/fl}$)=500 bp
Recombed Bmi1 (Bmi1$^{\Delta}$)=300 bp PDX Model Intervention Study Early passage tumor fragments from Champions model CTG-1462 were implanted subcutaneously in nu/nu mice and then randomized to a treatment arm once tumors reached 150-300 mm$^3$. Mice (n=5/group) were treated on one of seven arms: vehicle, gemcitabine (50 mg/kg, q.w., IP), nab-paclitaxel (10 mg/kg, IV, q.w.×3), Compound 1 (12.5 mg/kg, b.i.w.×4, PO), or full dose combinations of gemcitabine+nab-paclitaxel, gemcitabine+Compound 1, nab-paclitaxel+Compound 1, or gemcitabine+nab-paclitaxel+Compound 1. Endpoints were when a tumor reached 1500 mm$^3$ or after 90 days on study. Length (L) and width (W) diameters of tumors were measured using digital calipers and mice were weighed twice per week. Tumor volume was calculated as (L×W$^2$)/2. (FIG. 12a and FIG. 12b)

KPC Intervention/Survival Study

Tumor formation in KPC mice was monitored by weekly palpation until the detection of a mass. Upon positive palpation, the mass was monitored by twice weekly ultrasound until the tumor reached an enrollable size of 4-7 mm average diameter. Once enrollable, KPC mice were randomly enrolled into a treatment arm of the intervention study. Mice were treated with vehicle, Compound 1 (17 mg/kg, PO, b.i.w.), gemcitabine alone (100 mg/kg, IP, b.i.w.), or Compound 1+gemcitabine. Mice receiving Compound 1 also received gemcitabine vehicle (saline, IP, b.i.w.) at a volume (µL) of 50× body weight (g). Mice receiving gemcitabine also received Compound 1 vehicle (0.5% hydroxypropylmethylcellulose with 0.1% Tween80 (w/v), PO, b.i.w.) at a volume (µL) of 5.7× body weight (g). All drug and vehicle combinations were administered simultaneously.

Measurement of Compound 1 Levels in Plasma and Tissue Samples

Blood plasma and tissue samples to be used for analysis were immediately frozen on dry ice and stored at −80° C. until analysis. Concentrations of Compound 1 in samples were quantified using high-performance liquid chromatography with tandem mass spectrometry (LC-MS/MS). Compound 1 and its internal standard (deuterated Compound 1) were recovered by protein precipitation extraction from samples.

For the plasma pharmacokinetic time course study, a standard curve was made to cover concentrations between 0.001 ug/mL and 3.0 µg/mL. The lower limit of quantification (LLOQ) for Compound 1 (either version) in plasma was 0.001 µg/mL. (FIG. 4a)

For the pharmacokinetic study that assessed plasma, quadriceps muscle, and tumor tissue following a single dose of Compound 1 the assay conditions were as follows (FIG. 5a):

Plasma: A standard curve was made to cover concentrations between 0.002 ug/mL and 6.0 ug/mL. the LLOQ for Compound 1 (either version) in plasma was 0.001 µg/mL Quadriceps muscle: A standard curve was made to cover concentrations between 0.001 µg/g wet tissue and 3.0 µg/g wet tissue. The LLOQ for Compound 1 (either version) was 0.01 µg/g wet tissue.

Tumor tissue: A standard curve was made to cover concentrations between 0.001 µg/g wet tissue and 3.0 µg/g wet tissue. The LLOQ for Compound 1 (either version) was 0.02 µg/g wet tissue.

Ultrasound

Figure 7A:
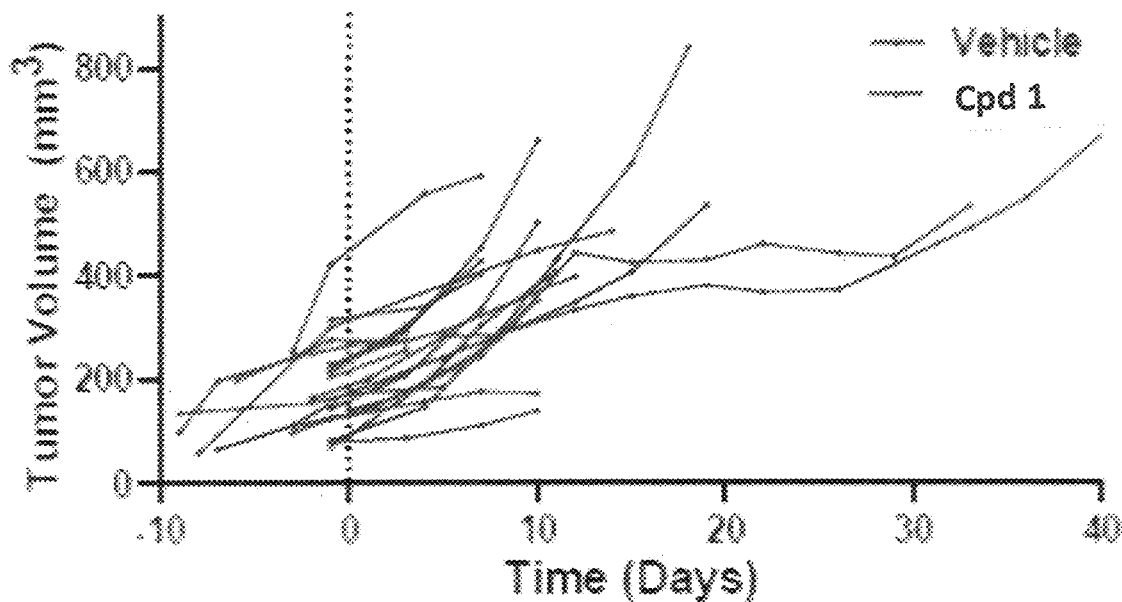
FIG. 7a is a plot of tumor volumes measured by high resolution 3D ultrasound for KPC mice treated with vehicle (veh) or Compound 1 (Cpd 1).
Figure 7B:
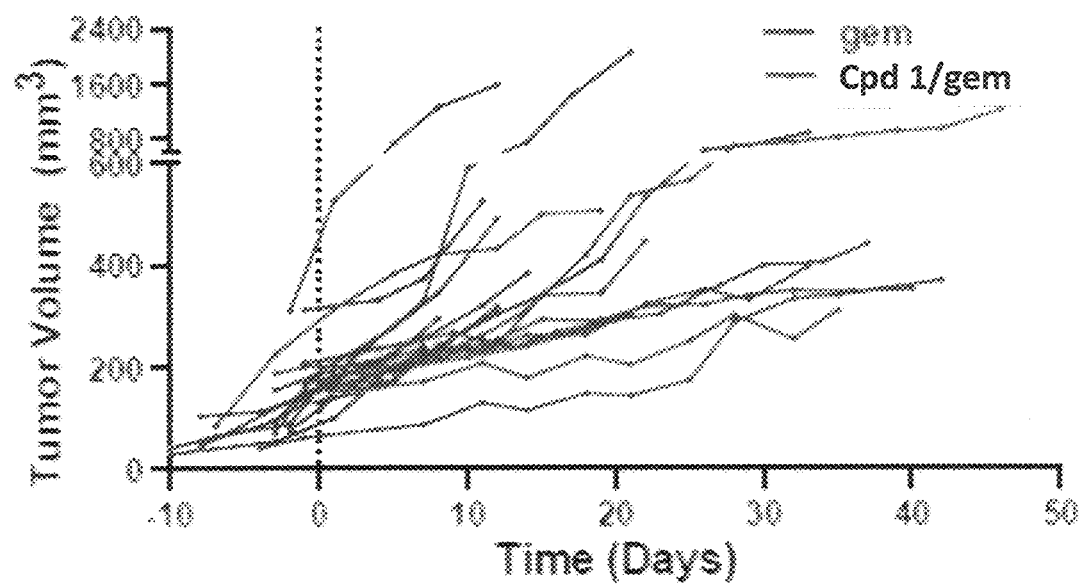
FIG. 7b is a plot of tumor volumes measured by high resolution 3D ultrasound for KPC mice treated with vehicle (veh) or a combination of Compound 1 and gemcitabine (Cpd 1/gem).
Figure 8A:
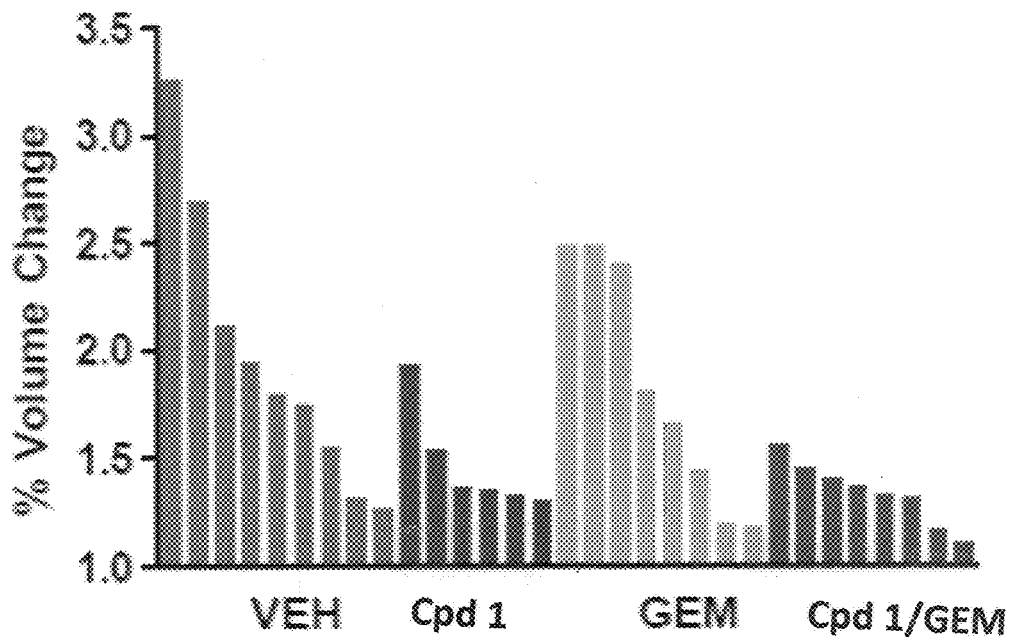
FIG. 8a is a plot of tumor growth measured by percent volume change over 7 days in KPC mice treated with vehicle (VEH), Compound 1 (Cpd 1), gemcitabine (GEM), or a combination of Compound 1 and gemcitabine (Cpd 1/GEM).
Figure 8B:
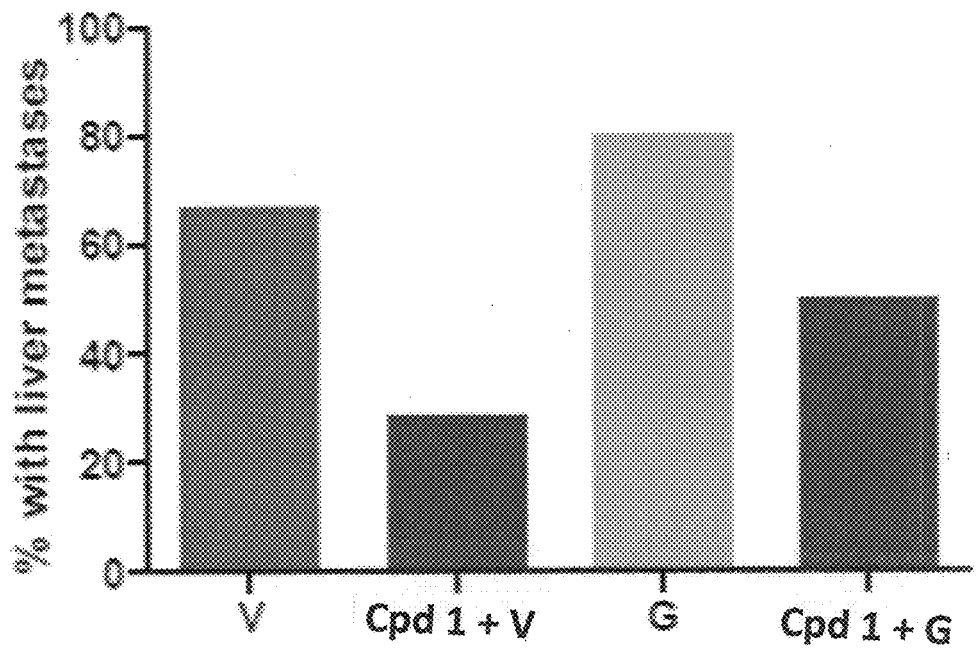
FIG. 8b is a plot of the percent of mice having liver metastases in KPC mice treated with vehicle (V), Compound 1 (Cpd 1+V), gemcitabine (G), or a combination of Compound 1 and gemcitabine (Cpd 1+G).
Figure 9A:
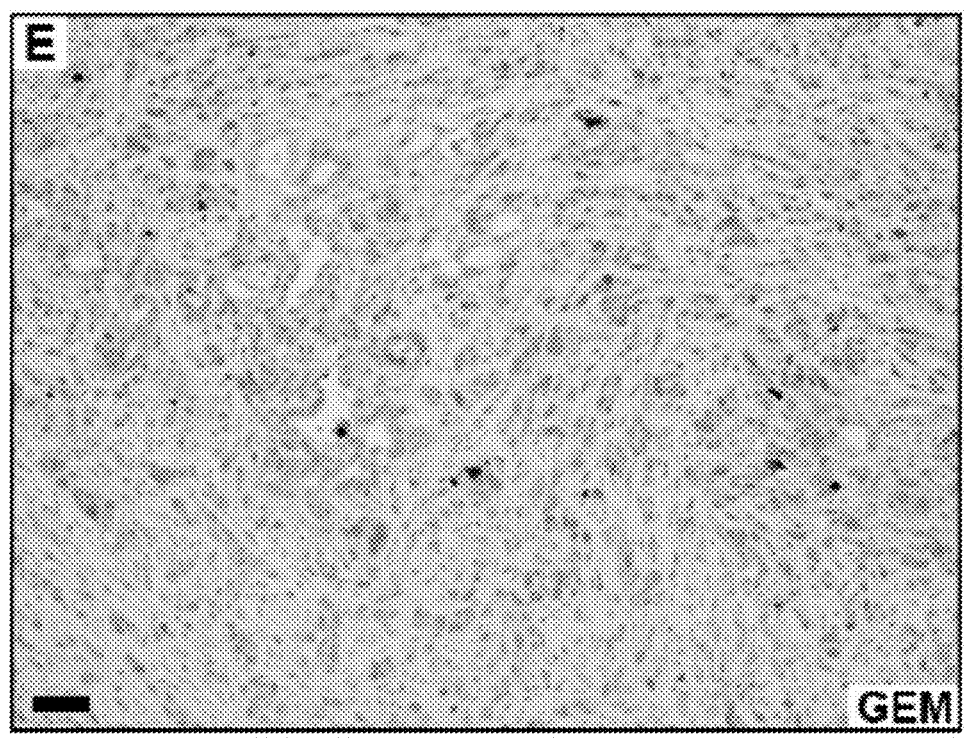
FIG. 9a is a stained tumor section from KPC mice treated with gemcitabine (GEM).
Figure 9B:
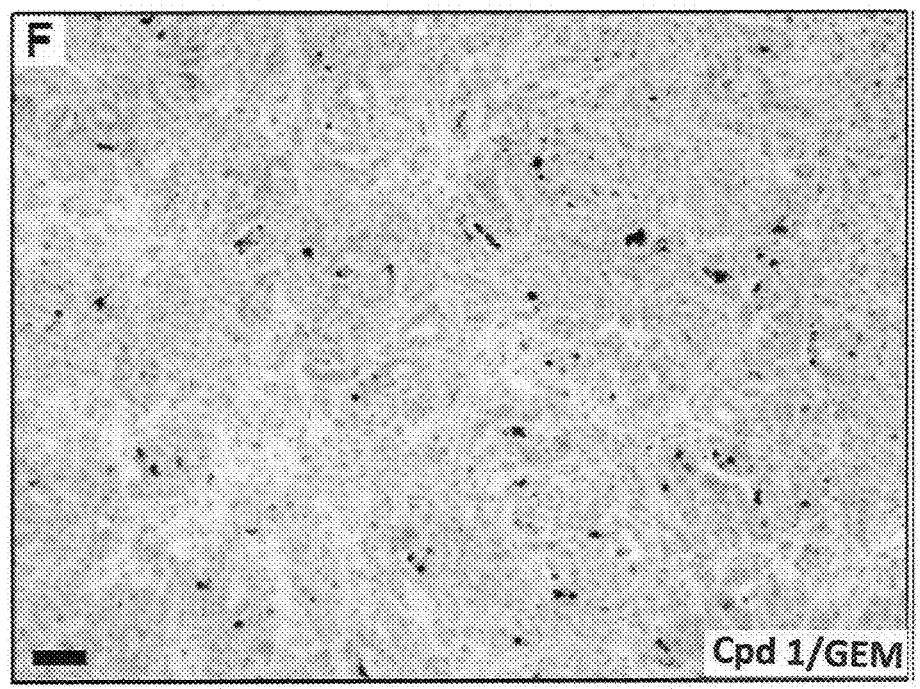

Tumor ultrasonography and volume quantification were carried out as described in Sastra S A, Olive K P, Quantification of murine pancreatic tumors by high-resolution ultrasound, Methods Mol Biol 2013; 980:249-66. (FIG. 7a and FIG. 7b)

Immunohistochemistry

To prepare samples for immunohistochemistry, tissues were first fixed overnight in 10% phosphate-buffered formalin and then stored in 70% ethanol for long-term storage. Fixed tissues then underwent a standard dehydration protocol and were embedded in paraffin wax blocks. Tissues were sectioned to 5 µm thickness using a Leica RM 2235 microtome, mounted on positively-charged glass slides, and baked at 60° C. for 30 minutes. To prepare for staining, slides were first deparaffinized in xylene and then re-hydrated in a series of ethanol steps, before rinsing in distilled water. Next, antigen retrieval was carried out in an experimentally determined, antibody-specific antigen retrieval buffer (usually 10 mM citrate, pH 6.0 or 10 mM Tris, pH 10.0). Antigen retrieval buffer was heated to boiling in a pressure-cooker, at which point slides were introduced for 5 minutes. After cooling to room temperature, slides were immersed in 3% hydrogen peroxide in PBS for 20 minutes in order to quench endogenous peroxidases.

Figure 6A:
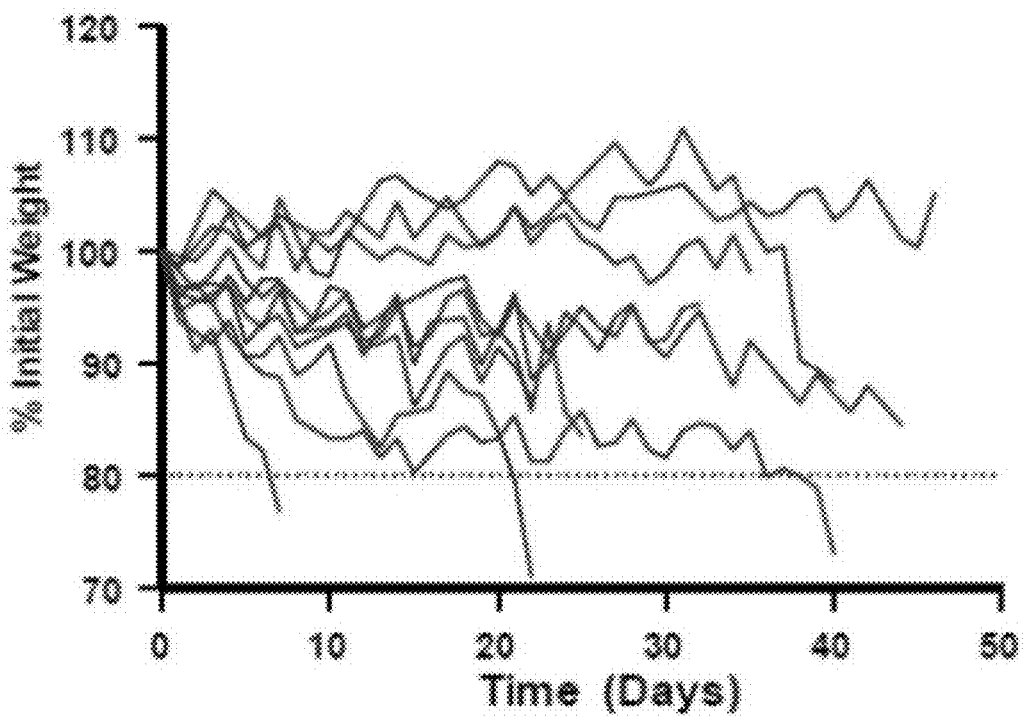
FIG. 6a is a plot of body weights over time of KPC mice treated with a combination of Compound 1 and gemcitabine.
Figure 6B:
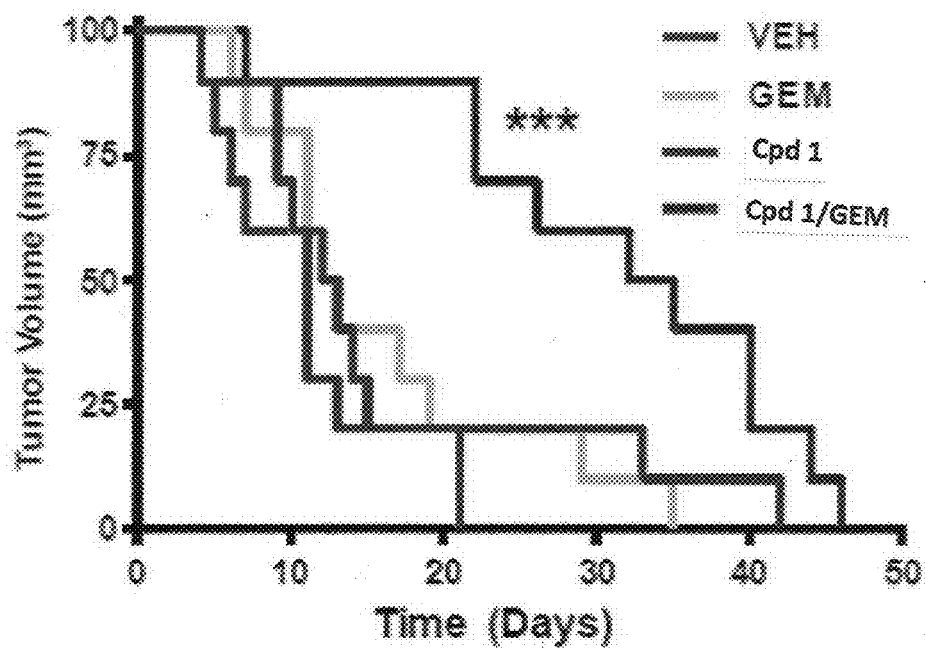
FIG. 6b is a plot of survival over time of KPC mice treated with vehicle (VEH), gemcitabine (GEM, 100 mg/kg b.i.w.), Compound 1 (Cpd 1, 17 mg/kg b.i.w.), or a combination of Compound 1 and gemcitabine (Cpd/GEM).
Figure 6C:
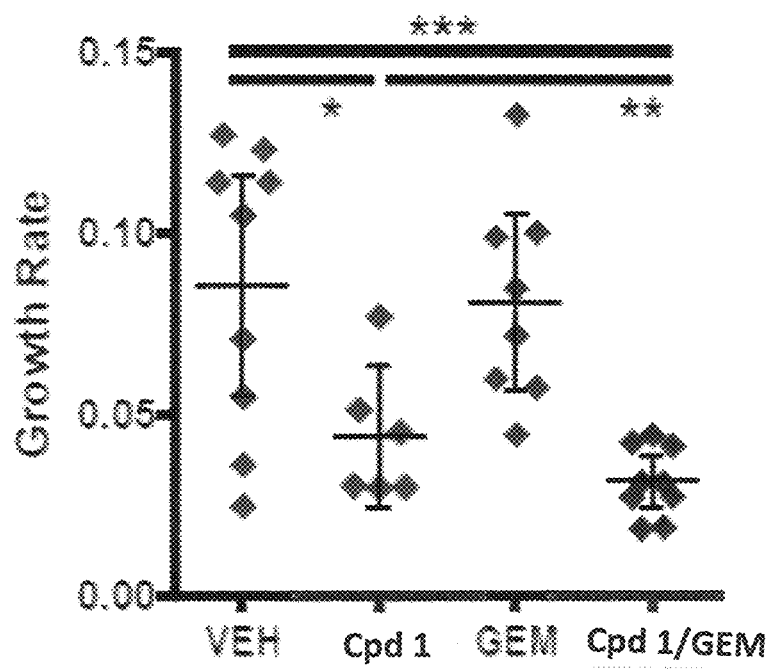
FIG. 6c is a plot of tumor growth rate calculations calculated from longitudinal tumor volumes in KPC mice treated with vehicle (VEH), gemcitabine (GEM), Compound 1 (Cpd 1), or a combination of Compound 1 and gemcitabine (Cpd/GEM).
Figure 6D:
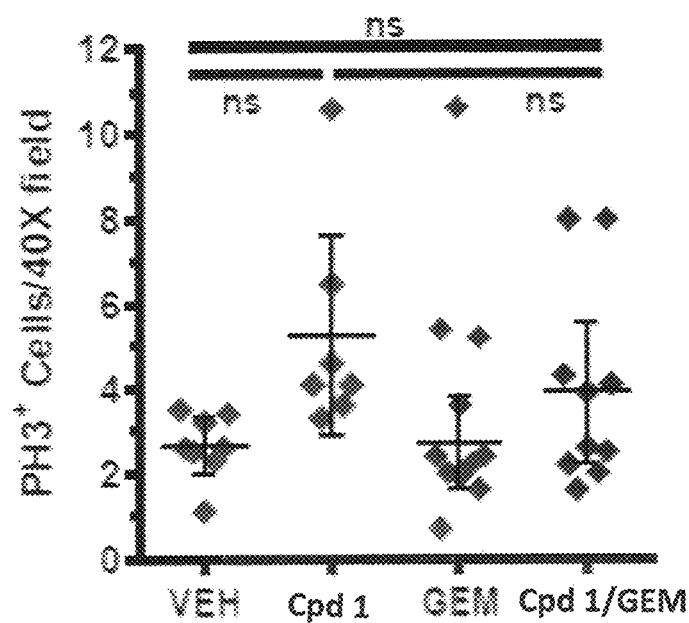
FIG. 6d is a plot of quantification of immunohistochemistry for phosphorylated Histone H3 (PH3) cells showing average positive cells per 40× field over 10 fields per tumor following necropsy in KPC mice treated with vehicle (VEH), gemcitabine (GEM), Compound 1 (Cpd 1), or a combination of Compound 1 and gemcitabine (Cpd/GEM).
Figure 6E:
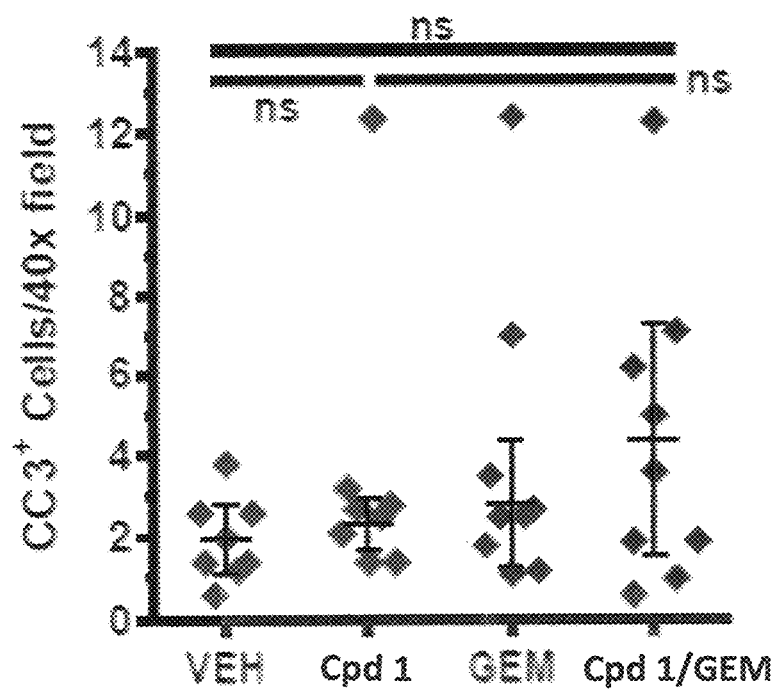
FIG. 6e is a plot of quantification of immunohistochemistry for phosphorylated cleaved Caspase-3 (CC3) cells showing average positive cells per 40× field over 10 fields per tumor following necropsy in KPC mice treated with vehicle (VEH), gemcitabine (GEM), Compound 1 (Cpd 1), or a combination of Compound 1 and gemcitabine (Cpd 1/GEM).

Slides were then blocked for one hour at room temperature in TBS-T (0.1% Tween20)+1.5% normal horse serum (Vector Laboratories, S-2000)+2% Animal Free Blocker (Vector Laboratories, SP-5030). Primary antibodies were diluted in blocking solution and incubated overnight at 4° C. at the indicated concentrations. The following day, secondary antibody incubation was carried out at room temperature for 30 minutes using the ImmPRESS HRP Anti-Rabbit IgG (Peroxidase) Polymer Detection Kit (Vector Laboratories, MP-7401). Detection was carried out with ImmPACT DAB Peroxidase (HRP) Substrate (Vector Laboratories, SK-4105) and slides were subsequently counterstained with hematoxylin, dehydrated to xylene, and coverslipped with Permount (Fisher, S70104). (FIG. 6d and FIG. 6e)

IHC antibodies:
PH3: Cell Signaling, #9701, 1:100
CC3: Cell Signaling, #9664S, 1:100

What is claimed is:

1. A method for treating pancreatic cancer in a subject in need thereof comprising, administering to the subject a combination consisting essentially of an effective amount of 5-fluoro-2-(6-fluoro-2-methyl-1H-benzo[d]imidazol-1-yl)-N4-[4-(trifluoromethyl)phenyl]pyrimidine-4,6-diamine, having the structure of Formula (I):

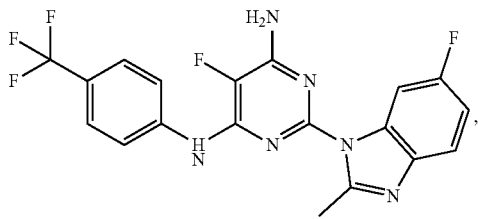

Formula (I)

or a pharmaceutically acceptable salt thereof, and an effective amount of nab-paclitaxel.

2. The method of claim 1, wherein the pancreatic cancer is pancreatic ductal adenocarcinoma.

3. The method of claim 1, wherein a pharmaceutical composition comprises the 5-fluoro-2-(6-fluoro-2-methyl-1H-benzo[d]imidazol-1-yl)-N4-[4-(trifluoromethyl)phenyl]pyrimidine-4,6-diamine or pharmaceutically acceptable salt thereof.

4. The method of claim 1, wherein the effective amount of 5-fluoro-2-(6-fluoro-2-methyl-1H-benzo[d]imidazol-1-yl)-N4-[4-(trifluoromethyl)phenyl]pyrimidine-4,6-diamine, or pharmaceutically acceptable salt thereof, achieves a mean plasma concentration in a 24 hour period of from approximately 3 hr·μg/ml to approximately 70 hr·μg/ml.

5. The method of claim 1, wherein the effective amount of 5-fluoro-2-(6-fluoro-2-methyl-1H-benzo[d]imidazol-1-yl)-N4-[4-(trifluoromethyl)phenyl]pyrimidine-4,6-diamine, or pharmaceutically acceptable salt thereof, achieves a mean plasma concentration in a 24 hour period of from approximately 3 hr·μg/ml to approximately 60 hr·μg/ml.

6. The method of claim 1, wherein the effective amount of 5-fluoro-2-(6-fluoro-2-methyl-1H-benzo[d]imidazol-1-yl)-N4-[4-(trifluoromethyl)phenyl]pyrimidine-4,6-diamine, or pharmaceutically acceptable salt thereof, achieves a mean plasma concentration in a 24 hour period of from approximately 3 hr·μg/ml to approximately 50 hr·μg/ml.

7. The method of claim 1, wherein the effective amount of 5-fluoro-2-(6-fluoro-2-methyl-1H-benzo[d]imidazol-1-yl)-N4-[4-(trifluoromethyl)phenyl]pyrimidine-4,6-diamine, or pharmaceutically acceptable salt thereof, achieves a mean plasma concentration in a 24 hour period of from approximately 3 hr·μg/ml to approximately 40 hr·μg/ml or from approximately 3 hr·μg/ml to approximately 30 hr·μg/ml.

* * * * *